(12) United States Patent
Behrens et al.

(10) Patent No.: US 8,148,074 B2
(45) Date of Patent: Apr. 3, 2012

(54) IRF-5 HAPLOTYPES IN SYSTEMIC LUPUS ERYTHEMATOSUS

(75) Inventors: Timothy W. Behrens, Burlingame, CA (US); Robert R. Graham, San Francisco, CA (US); David Altshuler, Brookline, MA (US)

(73) Assignees: Regents of the University of Minnesota, Saint Paul, MN (US); General Hospital Corporation, Boston, MA (US)

( * ) Notice: Subject to any disclaimer, the term of this patent is extended or adjusted under 35 U.S.C. 154(b) by 0 days.

(21) Appl. No.: 12/565,480

(22) Filed: Sep. 23, 2009

(65) Prior Publication Data

US 2010/0092977 A1 Apr. 15, 2010

Related U.S. Application Data

(63) Continuation of application No. 11/694,272, filed on Mar. 30, 2007, now abandoned.

(51) Int. Cl.
*C12Q 1/68* (2006.01)
*C07H 21/04* (2006.01)

(52) U.S. Cl. ...................... 435/6.11; 536/23.5

(58) Field of Classification Search .......... None
See application file for complete search history.

(56) References Cited

U.S. PATENT DOCUMENTS

| | | | |
|---|---|---|---|
| 4,469,863 A | 9/1984 | Ts'o et al. | |
| 4,816,567 A | 3/1989 | Cabilly et al. | |
| 5,143,854 A | 9/1992 | Pirrung et al. | |
| 5,235,033 A | 8/1993 | Summerton et al. | |
| 5,482,856 A | 1/1996 | Fell, Jr. et al. | |
| 5,565,332 A | 10/1996 | Hoogenboom et al. | |
| 5,596,086 A | 1/1997 | Matteucci et al. | |
| 5,744,305 A | 4/1998 | Fodor et al. | |
| 5,750,666 A | 5/1998 | Caruthers et al. | |
| 6,054,297 A | 4/2000 | Carter et al. | |
| 6,630,358 B1 | 10/2003 | Wagner et al. | |
| 6,808,901 B1 | 10/2004 | Neuberger et al. | |
| 6,933,146 B2 | 8/2005 | Helliwell et al. | |
| 2003/0148298 A1 | 8/2003 | O'Toole et al. | |
| 2004/0009479 A1 | 1/2004 | Wohlgemuth et al. | |
| 2004/0033498 A1 | 2/2004 | Behrens et al. | |

FOREIGN PATENT DOCUMENTS

| | | |
|---|---|---|
| WO | WO 99/57318 | 11/1999 |
| WO | WO 00/22093 | 4/2000 |
| WO | WO 02/057414 | 7/2002 |
| WO | WO 03/090694 | 11/2003 |

OTHER PUBLICATIONS

Kozyrev, S.V. et al. Arthritis & Rheumatism 56(4):1234-1241 (Apr. 2007; online publication Mar. 28, 2007).*
Pascual, V. et al. Current Opinion in Rheumatology 15:548-556 (2003).*
Cunninghame Graham, D.S. et al. Human Molecular Genetics 16(6):579-591 (online publication Dec. 26, 2006).*

(Continued)

*Primary Examiner* — Diana Johannsen
(74) *Attorney, Agent, or Firm* — Fish & Richardson P.C.

(57) ABSTRACT

Methods and materials involved in diagnosing SLE are provided herein. The methods and materials can be used to diagnose SLE and/or assess a mammal's susceptibility to develop SLE, based on the presence or absence of one or more IRF-5 variants.

4 Claims, 13 Drawing Sheets

OTHER PUBLICATIONS

Graham, R.R. et al. Nature Genetics 38(5):550-555 (online publication Apr. 16, 2006).*
Sigurdsson, S. et al. American Journal of Human Genetics 76:S28-S37 (2005).*
GenBank Accession No. DQ277633, dated Jun. 13, 2006, 2 pages.
GenBank Accession No. DQ277634, dated Jun. 13, 2006, 2 pages.
GenBank Accession No. L13210, dated Jun. 26, 1993, 2 pages.
GenBank Accession No. X54486, dated Nov. 14, 2006, 8 pages.
Alarcón et al., "Systemic Lupus Erythematosus in Three Ethnic Groups. II. Features Predictive of Disease Activity Early in Its Course," *Arth. Rheum.*, 1998, 41(7):1173-1180.
Alarcón-Segovia et al., "Familial aggregation of systemic lupus erythematosus, rheumatoid arthritis, and other autoimmune diseases in 1,177 lupus patients from the GLADEL cohort," *Arth. Rheum.*, 2005, 52:1138-1147.
Aringer et al., "Serum interleukin-15 is elevated in systemic lupus erythematosus," *Rheumatology*, 2001, 40:876-881.
Arnett and Reveille, "Genetics of Systemic Lupus Erythematosus," *Rheum. Dis. Clin. N. Am.*, 1992, 18(4):865-892.
Asmal et al., "Production of Ribosome Components in Effector CD4+ T Cells Is Accelerated by TCR Stimulation and Coordinated by ERK-MAPK," *Immunity*, 2003, 19:535-548.
Bae et al., "Reliability and validity of systemic lupus activity measure-revised (SLAM-R) for measuring clinical disease activity in systemic lupus erythematosus," *Lupus*, 2001, 10:405-409.
Baechler et al., "Expression levels for many genes in human peripheral blood cells are highly sensitive to ex vivo incubation," *Genes and Immunity*, 2004, 5:347-353.
Baechler et al., "Interferon-inducible gene expression signature in peripheral blood cells of patients with severe lupus," *Proc. Natl. Acad. Sci. USA*, 2003, 100:2610-2615.
Baggiolini, "Chemokines and leukocyte traffic," *Nature*, 1998, 392:565-568.
Balomenos et al., "Interferon-γ is Required for Lupus-like Disease and Lymphoaccumulation in MRL-lpr Mice," *J. Clin. Invest.*, 1998, 101(2):364-371.
Barnes et al., "Virus-specific activation of a novel interferon regulatory factor, IRF-5, results in the induction of distinct interferon alpha genes," *J. Biol. Chem.*, 2001, 276:23382-23390.
Barnes et al., "Multiple regulatory domains of IRF-5 control activation, cellular localization, and induction of chemokines that mediate recruitment of T lymphocytes," *Mol. Cell. Biol.*, 2002, 22:5721-5740.
Barnes et al., "Global and distinct targets of IRF-5 and IRF-7 during innate response to viral infection," *J. Biol. Chem.*, 2004, 279:45194-45207.
Barrett et al., "Haploview: analysis and visualization of LD and haplotype maps," *Bioinformatics*, 2005, 21:263-265.
Bauer et al., "Elevated Serum Levels of Interferon-Regulated Chemokines Are Biomarkers for Active Human Systemic Lupus Erythematosus," *PLoS Med.*, 2006, 3(12):e491.
Bennett et al., "Interferon and granulopoiesis signatures in systemic lupus erythematosus blood," *J. Exp. Med.*, 2003, 197:711-723.
Blanco et al., "Induction of dendritic cell differentiation by IFN-alpha in systemic lupus erythematosus," *Science*, 2001, 294:1540-1543.
Bombardier et al., "Derivation of the SLEDAI. A Disease Activity Index for Lupus Patients," *Arthritis Rheum.*, 1992, 35(6):630-640.
Braun et al., "Type I Interferon controls the onset and severity of autoimmune manifestations in *lpr* mice," *J. Autoimmun.*, 2003, 20:15-25.
Buttrum et al., "Changes in neutrophil rheology after acute ischemia and reperfusion in the rat hindlimb," *J. Lab. Clin. Med.*, 1996, 128(5):506-514.
Cann et al., "A human genome diversity cell line panel," *Science*, 2002, 296:261-262.
Cheung et al., "Mapping determinants of human gene expression by regional and genome-wide association," *Nature*, 2005, 437:1365-1369.
Chuang and Ulevitch, "Cloning and characterization of a sub-family of human toll-like receptors: hTLR7, hTLR8 and hTLR9," *Eur. Cytokine Netw.*, 2000, 11:372-378.
Cogoni and Masino, "Gene silencing in Neurospora crassa requires a protein homologous to RNA-dependent RNA polymerase," *Nature*, 1999, 399:166-169.
Cogoni et al., "Transgene silencing of the al-1 gene in vegetative cells of Neurospora is mediated by a cytoplasmic effector and does not depend on DNA-DNA interactions or DNA methylation," *EMBO J.*, 1996, 15:3153-3163.
Coleman, "Of mouse and man—what is the value of the mouse in predicting gene expression in humans?" *Drug Discovery Today*, 2003, 8(6):233-235.
Conne et al., "The 3' untranslated region of messenger RNA: A molecular 'hotspot' for pathology," *Nat. Med.*, 2000, 6:637-641.
Cyster, "Homing of antibody secreting cells," *Immunol. Rev.*, 2003, 194:48-60.
de Bakker et al., "Efficiency and power in genetic association studies," *Nat. Genet.*, 2005, 37:1217-1223.
de Veer et al., "Functional classification of interferon-stimulated genes identified using microarrays," *J. Leukocyte Biology*, 2001, 69:912-920.
Der et al., "Identification of genes differentially regulated by interferon α, β, or γ using oligonucleotide arrays," *Proc. Natl. Acad. Sci. USA*, 1998, 95:15623-15628.
Dörner and Lipsky, "Correlation of circulating $CD27^{high}$ plasma cells and disease activity in systemic lupus erythematosus" *Lupus*, 2004, 13:283-289.
Du et al., "Three novel mammalian toll-like receptors: gene structure, expression, and evolution," *Eur. Cytokine Netw.*, 2000, 11:362-371.
Edmonds, "A history of poly A sequences: from formation to factors to function," *Prog. Nucl. Acid. Res. Mol. Biol.*, 2002, 71:285-389.
Eisen et al., "Cluster analysis and display of genome-wide expression patterns," *Proc. Natl. Acad. Sci. USA*, 1998, 95:14863-14868.
Fire et al., "Potent and specific genetic interference by double-stranded RNA in *Caenorhabditis elegans*," *Nature*, 1998, 391:806-811.
Fukuyama et al., "Systemic Lupus Erythematosus After α-Interferon Therapy for Chronic Hepatitis C: A Case Report and Review of the Literature," *Am. J. Gastroenterol.*, 2000, 95(1):310-312.
Gaffney et al., "A genome-wide search for susceptibility genes in human systemic lupus erythematosus sib-pair families," *Proc. Natl. Acad. Sci. USA*, 1998, 95:14875-14879.
Gaffney et al., "Genome screening in human systemic lupus erythematosus: results from a second Minnesota cohort and combined analyses of 187 sib-pair families,"*Am. J. Hum. Genet.*, 2000, 66:547-556.
Gergely, Jr. et al., "Persistent Mitochondrial Hyperpolarization, Increased Reactive Oxygen Intermediate Production, and Cytoplasmic Alkalinization Characterize Altered IL-10 Signaling in Patients with Systemic Lupus Erythematosus," *J. Immunol.*, 2002, 169:1092-1101.
Gibson, "Simulated evolution and artificial selection," *BioSystems*, 1989, 23:219-229.
Ginsburg et al., "Circulating and pokeweed mitogen-induced immunoglobulin-secreting cells in systemic lupus erythematosus," *Clin. Exp. Immunol.*, 1979, 35:76-88.
Gladman et al., "The development and initial validation of the Systemic Lupus International Collaborating Clinics/American College of Rheumatology damage index for systemic lupus erythematosus," *Arthritis Rheum.*, 1996, 39(3):363-369.
Graham et al., "A common haplotype of interferon regulatory factor 5 (IRF5) regulates splicing and expression and is associated with increased risk of systemic lupus erythematosus," *Nat. Genet.*, 2006, 38:550-555.
Graham et al., "Genetic linkage and transmission disequilibrium of marker haplotypes at chromosome 1q41 in human systemic lupus erythematosus," *Arthritis Res.*, 2001, 3:299-305.
Graham et al., "Evidence for unique association signals in SLE at the CD28-CTLA4-ICOS locus in a family-based study," *Hum. Mol. Genet.*, 2006, 15:3195-3205.

Gregersen and Brehrens, "Fine mapping the phenotype in autoimmune disease: the promise and pitfalls of DNA microarray technologies," *Genes and Immunity*, 2003, 4:175-176.
Grewal et al., "Transgenic Monocyte Chemoattractant Protein-1 (MCP-1) in Pancreatic Islets Produces Monocyte-Rich Insulitis Without Diabetes. Abrogation by a Second Transgene Expressing Systemic MCP-1," *J. Immunol.*, 1997, 159:401-408.
Gu et al., "Analysis of inflammation related gene expression spectrum in ankylosing spondylitis patients using cDNA microarray," *Natl. Med. J. China*, 2001, 81(17):1030-1034 (English Abstract included).
Harada et al., "Identification of early plasma cells in peripheral blood and their clinical significance," *Br. J. Haematol.*, 1996, 92:184-191.
Hase et al., "Increased CCR4 expression in active systemic lupus erythematosus," *J. Leukoc. Biol.*, 2001, 70:749-755.
Hay et al., "The BILAG index: a reliable and valid instrument for measuring clinical disease activity in systemic lupus erythematosus," *Q. J. Med.*, 1993, 86:447-458.
Hirano et al., "Roles of STAT3 in mediating the cell growth, differentiation and survival signals relayed through the IL-6 family of cytokine receptors," *Oncogene*, 2000, 19:2548-2556.
Hochberg, "Updating the American College of Rheumatology revised criteria for the classification of systemic lupus erythematosus," *Arthritis Rheum.*, 1997, 40:1725.
Hochberg and Benjamini, "More powerful procedures for multiple significance testing," *Stat. Med.*, 1990, 9:811-818.
Hoffman, "T cells in the pathogenesis of systemic lupus erythematosus," *Clin. Immunol.*, 2004, 113:4-13.
Holcombe et al., "Correlation of Serum Interleukin-8 and Cell Surface Lysosome-associated Membrane Protein Expression with Clinical Disease Activity in Systemic Lupus Erythematosus," *Lupus*, 1994, 3:97-102.
Honda et al., "Regulation of the type I IFN induction: a current view," *Int. Immunol.*, 2005, 17:1367-1378.
Hooks et al., "Immune interferon in the circulation of patients with autoimmune disease," *N. Engl. J. Med.*, 1979, 301:5-8.
Hyrup et al., "Peptide nucleic acids (PNA): synthesis, properties and potential applications," *Bioorgan. Med. Chem.*, 1996, 4:5-23.
International HapMap Consortium, "A haplotype map of the human genome," *Nature*, 2005, 437:1299-1320.
Isaacs and Lindenmann, "Virus interference. I. The interferon," *Proc. R. Soc. B*, 1957, 147:258-273.
Jacob et al., "In Vivo Treatment of (NZB×NZW)F1 Lupus-Like Nephritis with Monoclonal Antibody to γ Interferon," *J. Exp. Med.*, 1987, 166:798-803.
Jacobi et al., "Correlation Between Circulating CD27high Plasma Cells and Disease Activity in Patients with Systemic Lupus Erythematosus," *Arthritis Rheum.*, 2003, 48(5):1332-1342.
Jego et al., "Plasmacytoid Dendritic Cells Induce Plasma Cell Differentiation through Type I Interferon and Interleukin 6," *Immunity*, 2003, 19:225-234.
Kaneko et al., "Circulating Levels of (β-chemokines in Systemic Lupus Erythematosus," *J. Rheumatol.*, 1999, 26(3):568-573.
Kennerdell and Carthew, "Use of dsRNA-mediated genetic interference to demonstrate that frizzled and frizzled 2 act in the wingless pathway," *Cell*, 1998, 95:1017-1026.
Kirou et al., "Coordinate overexpression of interferon-alpha-induced genes in systemic lupus erythematosus," *Arthritis Rheum.*, 2004, 50:3958-3967.
Lau et al., "Further evidence of increased polymorphonuclear cell activity in patients with Raynaud's phenomenon," *Br. J. Rheumatol.*, 1992, 31:375-380.
Lee et al., "Recruitment of Foxp3+ T regulatory cells mediating allograft tolerance depends on the CCR4 chemokine receptor," *J. Exp. Med.*, 2005, 201(7):1037-1044.
Levi et al., "ICSBP/IRF-8 transactivation: a tale of protein-protein interaction," *J. Interferon. Cytokine Res.*, 2002, 22:153-160.
Li et al., "Matrilysin Shedding of Syndecan-1 Regulates Chemokine Mobilization and Transepithelial Efflux of Neutrophils in Acute Lung Injury," *Cell*, 2002, 111:635-646.
Liang et al., "Reliability and validity of six systems for the clinical assessment of disease activity in systemic lupus erythematosus," *Arthritis Rheum.*, 1989, 32(9):1107-1118.

Linker-Israeli et al., "Elevated levels of endogenous IL-6 in systemic lupus erythematosus. A putative role in pathogenesis," *J. Immunol.*, 1991, 147:117-123.
Liossis et al., "Immune cell biochemical abnormalities in systemic lupus erythematosus," *Clin. Exp. Rheumatol.*, 1997, 15:677-684.
Lit et al., "Raised plasma concentration and ex vivo production of inflammatory chemokines in patients with systemic lupus erythematosus," *Ann. Rheum. Dis.*, 2006, 65:209-215.
Liu et al., "Comparison of differentially expressed genes in T lymphocytes between autoimmune disease and murine models of autoimmune disease," *Clinical Immunology*, 2004, 112:225-230.
Lohmueller et al., "Meta-analysis of genetic association studies supports a contribution of common variants to susceptibility to common disease," *Nat. Genet.*, 2003, 33:177-182.
Lövgren et al., "Induction of Interferon-α Production in Plasmacytoid Dendritic Cells by Immune Complexes Containing Nucleic Acid Released by Necrotic or Late Apoptotic Cells and Lupus IgG," *Arthritis Rheum.*, 2004, 50(6):1861-1872.
Mancl et al., "Two discrete promoters regulate the alternatively spliced human interferon regulatory factor-5 isoforms. Multiple isoforms with distinct cell type-specific expression, localization, regulation, and function," *J. Biol. Chem.*, 2005, 280:21078-21090.
Martin et al., "A test for linkage and association in general pedigrees: the pedigree disequilibrium test," *Am. J. Hum. Genet.*, 2000, 67:146-154.
Meller et al., "Ultraviolet Radiation-Induced Injury, Chemokines, and Leukocyte Recruitment. An Amplification Cycle Triggering Cutaneous Lupus Erythematosus," *Arthritis Rheum.*, 2005, 52(5):1504-1516.
Middleton et al., "Transcytosis and Surface Presentation of IL-8 by Venular Endothelial Cells," *Cell*, 1997, 91:385-395.
Misquitta and Paterson, "Targeted disruption of gene function in *Drosophila* by RNA interference (RNA-i): a role for nautilus in embryonic somatic muscle formation," *Proc. Natl. Acad. Sci. USA*, 1999, 96:1451-1456.
Mitchell et al., "The New York Cancer Project: rationale, organization, design, and baseline characteristics," *J. Urban Health*, 2004, 81:301-310.
Molon et al., "T cell costimulation by chemokine receptors," *Nat. Immunol.*, 2005, 6(5):465-471.
Morley et al., "Genetic analysis of genome-wide variation in human gene expression," *Nature*, 2004, 430:743-747.
Myakishev et al., "High-throughput SNP genotyping by allele-specific PCR with universal energy-transfer-labeled primers," *Genome*, 2001, 11(1):163-169.
Narumi et al., "Serum levels of IFN-inducible protein-10 relating to the activity of systemic lupus erythematosus," *Cytokine*, 2000, 12(10):1561-1565.
Noris et al., "Monocyte Chemoattractant Protein-1 is Excreted in Excessive Amounts in the Urine of Patients with Lupus Nephritis," *Lab. Invest.*, 1995, 73(6):804-809.
Parsa et al., "Association of angiotensin-converting enzyme polymorphisms with systemic lupus erythematosus and nephritis: analysis of 644 SLE families," *Genes Immunol.*, 2002, 3 Suppl. 1:S42-S46.
Pascual et al., "The central role of dendritic cells and interferon-α in SLE," *Curr. Opin. Rheumatol.*, 2003, 15:548-556
Perl et al., "Mitochondrial hyperpolarization: a checkpoint of T-cell life, death and autoimmunity," Trends Immunol., 2004, 25(7):360-367.
Perlee et al., "Development and standardization of multiplexed antibody microarrays for use in quantitative proteomics," *Proteome Sci.*, 2004, 2:9-30.
Petri et al., "Definition, incidence, and clinical description of flare in systemic lupus erythematosus. A prospective cohort study," *Arthritis Rheum.*, 1991, 34(8):937-944.
Petri, "Hopkins Lupus Cohort. 1999 update," *Rheum. Dis. Clin. North Am.*, 2000, 26(2):199-213.
Prince et al., "Robust and accurate single nucleotide polymorphism genotyping by dynamic allele-specific hybridization (DASH): design criteria and assay validation," *Genome Res.*, 2001, 11:152-162.
Rainen et al., "Stabilization of mRNA Expression in Whole Blood Samples," *Clin. Chem.*, 2002, 48(11):1883-1890.

Rascu et al., "Clinical Relevance of Fcγ Receptor Polymorphisms," *Ann. N.Y. Acad. Sci.*, 1997, 815:282-295.

Reimold et al., "Plasma cell differentiation requires the transcription factor XBP-1," *Nature*, 2001, 412:300-307.

Richards et al., "Interferon-γ is required for lupus nephritis in mice treated with the hydrocarbon oil pristane," *Kidney Int.*, 2001, 60:2173-2180.

Romano and Masino, "Quelling: transient inactivation of gene expression in *Neurospora crassa* by transformation with homologous sequences," *Mol. Microbiol.*, 1992, 6:3343-3353.

Rönnblom and Alm, "A pivotal role for the natural interferon alpha-producing cells (plasmacytoid dendritic cells) in the pathogenesis of lupus," *J. Exp. Med.*, 2001, 194:F59-63.

Rönnblom et al., "Autoimmune phenomena in patients with malignant carcinoid tumors during interferon-α treatment," *Acta Oncol.*, 1991, 30(4):537-540.

Rosenberg et al., "Genetic structure of human populations," *Science*, 2002, 298:2381-2385.

Rovin et al., "Urine Chemokines as Biomarkers of Human Systemic Lupus Erythematosus Activity," *J. Am. Soc. Nephrol.*, 2005, 16:467-473.

Rozzo et al., "Evidence for an Interferon-Inducible Gene, Ifi202, in the Susceptibility to Systemic Lupus," *Immunity*, 2001, 15:435-443.

Sabeti et al., "Detecting recent positive selection in the human genome from haplotype structure," *Nature*, 2002, 419:832-837.

Santiago-Raber et al., "Type-I Interferon Receptor Deficiency Reduces Lupus-like Disease in NZB Mice," *J. Exp. Med.*, 2003, 197(6):777-788.

Saraste, "Oxidative Phosphorylation at the *fin de siècle*," *Science*, 1999, 283:1488-1493.

Schafer et al., "DNA variation and the future of human genetics," *Nat. Biotechnol.*, 1998, 15:33-39.

Schoenemeyer et al., "The interferon regulatory factor, IRF5, is a central mediator of toll-like receptor 7 signaling," *J. Biol. Chem.*, 2005, 280:17005-17012.

Schur, "Genetics of systemic lupus erythematosus," *Lupus*, 1995, 4:425-437.

Seery et al., "Antinuclear Autoantibodies and Lupus Nephritis in Transgenic Mice Expressing Interferon γ in the Epidermis," *J. Exp. Med.*, 1997, 186(9):1451-1459.

Shaffer et al., "Blimp-1 Orchestrates Plasma Cell Differentiation by Extinguishing the Mature B Cell Gene Expression Program," *Immunity*, 2002, 17:51-62.

Shaffer et al., "XBP1, Downstream of Blimp-1, Expands the Secretory Apparatus and Other Organelles, and Increases Protein Synthesis in Plasma Cell Differentiation," *Immunity*, 2004, 21:81-93.

Shao et al., "Optimization of Rolling-Circle Amplified Protein Microarrays for Multiplexed Protein Profiling," *J. Biomed. Biotechnol.*, 2003, 5:299-307.

Shi et al., "Lymphoid Chemokine B cell-Attracting Chemokine-1 (CXCL13) Is Expressed in Germinal Center of Ectopic Lymphoid Follicles Within the Synovium of Chronic Arthritis Patients," *J. Immunol.*, 2001, 166:650-655.

Shoenfeld et al., "Effect of Physical Effort on the White Blood Cells in Benign Familial Leukopenia," *Acta Haematol.*, 1981, 65:108-113.

Sigurdsson et al., "Polymorphisms in the tyrosine kinase 2 and interferon regulatory factor 5 genes are associated with systemic lupus erythematosus," *Am. J. Hum. Genet.*, 2005, 76:528-537.

Slide Presentation presented at SLE: Targets for New Therapeutics—A Scientific Conference, Salmon et al. (organizers), Jan. 10-12, 2002, Hyatt Regency Bethesda, Bethesda, Maryland.

Stoneking et al., "Population variation of human mtDNA control region sequences detected by enzymatic amplification and sequence-specific oligonucleotide probes," *Am. J. Hum. Genet.*, 1991, 48:370-382.

Summerton and Weller, "Morpholino antisense oligomers: design, preparation, and properties," *Antisense Nucleic Acid Drug Dev.*, 1997, 7:187-195.

Svenungsson et al., "Elevated triglycerides and low levels of high-density lipoprotein as markers of disease activity in association with up-regulation of the tumor necrosis factor alpha/tumor necrosis factor receptor system in systemic lupus erythematosus," *Arthritis Rheum.*, 2003, 48:2533-2540.

Takaoka et al., "Integral role of IRF-5 in the gene induction programme activated by Toll-like receptors," *Nature*, 2005, 434:243-249.

Tan and Arnett, "Genetic factors in the etiology of systemic sclerosis and Raynaud phenomenon," *Curr. Opin. Rheumatol.*, 2000, 12:511-519.

Tan et al., "The 1982 revised criteria for the classification of systemic lupus erythematosus," *Arthritis Rheum.*, 1982, 25:1271-1277.

Theofilopoulos et al., "Type I interferons (α/β) in immunity and autoimmunity," *Annu. Rev. Immunol.*, 2005, 23:307-336

Underhill et al., "Detection of numerous Y chromosome biallelic polymorphisms by denaturing high-performance liquid chromatography," *Genome Res.*, 1997, 7:996-1005.

Vallin et al., "Patients with systemic lupus erythematosus (SLE) have a circulating inducer of interferon-alpha (IFN-α) production acting on leucocytes resembling immature dendritic cells," *Clin. Exp. Immunol.*, 1999, 115:196-202.

Vyse and Kotzin, "Genetic basis of systemic lupus erythematosus," *Curr. Opin. Immunol.*, 1996, 8:843-851.

Wada et al., "Detection of urinary interleukin-8 in glomerular diseases," *Kidney Int.*, 1994, 46:455-460.

Wada et al., "Monitoring urinary levels of monocyte chemotactic and activating factor reflects disease activity of lupus nephritis," *Kidney Int.*, 1996, 49:761-767.

Wakeland et al., "Delineating the Genetic Basis of Systemic Lupus Erythematosus," *Immunity*, 2001, 15:397-408.

Wallace, "The Clinical Presentation of Systemic Lupus Erythematosus," Wallace and Hahn, editors, Dubois' Lupus Erythematosus, 1997, 5th ed., Baltimore, Williams & Wilkins. pp. 627-633.

Walsh et al., "Searching for signals of evolutionary selection in 168 genes related to immune function," *Hum. Genet.*, 2006, 119:92-102.

Wang et al., "Identification of RANTES Receptors on Human Monocytic Cells: Competition for Binding and Desensitization by Homologous Chemotactic Cytokines," *J. Exp. Med.*, 1993, 177:699-705.

Wenzel et al., "Enhanced type I interferon signalling promotes Th1-biased inflammation in cutaneous lupus erythematosus," *J. Pathol.*, 2005, 205:435-442.

Wenzel et al., "Role of the Chemokine Receptor CCR4 and its Ligand Thymus- and Activation-Regulated Chemokine/CCL17 for Lymphocyte Recruitment in Cutaneous Lupus Erythematosus," *J. Invest. Dermatol.*, 2005, 124:1241-1248.

Wolf and Brelsford, "Soluble interleukin-2 receptors in systemic lupus erythematosus," *Arthritis Rheum.*, 1988, 31(6):729-735.

Wong et al., "Elevation of plasma interleukin-18 concentration is correlated with disease activity in systemic lupus erythematosus," *Rheumatology*, 2000, 39:1078-1081.

Woolson and Bean, "Mantel-Haenszel statistics and direct standardization," *Stat. Med.*, 1982, 1:37-39.

Yajima et al., "Elevated Levels of Soluble Fractalkine in Active Systemic Lupus Erythematosus. Potential Involvement in Neuropsychiatric Manifestations," *Arthritis Rheum.*, 2005, 52(6):1670-1675.

Yamada et al., "Selective Accumulation of CCR4+ T Lymphocytes Into Renal Tissue of Patients With Lupus Nephritis," *Arthritis Rheum.*, 2002, 46(3):735-740.

Zhu et al., "Suppression of Autoimmune Neuritis in IFN-γ Receptor-Deficient Mice," *Exp. Neurol.*, 2001, 169:472-478.

Zlotnik and Yoshie, "Chemokines: A New Classification System and Their Role in Immunity," *Immunity*, 2000, 12:121-127.

\* cited by examiner

FIGURE 4

| | | | | | elevated | |
|---|---|---|---|---|---|---|
| rs729302 | rs2004640 | rs752637 | rs2280714 | exon-1B isoforms | IRF-5 mRNA levels | SLE risk |
| A (68.3%) | T C T (50.0%) | | | YES | YES | YES |
| C (31.7%) | G T C (39.9%) | | | NO | NO | NO |
| | G C T (5.0%) | | | NO | YES | NO |
| | G T T (3.3%) | | | NO | YES | NO |

FIGURE 13

| IRF5 haplotype | Exon 1B transcripts | Exon 6 insertion | High expression | mRNA isoforms | Risk to SLE |
|---|---|---|---|---|---|
| 1 | + | + | + | Iso1/Iso2 | ++ |
| 2 | + | - | + | Iso3/Iso4 | |
| 3 | + | + | - | Iso1/Iso2 | |
| 4 | - | + | - | - | - |
| 5 | - | - | + | - | - |

IRF-5 HAPLOTYPES IN SYSTEMIC LUPUS ERYTHEMATOSUS

CROSS-REFERENCE TO RELATED APPLICATIONS

This application is a continuation of U.S. application Ser. No. 11/694,272, filed Mar. 30, 2007, now abandoned.

STATEMENT AS TO FEDERALLY SPONSORED RESEARCH

Funding for the work described herein was provided in part by the National Institutes of Health, grant numbers AI 63274-01 and AR 43274-10. The federal government has certain rights in the invention.

TECHNICAL FIELD

This document relates to materials and methods for diagnosing or predicting risk of systemic lupus erythematosus.

BACKGROUND

Systemic lupus erythematosus (SLE) is a chronic, inflammatory autoimmune disease characterized by antinuclear autoantibodies and deposition of immune complexes, leading to organ damage and early death (Alarcon-Segovia et al. (2005) *Arthritis Rheum.* 52:1138-1147). SLE autoantibodies mediate organ damage by directly binding to host tissues and by forming immune complexes that deposit in vascular tissues and activate immune cells. Organs targeted in SLE include the skin, kidneys, vasculature, joints, various blood elements, and the central nervous system (CNS). The severity of disease, the spectrum of clinical involvement, and the response to therapy vary widely among patients.

The type I interferon (IFN) pathway is activated in human SLE (Blanco et al. (2001) *Science* 294:1540-1543; Ronnblom and Alm (2001) *J. Exp. Med.* 194:F59-63; Baechler et al. (2003) *Proc. Natl. Acad. Sci. USA* 100:2610-2615). Type I IFN is a central mediator of viral immunity (Isaacs and Lindenmann (1957) *Proc. R. Soc. B* 147:258-273), and many SLE patients strongly overexpress IFN-responsive genes in blood cells (Baechler et al. supra; Bennett et al. (2003) *J. Exp. Med.* 197:711-723; Kirou et al. (2004) *Arthritis Rheum.* 50:3958-3967). However, it is not known whether the IFN expression signature is a general biomarker of a dysregulated immune system, or rather reflects primary genetic variation causal to the pathogenesis of human SLE.

IFN regulatory factor 5 (IRF-5) is a member of a family of transcription factors that controls inflammatory and immune responses (Honda et al. (2005) *Int. Immunol.* 17:1367-1378). IRF-5 has a critical role in the production of the pro-inflammatory cytokines tumor necrosis factor-α (TNF-α), interleukin-12 (IL-12), and IL-6 following toll-like receptor (TLR) signaling as determined by knockout mouse studies (Takaoka et al. (2005) *Nature* 434:243-249), and is also important for transactivation of type I IFN and IFN-responsive genes (Barnes et al. (2001) *J. Biol. Chem.* 276:23382-23390; Barnes et al. (2004) *J. Biol. Chem.* 279:45194-45207).

The clinical heterogeneity of SLE makes it challenging to diagnose and manage this disease. Moreover, current therapy options for SLE are limited, and therapy strategies are highly individualized and tend to include much trial and error. Thus, there is a need for diagnostic technologies for SLE that can identify patients that will likely respond well to particular therapies.

SUMMARY

This document is based in part on the discovery that several IRF-5 single nucleotide polymorphisms (SNPs) are associated with SLE. For example, the results provided herein demonstrate that the IRF-5 rs2004640 T allele, rs2880714 T allele, rs2070197 C allele, rs10954213 A allele, and exon 6 insertion allele are associated with SLE. The results also demonstrate that the rs2004640 T allele creates a 5' donor splice site in an alternate exon 1 of IRF-5 (exon-1B), and that only individuals with the donor splice site express IRF-5 isoforms initiated at exon-1B. In addition, the results show that rs2880714, an independent cis-acting variant that drives elevated expression of IRF-5 transcripts, is strongly linked to the exon-1B splice donor site. Further, the results presented herein demonstrate that the rs10954213 A allele results in a "short form" IRF-5 mRNA and a truncated 3' untranslated region (UTR). This allele also is associated with elevated levels of IRF-5 expression. Haplotypes with elevated IRF-5 expression in the absence of the exon-1B donor site, however, do not confer risk to SLE. Further, a germline polymorphism has been discovered that results in a 30 nucleotide insertion in exon 6 of IRF-5, and have observed that this insertion also is associated with SLE. An IRF-5 haplotype that drives elevated expression of multiple unique isoforms of IRF-5 can be an important genetic risk factor for SLE, proving a causal role of type I IFN pathway genes in human autoimmune disease.

In one aspect, this document features a method for assessing the predisposition of a mammal to develop systemic lupus erythematosus (SLE), comprising: (a) determining whether or not the mammal has an IRF-5 haplotype comprising an rs2004640 T allele, an IRF-5 exon 6 insertion allele, and an rs10954213 A allele; and (b) classifying the mammal as being susceptible to develop SLE if the mammal has the IRF-5 haplotype, or classifying the mammal as not being susceptible to develop SLE if the mammal does not contain the IRF-5 haplotype. The mammal can be a human. The method can further include determining whether a biological sample from the mammal contains elevated levels of interferon-α (IFN-α), interleukin-1 receptor antagonist (IL-1RA), interleukin-6 (IL-6), monocyte chemoattractant protein-1 (MCP-1), macrophage inflammatory protein-1α (MIP-1α), macrophage inflammatory protein-1β (MIP-1β), or tumor necrosis factor-α (TNF-α).

In another aspect, this document features a method for diagnosing SLE in a mammal, comprising: (a) determining whether or not the mammal has an IRF-5 haplotype comprising an rs2004640 T allele, an IRF-5 exon 6 insertion allele, and an rs10954213 A allele; and (b) classifying the mammal as being susceptible to develop SLE if the mammal has the IRF-5 haplotype, or classifying the mammal as not being susceptible to develop SLE if the mammal does not have the IRF-5 haplotype. The mammal can be a human. The method can further include determining whether a biological sample from the mammal contains elevated levels of IFN-α, IL-1RA, IL-6, MCP-1, MIP-1α, MIP-1β, or TNF-α.

In another aspect, this document features a method for assessing the predisposition of a mammal to develop SLE, comprising: (a) determining whether or not the mammal has an IRF-5 haplotype comprising an rs2004640 T allele, an IRF-5 exon 6 insertion allele, an rs10954213 A allele, and an rs2070197 C allele; and (b) classifying the mammal as being susceptible to develop SLE if the mammal has the IRF-5 haplotype, or classifying the mammal as not being susceptible to develop SLE if the mammal does not have the IRF-5 haplotype. The mammal can be a human. The method can further include determining whether a biological sample from the mammal contains elevated levels of interferon-α (IFN-α), interleukin-1 receptor antagonist (IL-1RA), interleukin-6 (IL-6), monocyte chemoattractant protein-1 (MCP-1), macrophage inflammatory protein-1α (MIP-1α), macrophage inflammatory protein-1β (MIP-1β), or tumor necrosis factor-α (TNF-α).

In another aspect, this document features a method for diagnosing SLE in a mammal, comprising: (a) determining whether or not the mammal has an IRF-5 haplotype comprising an rs2004640 T allele, an IRF-5 exon 6 insertion allele, an rs10954213 A allele, and an rs2070197 C allele; and (b) classifying the mammal as being susceptible to develop SLE if the mammal has the IRF-5 haplotype, or classifying the mammal as not being susceptible to develop SLE if the mammal does not have the IRF-5 haplotype. The mammal can be a human. The method can further include determining whether a biological sample from the mammal contains elevated levels of IFN-α, IL-1RA, IL-6, MCP-1, MIP-1α, MIP-1β, or TNF-α.

In another aspect, this document features a method for assessing the predisposition of a mammal to develop SLE, comprising: (a) determining whether or not the mammal comprises cells containing a level of an IRF-5 polypeptide that is greater than an average level of an IRF-5 polypeptide in control cells from one or more control mammals, wherein the mammal and the one or more control mammals are from the same species, and wherein the IRF-5 polypeptide in the mammal comprises an amino acid sequence encoded by exon 1B and an amino acid sequence encoded by an insertion in exon 6; and (b) classifying the mammal as being susceptible to develop SLE if the mammal contains the cells, or classifying the mammal as not being susceptible to develop SLE if the mammal does not contain the cells. The mammal can be a human. The one or more control mammals can be healthy humans. The cells and the control cells can be peripheral blood mononuclear cells or whole blood cells. The level of IRF-5 polypeptide in the mammal can be greater than the average level of IRF-5 polypeptide in control cells from at least 10 control mammals, or greater than the average level of IRF-5 polypeptide in control cells from at least 20 control mammals. The determining step can include measuring the level of IRF-5 mRNA encoding the IRF-5 polypeptide, or measuring the level of IRF-5 polypeptide. The method can further include determining whether a biological sample from the mammal contains elevated levels of IFN-α, IL-1RA, IL-6, MCP-1, MIP-1α, MIP-1β, or TNF-α.

In another aspect, this document features a method for diagnosing SLE in a mammal, comprising: (a) determining whether or not the mammal comprises cells containing a level of an IRF-5 polypeptide that is greater than an average level of an IRF-5 polypeptide in control cells from one or more control mammals, wherein the mammal and the one or more control mammals are from the same species, and wherein the IRF-5 polypeptide in the mammal comprises an amino acid sequence encoded by exon 1B and an amino acid sequence encoded by an insertion in exon 6; and (b) classifying the mammal as being susceptible to develop SLE if the mammal contains the cells, or classifying the mammal as not being susceptible to develop SLE if the mammal does not contain the cells. The mammal can be a human. The one or more control mammals can be healthy humans. The cells and the control cells can be peripheral blood mononuclear cells or whole blood cells. The level of IRF-5 polypeptide in the mammal can be greater than the average level of IRF-5 polypeptide in control cells from at least 10 control mammals, or greater than the average level of IRF-5 polypeptide in control cells from at least 20 control mammals. The determining step can include measuring the level of IRF-5 mRNA encoding the IRF-5 polypeptide, or measuring the level of IRF-5 polypeptide. The method can further include determining whether a biological sample from the mammal contains elevated levels of IFN-α, IL-1RA, IL-6, MCP-1, MIP-1α, MIP-1β, or TNF-α.

In yet another aspect, this document features a method for determining the likelihood of a mammal to respond to treatment with a therapy directed to IRF-5, comprising: (a) determining whether or not the mammal has an IRF-5 haplotype comprising an rs2004640 T allele, an IRF-5 exon 6 insertion allele, and an rs10954213 A allele; and (b) classifying the mammal as likely to respond to the therapy if the mammal has the IRF-5 haplotype, or classifying the mammal as not being likely to respond to the therapy if the mammal does not have the IRF-5 haplotype. The mammal can be a human. The mammal can be diagnosed as having SLE. A response to the therapy can include a reduction in one or more symptoms of SLE. The method can further include determining whether a biological sample from the mammal contains elevated levels of IFN-α, IL-1RA, IL-6, MCP-1, MIP-1α, MIP-1β, or TNF-α.

In still another aspect, this document features a method for determining the likelihood of a mammal to respond to treatment with a therapy directed to IRF-5, comprising: (a) determining whether or not the mammal comprises cells containing a level of an IRF-5 polypeptide that is greater than an average level of an IRF-5 polypeptide in control cells from one or more control mammals, wherein the mammal and the one or more control mammals are from the same species, and wherein the IRF-5 polypeptide in the mammal comprises an amino acid sequence encoded by exon 1B and an amino acid sequence encoded by an insertion in exon 6; and (b) classifying the mammal as likely to respond to the therapy if the mammal contains the cells, or classifying the mammal as not being likely to respond to the therapy if the mammal does not contain the cells. The mammal can be a human. The mammal can be diagnosed as having SLE. The one or more control mammals can be healthy humans. The cells and the control cells can be peripheral blood mononuclear cells or whole blood cells. The level of IRF-5 polypeptide in the mammal can be greater than the average level of IRF-5 polypeptide in control cells from at least 10 control mammals, or greater than the average level of IRF-5 polypeptide in control cells from at least 20 control mammals. The determining step can include measuring the level of IRF-5 mRNA encoding the IRF-5 polypeptide, or measuring the level of IRF-5 polypeptide. A response to the therapy can include a reduction in one or more symptoms of SLE. The method can further include determining whether a biological sample from the mammal contains elevated levels of IFN-α, IL-1RA, IL-6, MCP-1, MIP-1α, MIP-1β, or TNF-α. The method can include determining whether or not the mammal contains detectable levels of an IRF-5 mRNA having a truncated 3' untranslated region.

In another aspect, this document features a method for determining the likelihood of a mammal to respond to treatment with a therapy directed to a cytokine or a Toll like receptor (TLR), comprising: (a) determining whether or not the mammal has an IRF-5 haplotype comprising an rs2004640 T allele, an IRF-5 exon 6 insertion allele, and an rs10954213 A allele; and (b) classifying the mammal as likely to respond to the treatment if the mammal has the IRF-5 haplotype, or classifying the mammal as not being likely to respond to the treatment if the mammal does not have the IRF-5 haplotype. The cytokine can be IFN-α, IL-1RA, IL-6, MCP-1, MIP-1α, MIP-1β, or TNF-α. The TLR can be TLR7, TLR8, or TLR9. The mammal can be a human. The method can further include determining whether a biological sample from the mammal contains elevated levels of IFN-α, IL-1RA, IL-6, MCP-1, MIP-1α, MIP-1β, or TNF-α.

In yet another aspect, this document features a method for determining the likelihood of a mammal to respond to treatment with a therapy directed to a cytokine or a TLR, comprising: (a) determining whether or not the mammal comprises cells containing a level of an IRF-5 polypeptide that is greater than an average level of an IRF-5 polypeptide in control cells from one or more control mammals, wherein the mammal and the one or more control mammals are from the same species, and wherein the IRF-5 polypeptide in the mammal comprises an amino acid sequence encoded by exon 1B and an amino acid sequence encoded by an insertion in exon 6; and (b) classifying the mammal as likely to respond to the treatment if the mammal contains the cells, or classifying the mammal as not being likely to respond to the treatment if the mammal does not contain the cells. The cytokine can be IFN-α, IL-1RA, IL-6, MCP-1, MIP-1α, MIP-1β, or TNF-α. The TLR can be TLR7, TLR8, or TLR9. The mammal can be a human. The one or more control mammals can be healthy humans. The cells and the control cells can be peripheral blood mononuclear cells or whole blood cells. The level of IRF-5 polypeptide in the mammal can be greater than the average level of IRF-5 polypeptide in control cells from at least 10 control mammals, or greater than the average level of IRF-5 polypeptide in control cells from at least 20 control mammals. The determining step can include measuring the level of IRF-5 mRNA encoding the IRF-5 polypeptide, or measuring the level of IRF-5 polypeptide. The method can further include determining whether a biological sample from the mammal contains elevated levels of IFN-α, IL-1RA, IL-6, MCP-1, MIP-1α, MIP-1β, or TNF-α.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 3a) and in PBMCs (N=41; FIG. 3b) in two sets of independent SLE cases. Total IRF-5 levels were compared by rs2280714 genotype in whole blood SLE samples: TT vs. TC, P=0.01; TC vs. CC, P=0.0006; TT vs. CC, P=0.000002. A similar analysis was performed for the SLE PBMC samples: TT vs. TC, P=NS; TC vs. CC, P=0.0004; TT vs. CC, P=0.000006.

FIG. 4 is a depiction of the SLE risk haplotype, showing both the rs2004640 T allele (green) and the rs2280714 T allele (blue). Haplotype frequencies of CEPH founders, as determined by Haploview, are shown. rs729302 is located 5' of the haplotype marked by rs2004640, rs752637, and rs2280714.

FIG. 13 is a summary of IRF5 haplotypes and their association to SLE.

DETAILED DESCRIPTION

Figure 1:
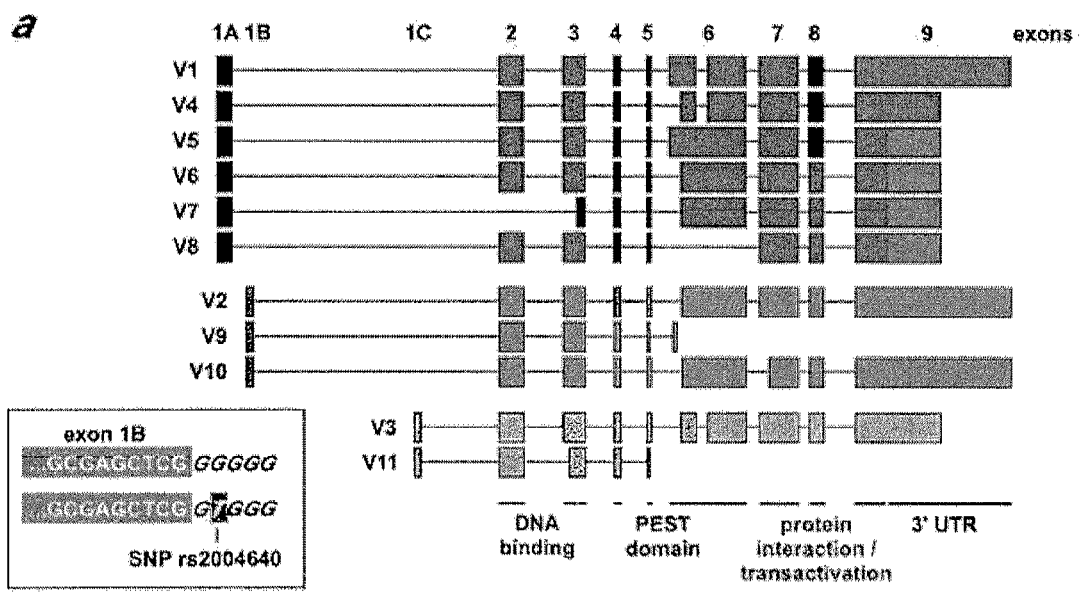
FIG. 1a depicts the mRNA isoforms of IRF-5. Three sets of isoforms derive from three alternative promoters in the IRF-5 5' region. The locations of the exons encoding DNA binding, PEST, and protein interaction domains, as well as the 3' UTR, are annotated. Protein translation begins at a consensus ATG that is 10 bp from the 5' end of exon 2. The location of the rs2004640 SNP, 2 bp downstream of exon-1B, is shown in the box [wild type sequence (top), SEQ ID NO:251; variant sequence (bottom), SEQ ID NO:252]. Two polyadenylation sites are present in the IRF-5 3' UTR, and the lengths of the 3' UTRs for V5, V6, V7 and V8 are unknown. The exon/intron structures are not shown to scale.
FIG. 1b is a series of graphs summarizing the data from TaqMan real-time quantitative RT-PCR analysis for exon-1A, -1B, and -1C associated transcripts. Each bar represents the mean±SEM of expression levels (N=8 SLE cases for each genotype; similar data was obtained for normal controls). Delta Cts were calculated from duplicate samples normalized to human β2-microglobulin, and converted to linear fold-differences.
Figure 1:
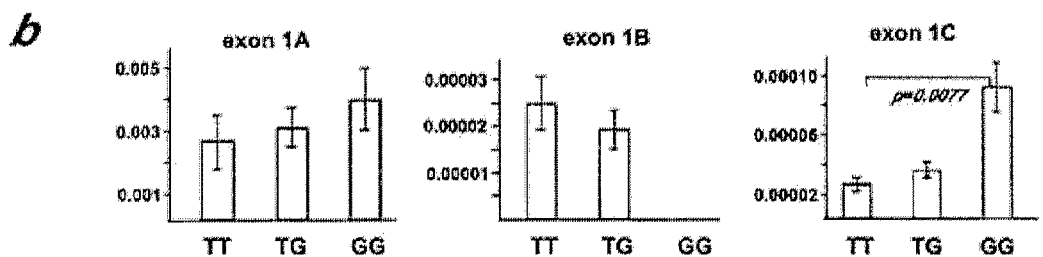

This document relates to methods and materials involved in diagnosing SLE in a mammal, assessing a mammal's susceptibility to develop SLE, and determining whether a mammal is likely to respond to therapy directed toward IRF-5. For example, this document relates to materials and methods for determining whether a mammal contains one or more IRF-5 variants, contains an IRF-5 mRNA that results from alternative splicing or alternative polyadenylation due to the presence of one or more IRF-5 variants, or for determining whether a mammal contains cells in which IRF-5 is expressed at level that is more or less than the average level of IRF-5 expression observed in control cells obtained from control mammals. In some embodiments, for example, a mammal can be diagnosed as having or being at risk of developing SLE if it is determined that the mammal contains one or more IRF-5 variants (e.g., an rs2004640 T allele, an rs2280714 T allele, an rs2070197 C allele, an rs10954213 A allele, and/or an exon 6 insertion allele).

In some embodiments, a mammal can be diagnosed as having or being at risk of developing SLE if it is determined that the mammal contains an IRF-5 mRNA comprising exon-1B, a truncated 3' UTR, and/or an exon 6 insertion, as described herein. In some cases, a mammal can be diagnosed as having or being at risk for SLE if it is determined that the mammal contains cells that express a level of IRF-5 mRNA containing exon-1B and/or a truncated 3' UTR and/or an exon 6 insertion that is greater than the level of an IRF-5 mRNA expressed in control cells from control mammals. In still other embodiments, a mammal can be diagnosed as having or being at risk of developing SLE if it is determined that the mammal contains cells having a level of IRF-5 polypeptide that is higher than the average level of IRF-5 polypeptide in control cells obtained from control mammals.

The mammal can be any mammal such as a human, dog, mouse, or rat. Nucleic acids or polypeptides from any cell type can be isolated and evaluated. For example, whole blood cells, peripheral blood mononuclear cells (PMBC), total white blood cells, lymph node cells, spleen cells, or tonsil cells can be isolated from a human patient and evaluated to determine if that patient contains one or more IRF-5 variants (e.g., an rs2004640 T allele, an rs2280714 T allele, an rs10954213 A allele, or rs2070197 C allele), an IRF-5 mRNA containing exon-1B and/or a truncated 3' UTR and/or an exon 6 insertion, or cells that express IRF-5 at a level that is greater or less than the average level of expression observed in control cells.

As used herein, "IRF-5 variant" and "IRF-5 nucleotide sequence variant" refer to any alteration in an IRF-5 reference sequence. IRF-5 variants include variations that occur in coding and non-coding regions, including exons, introns, and untranslated sequences. As used herein, "untranslated sequence" includes 5' and 3' flanking regions that are outside of the messenger RNA (mRNA) as well as 5' and 3' untranslated regions (5'-UTR or 3'-UTR) that are part of the mRNA, but are not translated. Nucleotides are referred to herein by the standard one-letter designation (A, C, G, or T).

In some embodiments, an IRF-5 nucleotide sequence variant results in an IRF-5 mRNA having an altered nucleotide sequence (e.g., a splice variant that includes exon 1B and/or a variant that includes additional nucleotides in exon 6), or an IRF-5 polypeptide having an altered amino acid sequence (e.g., a polypeptide including a sequence encoded by exon 1B and/or a sequence encoded by an insertion in exon 6). The term "polypeptide" refers to a chain of at least four amino acid residues (e.g., 4-8, 9-12, 13-15, 16-18, 19-21, 22-50, 51-75, 76-100, 101-125 residues, or a full-length IRF-5 polypeptide). IRF-5 polypeptides may or may not have activity, or may have altered activity relative to a reference IRF-5 polypeptide. In some embodiments, polypeptides having an altered amino acid sequence can be useful for diagnostic purposes (e.g., for producing antibodies having specific binding affinity for variant IRF-5 polypeptides).

The presence or absence of IRF-5 nucleotide sequence variants can be determined using any suitable method, including methods that are standard in the art, for example. nucleotide sequence variants can be detected, for example, by sequencing exons, introns, 5' untranslated sequences, or 3' untranslated sequences, by performing allele-specific hybridization, allele-specific restriction digests, mutation specific polymerase chain reactions (MSPCR), by single-stranded conformational polymorphism (SSCP) detection (Schafer et al. (1995) *Nat. Biotechnol.* 15:33-39), denaturing high performance liquid chromatography (DHPLC, Underhill et al. (1997) *Genome Res.* 7:996-1005), primer extension of multiplex products (e.g., as described herein), infrared matrix-assisted laser desorption/ionization (IR-MALDI) mass spectrometry (WO 99/57318), and combinations of such methods.

Genomic DNA generally is used in the analysis of IRF-5 nucleotide sequence variants, although mRNA also can be used. Genomic DNA is typically extracted from a biological sample such as a peripheral blood sample, but can be extracted from other biological samples, including tissues (e.g., mucosal scrapings of the lining of the mouth or from renal or hepatic tissue). Routine methods can be used to extract genomic DNA from a blood or tissue sample, including, for example, phenol extraction. Alternatively, genomic DNA can be extracted with kits such as the QIAAMP® Tissue Kit (QIAGEN®, Chatsworth, Calif.), WIZARD® Genomic DNA purification kit (PROMEGA™) and the A.S.A.P.™ Genomic DNA isolation kit (BOEHRINGER MANNHEIM™, Indianapolis, Ind.).

Typically, an amplification step is performed before proceeding with the detection method. For example, exons or introns of the IRF-5 gene can be amplified then directly sequenced. Dye primer sequencing can be used to increase the accuracy of detecting heterozygous samples.

Allele specific hybridization also can be used to detect sequence variants, including complete haplotypes of a subject (e.g., a mammal such as a human). See, Stoneking et al. (1991) *Am. J. Hum. Genet.* 48:370-382; and Prince et al. (2001) *Genome Res.* 11:152-162. In practice, samples of DNA or RNA from one or more mammals can be amplified using pairs of primers and the resulting amplification products can be immobilized on a substrate (e.g., in discrete regions). Hybridization conditions are selected such that a nucleic acid probe can specifically bind to the sequence of interest, e.g., the variant nucleic acid sequence. Such hybridizations typically are performed under high stringency as some sequence variants include only a single nucleotide difference. As used herein, high stringency conditions include the use of low ionic strength solutions and high temperatures for washing. In particular, under high stringency conditions, nucleic acid molecules are hybridized at 42° C. in 2×SSC (0.3 M NaCl/0.03 M sodium citrate) with 0.1% sodium dodecyl sulfate (SDS) and washed in 0.1×SSC (0.015 M NaCl/0.0015 M sodium citrate), 0.1% SDS at 65° C. Hybridization conditions can be adjusted to account for unique features of the nucleic acid molecule, including length and sequence composition. Probes can be labeled (e.g., fluorescently) to facilitate detection. In some embodiments, one of the primers used in the amplification reaction is biotinylated (e.g., 5' end of reverse primer) and the resulting biotinylated amplification product is immobilized on an avidin or streptavidin coated substrate.

Allele-specific restriction digests can be performed in the following manner. For nucleotide sequence variants that introduce a restriction site, restriction digest with the particular restriction enzyme can differentiate the alleles. For sequence variants that do not alter a common restriction site, mutagenic primers can be designed that introduce a restriction site when the variant allele is present or when the wild type allele is present. A portion of an IRF-5 nucleic acid can be amplified using the mutagenic primer and a wild type primer, followed by digest with the appropriate restriction endonuclease.

Certain variants, such as insertions or deletions of one or more nucleotides, change the size of the DNA fragment encompassing the variant. The insertion or deletion of nucleotides can be assessed by amplifying the region encompassing the variant and determining the size of the amplified products in comparison with size standards. For example, a region of an IRF-5 gene can be amplified using a primer set from either side of the variant. One of the primers is typically labeled, for example, with a fluorescent moiety, to facilitate sizing. The amplified products can be electrophoresed through acrylamide gels with a set of size standards that are labeled with a fluorescent moiety that differs from the primer.

PCR conditions and primers can be developed that amplify a product only when the variant allele is present or only when the wild type allele is present (MSPCR or allele-specific PCR). For example, patient DNA and a control can be amplified separately using either a wild type primer or a primer specific for the variant allele. Each set of reactions is then examined for the presence of amplification products using standard methods to visualize the DNA. For example, the reactions can be electrophoresed through an agarose gel and the DNA visualized by staining with ethidium bromide or other DNA intercalating dye. In DNA samples from heterozygous patients, reaction products would be detected with each set of primers. Patient samples containing solely the wild type allele would have amplification products only in the reaction using the wild type primer. Similarly, patient samples containing solely the variant allele would have amplification products only in the reaction using the variant primer. Allele-specific PCR also can be performed using allele-specific primers that introduce priming sites for two universal energy-transfer-labeled primers (e.g., one primer labeled with a green dye such as fluorescein and one primer labeled with a red dye such as sulforhodamine). Amplification products can be analyzed for green and red fluorescence in a plate reader. See, Myakishev et al. (2001) *Genome* 11(1):163-169.

Mismatch cleavage methods also can be used to detect differing sequences by PCR amplification, followed by hybridization with the wild type sequence and cleavage at points of mismatch. Chemical reagents, such as carbodiimide or hydroxylamine and osmium tetroxide can be used to modify mismatched nucleotides to facilitate cleavage.

IRF-5 mRNA isoforms can be evaluated using any suitable method, including those known in the art. For example, northern blotting, slot blotting, chip hybridization techniques, or RT-PCR-based methods can be used to determine whether a mammal contains an IRF-5 mRNA that includes exon-1B or that has a truncated 3' UTR.

When IRF-5 expression is evaluated, the expression level can be greater than or less than the average level observed in control cells obtained from control mammals. Typically, IRF-5 can be classified as being expressed at a level that is greater than or less than the average level observed in control cells if the expression levels differ by at least 1-fold (e.g., 1.5-fold, 2-fold, 3-fold, or more than 3-fold). In addition, the control cells typically are the same type of cells as those isolated from the mammal being evaluated. In some cases, the control cells can be isolated from one or more mammals that are from the same species as the mammal being evaluated. When diagnosing or predicting susceptibility to SLE, the control cells can be isolated from healthy mammals such as healthy humans who do not have SLE. Any number of control mammals can be used to obtain the control cells. For example, control cells can be obtained from one or more healthy mammals (e.g., at least 5, at least 10, at least 15, at least 20, or more than 20 control mammals).

Further, any suitable method can be used to determine whether or not IRF-5 is expressed at a level that is greater or less than the average level of expression observed in control cells. For example, the level of IRF-5 expression can be measured by assessing the level of IRF-5 mRNA expression. Levels of mRNA expression can be evaluated using, without limitation, northern blotting, slot blotting, quantitative RT-PCR, or chip hybridization techniques. Methods for chip hybridization assays include, without limitation, those described in published U.S. Patent Application No. 20040033498.

The level of IRF-5 expression also can be measured by assessing polypeptide levels. Polypeptide levels can be measured using any method, including immuno-based assays (e.g., ELISA), western blotting, or silver staining.

Research has demonstrated that IRF-5 is activated by TLR7 and TLR8, and that IRF-5 is a critical mediator of TLR7 signaling (Schoenemeyer et al. (2005) *J. Biol. Chem.* 280:17005-17012). TLR7, TLR8, and TLR9 form an evolutionarily related subgroup within the TLR superfamily (Chuang and Ulevitch (2000) *Eur. Cytokine Netw.* 11:372-378; and Du et al. (2000) *Eur. Cytokine Netw.* 11:362-371). As described in the Examples herein, subjects containing an rs2004604 T allele and an rs1965213 A allele can secrete elevated levels of cytokines, and also display an enhanced response to TLR7 and IFN-α signaling as compared to subjects having an rs2004640 G allele and an rs1954213 G allele. Thus, the presence of the aforementioned IRF-5 alleles (e.g., the combination of alleles in haplotype 1 described in the Examples herein), or increased IRF-5 levels, also can be ascertained in methods to determine whether a mammal (e.g., a human) is likely to respond to a therapy directed toward IRF-5 (e.g., a therapy aimed at reducing IRF-5 levels), a therapy directed toward a TLR (e.g., TLR7, TLR8, or TLR9), or a therapy directed toward one or more cytokines (e.g., IRF-5 mediated cytokines such as IFN-α, interleukin-1 receptor antagonist (IL-1RA), IL-6, monocyte chemoattractant protein-1 (MCP-1), macrophage inflammatory protein-1α, (MIP-1α), MIP-1β, and TNF-α). In some embodiments, the mammal can be diagnosed with SLE. By "respond" is meant that one or more symptoms of SLE are reduced by any amount (e.g., reduced by 5%, 10%, 15%, 20%, 25%, 30%, 35%, 40%, 45%, 50%, 55%, 60%, 65%, 70%, 75%, 80%, 85%, 90%, 95%, or 100%). Symptoms of SLE include, for example, arthralgia/arthritis, muscle pain, avascular necrosis, and osteoporosis, pericarditis, myocarditis, endocarditis, coronary artery problems, kidney problems, pleurisy, pneumonitis, chronic diffuse interstitial lung disease, pulmonary embolism, pulmonary hypertension, liver problems, lupus headache, seizures, CNS vasculitis, psychosis, mouth/nose ulcers, malar rash, discoid rash, hair loss, photosensitivity, hives, Raynaud's phenomenon, purpura, livedo reticularis, anemia, thrombocytopenia, leukopenia, fatigue, fever, weight loss/gain, eye problems, and gastrointestinal problems.

In some embodiments, a method that includes determining whether a mammal contains an IRF-5 variant can further include determining whether cytokine levels are increased in the mammal. For example, a method provided herein can include measuring the level of an IRF-5 mediated cytokine such as IFN-α, IL-1RA, IL-6, MCP-1, MIP-1α, MIP-1β, and TNF-α. A biological sample from a mammal having an SLE risk haplotype (haplotype 1 as described herein) that is determined to have elevated levels of one or more cytokines can be a further indication that the mammal has SLE or is predisposed to develop SLE.

Any suitable method can be used to measure the level of a cytokine in a biological sample from a mammal. For example, a whole blood sample or a fraction of a blood sample (e.g., peripheral blood mononuclear cells; PMBC) from a mammal can be obtained, and the level of one or more cytokines in the sample can be determined.

When cytokine expression is evaluated, the expression level can be greater than or less than the average level observed in control cells obtained from control mammals. Typically, cytokines can be classified as being expressed at a level that is greater than or less than the average level observed in control cells if the expression levels differ by at least 1-fold (e.g., 1.5-fold, 2-fold, 3-fold, or more than 3-fold). In addition, the control cells typically are the same type of cells as those isolated from the mammal being evaluated. In some cases, the control cells can be isolated from one or more mammals that are from the same species as the mammal being evaluated. When diagnosing or predicting susceptibility to SLE, the control cells can be isolated from healthy mammals such as healthy humans who do not have SLE. Any number of control mammals can be used to obtain the control cells. For example, control cells can be obtained from one or more healthy mammals (e.g., at least 5, at least 10, at least 15, at least 20, or more than 20 control mammals).

Any suitable method can be used to determine whether or not a particular cytokine is expressed at a level that is greater or less than the average level of expression observed in control cells. As described above for IRF-5, for example, the level of expression of a cytokine such as TNF-α can be measured by assessing the level of TNF-α mRNA expression or by assessing polypeptide levels.

Agents targeted to IRF-5, TLRs, or cytokines such as those listed herein can be, for example, drug, small molecules, antibodies or antibody fragments, such as Fab' fragments, F(ab')$_2$ fragments, or scFv fragments, antisense oligonucleotides, interfering RNAs (RNAis), or combinations thereof.

Methods for producing antibodies and antibody fragments are known in the art. Chimeric antibodies and humanized antibodies made from non-human (e.g., mouse, rat, gerbil, or hamster) antibodies also may be useful. Chimeric and humanized monoclonal antibodies can be produced by recombinant DNA techniques known in the art, for example, using methods described in U.S. Pat. Nos. 4,816,567; 5,482,856; 5,565,332; 6,054,297; and 6,808,901.

Antisense oligonucleotides typically are at least 8 nucleotides in length, and hybridize to an IRF-5, TLR, or cytokine transcript. For example, a nucleic acid can be about 8, 9, 10-20 (e.g., 11, 12, 13, 14, 15, 16, 17, 18, 19, or 20 nucleotides in length), 15-20, 18-25, or 20-50 nucleotides in length. In other embodiments, antisense molecules can be used that are greater than 50 nucleotides in length. As used herein, the term "oligonucleotide" refers to an oligomer or polymer of ribonucleic acid (RNA) or deoxyribonucleic acid (DNA) or analogs thereof. Nucleic acid analogs can be modified at the base moiety, sugar moiety, or phosphate backbone to improve, for example, stability, hybridization, or solubility of a nucleic acid. Modifications at the base moiety include, without limitation, substitution of deoxyuridine for deoxythymidine, substitution of 5-methyl-2'-deoxycytidine or 5-bromo-2'-deoxycytidine for deoxycytidine, and any other suitable base substitution. Modifications of the sugar moiety can include, for example, modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered, morpholino ring, or peptide nucleic acids, in which the deoxyphosphate backbone is replaced by a pseudopeptide backbone (e.g., an aminoethylglycine backbone) and the four bases are retained. See, for example, Summerton and Weller (1997) *Antisense Nucleic Acid Drug Dev.* 7:187-195; and Hyrup et al. (1996) *Bioorgan. Med. Chem.* 4:5-23. In addition, the deoxyphosphate backbone can be replaced with, for example, a phosphorothioate or phosphorodithioate backbone, a phosphoroamidite, or an alkyl phosphotriester backbone. See, for example, U.S. Pat. Nos. 4,469,863; 5,235,033; 5,750,666; and 5,596,086 for methods of preparing oligonucleotides with modified backbones.

Methods for synthesizing antisense oligonucleotides are known in the art, including solid phase synthesis techniques. Equipment for such synthesis is commercially available from several vendors including, for example, Applied Biosystems (Foster City, Calif.). Alternatively, expression vectors that contain a regulatory element that directs production of an antisense transcript can be used to produce antisense molecules.

It is understood in the art that the sequence of an antisense oligonucleotide need not be 100% complementary to that of its target nucleic acid to be hybridizable under physiological conditions. Antisense oligonucleotides hybridize under physiological conditions when binding of the oligonucleotide to the native nucleic acid interferes with the normal function of the native nucleic acid, and non-specific binding to non-target sequences is minimal.

Target sites for antisense oligonucleotides include the regions encompassing the translation initiation or termination codon of the open reading frame (ORF) of the gene. In addition, the ORF has been targeted effectively in antisense technology, as have the 5' and 3' untranslated regions. Furthermore, antisense oligonucleotides have been successfully directed at intron regions and intron-exon junction regions. Further criteria can be applied to the design of antisense oligonucleotides. Such criteria are well known in the art, and are widely used, for example, in the design of oligonucleotide primers. These criteria include the lack of predicted secondary structure of a potential antisense oligonucleotide, an appropriate G and C nucleotide content (e.g., approximately 50%), and the absence of sequence motifs such as single nucleotide repeats (e.g., GGGG runs). The effectiveness of antisense oligonucleotides at modulating expression of a nucleic acid can be evaluated by measuring levels of the targeted mRNA or polypeptide (e.g., by Northern blotting, RT-PCR, Western blotting, ELISA, or immunohistochemical staining).

Double-stranded interfering RNA (RNAi) homologous to IRF-5 or cytokine DNA also can be used to reduce expression and consequently, activity, of IRF-5 or cytokines. See, e.g., U.S. Pat. No. 6,933,146; Fire et al. (1998) *Nature* 391:806-811; Romano and Masino (1992) *Mol. Microbiol.* 6:3343-3353; Cogoni et al. (1996) *EMBO J.* 15:3153-3163; Cogoni and Masino (1999) *Nature* 399:166-169; Misquitta and Paterson (1999) *Proc. Natl. Acad. Sci. USA* 96:1451-1456; and Kennerdell and Carthew (1998) *Cell* 95:1017-1026. Sense and anti-sense RNA strands of RNAi can be individually constructed using chemical synthesis and enzymatic ligation reactions using procedures known in the art. For example, each strand can be chemically synthesized using naturally occurring nucleotides or nucleic acid analogs. The sense or anti-sense strand also can be produced biologically using an expression vector into which a target sequence (full-length or a fragment) has been subcloned in a sense or anti-sense orientation. The sense and anti-sense RNA strands can be annealed in vitro before delivery of the dsRNA to cells. Alternatively, annealing can occur in vivo after the sense and anti-sense strands are sequentially delivered to the tumor vasculature or to tumor cells.

The invention will be further described in the following examples, which do not limit the scope of the invention described in the claims.

EXAMPLES

Example 1

A Common IRF-5 Haplotype that Regulates mRNA Splicing and Expression and is Associated with Increased Genetic Risk in Human SLE Materials and Methods Clinical Samples: A U.S. Caucasian SLE family collection of 187 sib-pair and 223 trio pedigrees was recruited at the University of Minnesota. An additional 63 trios from the NIAMS-sponsored Lupus Multiplex Registry at Oklahoma Medical Research Foundation were included in the analysis. The overall U.S. family cohort was comprised of 681 SLE cases and 824 other family members. 459 probands from the U.S. family collection, 266 cases from the Hopkins Lupus Cohort, 41 controls from Minnesota, and 1393 controls of European ancestry from the New York Health Project (Mitchell et al. (2004) *J. Urban Health* 81:301-310) collection were genotyped for the case/control analysis.

Three additional SLE case/control cohorts were studied. A cohort of 444 Spanish patients with SLE and 541 controls were collected in several clinics in the Andalucia region of Southern Spain. All individuals were of Spanish Caucasian ancestry. A second cohort of 284 patients SLE patients and 279 matched controls were collected through a multi-center collaboration in Argentina. Individuals were of Caucasian (72.5%) and mixed (20%) ancestry. Six percent were of Amerindian (n=1), Asian (n=2), or unknown ancestry (n=22). A third set of 208 ethnic Swedish patients and 254 controls from the Stockholm-Uppsala area were studied (no overlap with the previously published cases; Sigurdsson et al. (2005) *Am. J. Hum. Genet.* 76:528-537). All patients fulfilled the revised American College of Rheumatology criteria for SLE (Hochberg (1997) *Arthritis Rheum.* 40:1725). These studies were approved by the Human Subject Institutional Review Boards at each institution, and informed consent was obtained from all subjects.

Genotyping: Four polymorphisms from IRF5 (rs729302, rs2004640, rs752637, and rs2280714) were genotyped in the 470 families by primer extension of multiplex products with detection by matrix-assisted laser desorption ionization-time of flight mass spectroscopy using a Sequenom platform. Primer sequences were: rs729302 forward, 5'-AGCGGATAACAAATAGACCAGAGACCAGGG-3' (SEQ ID NO:1); rs729302 reverse, 5'-AGCGGATAACAAGTCTAAGTGAGTGGCAGG-3' (SEQ ID NO:2); rs729302 extension, 5'-ATGGGACAAGGTGAAGAC-3' (SEQ ID NO:3); rs2004640 forward, 5'-AGCGGATAACAG-GCGCTTTGGAAGTCCCAG-3' (SEQ ID NO:4); rs2004640 reverse, 5'-AGCGGATAACATGAAGACTG-GAGTAGGGCG-3' (SEQ ID NO:5); rs2004640 extension, 5'-CCCTGCTGTAGGCACCC-3' (SEQ ID NO:6); rs752637 forward, 5'-AGCGGATAACTCTAAAGGC-CCTACTTTGGG-3' (SEQ ID NO:7); rs752637 reverse, 5'-AGCGGATAACAAAGGTGCCCAGAAAGAAGC'3-(SEQ ID NO:8); rs752637 extension, 5'-CTGACCCTGG-GAGGAAGC-3' (SEQ ID NO:9); rs2280714 forward, 5'-AGCGGATAACCCATAAATTCTGACCCTGGC-3' (SEQ ID NO:10); rs2280714 reverse, 5'-AGCGGATAA-CAGGAGGAGTAAGCAAGG AAC-3' (SEQ ID NO:11); rs2280714 extension, 5'-TTCTGACCCTGGCAGGTCC-3' (SEQ ID NO:12). The average genotype completeness for the four assays was 98.3%. The genotyping consensus error rate was 0.7% (9 errors in Mendelian inheritance from 1288 parent-offspring transmissions—all errors were zeroed out). The typing of rs2280714 did not include the OMRF trios.

For the U.S. case-control studies, rs2004640 was typed by TaqMan in the Hopkins cases and in the MN and NYHP controls, and by Sequenom for all other samples. rs2004640 primers were: forward, 5'-CAGCTGCGCCTGGAAAG-3' (SEQ ID NO:13); reverse, 5'-GGGAGGCGCTTTGGAAGT-3' (SEQ ID NO:14); extension (vic), 5'-TGTAGGCAC-CCCCCCG-3' (SEQ ID NO:15); extension (fam), 5'-TG-TAGGCACCCACCCG-3' (SEQ ID NO:16). Forty individuals were genotyped on both platforms with 100% concordance of results. Genotyping of rs2004640 was performed separately for the Spanish, Swedish and Argentina cases and controls. Briefly, these three sets were genotyped at the Rudbeck Laboratory in Uppsala using TaqMan assay-on-demand from ABI for rs2004640. The average genotype completeness was 99% for Swedish, 98% for Argentina and 86% for Spanish samples. rs752637 also was typed by TaqMan using the following primers: forward, 5'-GCAAAAGGTGC-CCAGAAAG AAG-3' (SEQ ID NO:17); reverse, 5'-TC-CCCTGTACCCTGGTCTTC-3' (SEQ ID NO:18); extension (vic), 5'-CTTCTTTCAGCTTCCTC-3' (SEQ ID NO:19); and extension (fam), 5'-TCTTTCGGCTTCCTC-3' (SEQ ID NO:20).

rs2280714 was typed for the case-control studies on both the Sequenom platform and using a TaqMan assay (Rudbeck Laboratory). Over 1100 individuals were typed on both platforms with 98.2% concordance of results. The following samples were not typed for rs2280714: 63 OMRF trios, 96 Spanish SLE cases, 126 Swedish cases, and 161 Swedish controls. Hardy-Weinberg equilibrium P values for rs2004640 and rs2280714 for each population are presented in Table 6.

Statistical Analysis: Family-based Association Analysis—The Transmission Disequilibrium Test (TDT) was performed using Haploview v3.2 (available on the World Wide Web at broad.mit.edu/mpg/haploview/) under default settings. Haploview v3.2 examines the transmission patterns of all complete trios within each pedigree. To assess the statistical significance of the results, the transmitted/untransmitted status of each genotype and haplotype was randomly permutated for 1,000,000 iterations and the best chi-square value generated for each permutated dataset was recorded. The number of times the permutated chi-square value exceeded the nominal chi-square value was divided by the number of iterations (1,000,000) to generate the permutated P value. The Pedigree Disequilibrium Test (PDT) was performed as described (Martin et al. (2000) *Am. J. Hum. Genet.* 67:146-154).

Case Control Analysis—$\chi^2$ analysis was used to evaluate the significance of differences in genotype and allele frequencies in the case-control samples. The allele frequencies for cases and controls were used to calculate the Odds Ratio (OR) and the 95% confidence interval using Woolf's method (ln (OR)+−1.96(1/A+1/B+1/C+1/D)^0.5.). The chi-square value was calculated from the 2×2 contingency tables and p-values were determined using 1 degree of freedom.

Meta Analysis—Published results of the association of rs2004640 with SLE in Finnish and Swedish collections (Sigurdsson et al. supra) were combined with results for rs2004640 in SLE cases collected in Argentina, Spain, Sweden and the United States using the Mantel-Haenszel meta-analysis of the odds ratios (ORs; Lohmueller et al. (2003) *Nat. Genet.* 33:177-182; Woolson and Bean (1982) *Stat. Med.* 1:37-39).

Determination and quantification of IRF5 UTR-specific transcripts: Total RNA from SLE patients carrying the various genotypes was purified from PBMCs with TRIZOL reagent (Invitrogen). 2 μg of total RNA was reverse transcribed with 2 U of MultiScribe transcriptase in the PCR buffer II containing 5 mM MgCl$_2$, 1 mM dNTPs, 0.4 U of RNase inhibitor and 2.5 μM random hexamers (all results were confirmed using oligo-dT primed cDNA). All reagents were from Applied Biosystems. Synthesis was performed at 42° C. for 45 minutes and the reaction was terminated at 95° C. for 5 minutes.

IRF-5 isoforms with distinct 5'-UTRs were quantified by real-time TaqMan-PCR on ABI PRISM 7700 Sequence Detector (Applied Biosystems) with SDS 1.9.1 software. Primers used to distinguish PCR products with different UTRs were: forward (A) Exon-1A-UTR 5'-ACGCAGGCG-CACCGCAGACA-3' (SEQ ID NO:21), (B) Exon-1B-UTR: 5'-AGCTGCGCCTGGAAAGCGAGC-3' (SEQ ID NO:22), (C) Exon1C-UTR: 5'-AGGCGGCACTAGGCAGGTG-CAAC-3' (SEQ ID NO:23), and a common reverse primer lying in exon 3 5'-TCGTAGATCTTGTAGGGCTGAGGTG-GCA-3' (SEQ ID NO:24). TaqMan probe labeled with FAM and TAMRA was 5'-CCATGAACCAGTCCATCCCAGTG-GCTCCCACC-3' (SEQ ID NO:25). 45 or 52 cycles of two-step PCR were run in a buffer containing 1.5 mM MgCl$_2$, 200 μM of each of dNTP, 0.5 U of Platinum Taq polymerase (Invitrogen), primer-probe mix and cDNA. Extension/elongation was maintained at 65° C. for 1 minute, while denaturation was at 95° C. for 15 seconds. Expression levels were normalized using human β2-microglobulin with commercial primer-probe mix (Applied Biosystems).

Standard PCR amplification of diverse isoforms of IRF-5 was performed with the same forward primers as for the TaqMan assay with reverse primer designed so as to allow amplification of all transcripts containing exon 8: 5'-GAAACTTGATCTCCAGGT CGGTCA-3' (SEQ ID NO:26). Cycle conditions were: initial denaturation at 95° C. for 3 minutes, followed by 40 cycles of denaturation at 95° C. for 15 seconds, annealing at 60° C. for 15 seconds and elongation at 72° C. for 1.5 minutes. PCR was performed in a 25 μl reaction volume, with 0.5 U of Platinum Taq polymerase (Invitrogen) in the buffer supplied with enzyme. PCR products were electrophoresed on a 1.5% agarose gel.

The statistical analysis of isoform expression was performed using t-test included in GraphPad Software (World Wide Web at graphpad.com).

Cloning and sequencing of IRF-5 isoforms: To isolate novel isoforms, total RNA isolated from human PBMCs of two rs2004640 TG SLE patients was subjected to RT-PCR with the same forward primers matching to Exon1 used for the TaqMan RT-PCR assays, and a common reverse primer lying in the last exon: 5'-CTGAGAACATCTCCA GCAG-CAG-3' (SEQ ID NO:27). PCR products were analyzed by gel electrophoresis and individual bands were cut out and purified. Sequencing was performed using the Big Dye reaction at the Uppsala Genome Center. Two novel transcripts named V10 and V11 were identified and deposited to GenBank under accession numbers DQ277633 and DQ277634, respectively.

IRF-5 expression analysis: Two IRF-5 region SNPs (rs2004640 and rs2280714) were genotyped using the Sequenom platform described above in 30 CEPH trios (CEU, 90 individuals) from the International Haplotype Map project (Altshuler et al. (2005) *Nature* 437:1299-1320) and the data was integrated into the Phase II data (HapMap data release #19) for 100 kb flanking IRF-5. In addition, three SNPs (rs726302, rs2004640, and rs2280714) were genotyped in the 233 CEPH individuals (14 extended pedigrees, including 21 trios that are part of the HapMap CEU samples, and 38 unrelated individuals) described in Morley et al. ((2004) *Nature* 430:743-747), using a Sequenom platform. Linear regression (R statistical package) was used to test the significance of association of genetic variants to IRF-5 expression levels using publicly available gene expression data (GEO accession number GSE1485, IRF-5 probe 205469_s_at; Morley et al. supra) in the 233 CEPH individuals, subdivided by (a) 42 unrelated founders included in the HapMap CEPH (CEU) population, (b) 92 unrelated individuals, and (c) all 233 individuals. Gene expression data were also obtained from the PBMCs of 37 SLE cases (Affymetrix U95A chips, IRF5 probe set 36465_at; Baechler et al. supra) and from PaxGene RNA from whole blood of 41 independent Caucasian SLE cases (Affymetrix 133A chips, IRF5 probe set 205469_s_at).

Enrichment of the IRF-5 rs2004640 T Allele in SLE

Four sets of SLE cases and controls from the United States, Spain, Sweden and Argentina (total of 1,661 cases and 2,508 controls) were genotyped, and association of the IRF-5 rs2004640 T allele was assessed using a standard case-control study design. In all sets, a significant enrichment of the T allele was observed in SLE cases as compared to matched controls (overall 60.4% in cases vs. 51.5% in controls, P=4.4×10$^{-16}$; Table 1). The frequency of the T allele was lower in the Argentine sample possibly due to the mixed ethnicity of the individuals studied (see Example 1). Importantly, in a subset of 470 cases from the U.S. for which family members were available, a family-based association ruled out the possibility that stratification could explain the results (P=0.0006, Table 3).

When all available case/control data were examined (four independent cohorts described here, together with the two published cohorts from Sweden and Finland; Sigurdsson et al., supra), robust and consistent association of the rs2004640 T allele with SLE was observed, with individual odds ratios (OR) ranging between 1.31 and 1.84 (Table 1). Using the Mantel-Haenszel method for meta-analysis of ORs, the pooled OR for the rs2004640 SNP T allele was found to be 1.47 (1.36-1.60), with an overall P=4.2×10$^{-21}$ (Table 1). A single copy of the rs2004640 T allele was found in 45% of cases and conferred modest risk (pooled OR=1.27, P=0.0031), while the 38% of cases homozygous for the T allele are at a greater risk for SLE (pooled OR=2.01, P=3.7× 10$^{-14}$; Table 2). Based on these results, dominant and recessive models of inheritance can be formally rejected, and the likely mode of inheritance is additive or multiplicative. Thus, the evidence for association of the T allele of rs2004640 is highly significant, well surpassing even correction for testing all common variants in the human genome.

Functional Consequences of the IFR-5 rs2004640 T Allele

Given the convincing data for association of IRF-5 with SLE risk, the potential functional consequences of the rs2004640 T allele were investigated. Examination of the genomic sequence of IRF-5 revealed that the rs2004640 T allele is located two bp downstream of the intron/exon border of exon-1B, creating a consensus GT donor splice site (FIG. 1a). Thus, studies were conducted to determine if rs2004640 influenced IRF-5 splicing, which is highly complex (Mancl et al. (2005) *J. Biol. Chem.* 280:21078-21090). IRF-5 transcripts are initiated at one of three promoters, giving rise to transcripts containing exon-1A, exon-1B or exon-1C (FIG. 1a). Transcripts initiated at exon-1A and exon-1B are constitutively expressed in plasmacytoid dendritic cells and B cells, while exon-1C bearing transcripts are inducible by type-I IFNs. In addition, multiple IRF-5 isoforms are initiated at each promoter, with 9 previously identified isoforms (V1-V9, FIG. 1a).

To determine whether rs2004640 affected expression of IRF-5 transcripts bearing exon-1B, PBMCs were isolated from individuals carrying GG, GT or TT rs2004640 genotypes, and first strand cDNA was synthesized. Using specific primers to detect transcripts associated with each of the three exon 1 variants, it was observed that SLE patients and controls homozygous for the G allele expressed IRF-5 isoforms containing exon-1A and exon-1C, but not exon-1B. In contrast, individuals homozygous or heterozygous for the T allele expressed exon-1B, as well as both exon-1A and exon-1C, containing transcripts. TaqMan PCR assays clearly documented that exon-1B transcripts were only detectable in the presence of the rs2004640 T allele (FIG. 1b). In all samples studied (N=20), exon-1A containing transcripts were more abundant than the other mRNA classes. Based on the above, it is apparent that only individuals with the rs2004640 T allele will express the multiple isoforms of IRF-5 initiated at exon-1B.

Given the association of the rs2004640 T allele to SLE and the fact that only individuals carrying the SNP express IRF-5 exon-1B transcripts, further studies were conducted to obtain additional IRF-5 isoforms. Two novel isoforms of IRF-5 were cloned from the peripheral blood mRNA of rs2004640 heterozygote donors: V10, which utilizes exon-1B and has an in-frame deletion of 30 nt at the beginning of exon 7, and a predicted protein 10 amino acids shorter than V2; and V11, a transcript derived from exon-1C with a 28 bp deletion of exon 3, predicted to encode a truncated protein translated from an alternate reading frame (FIG. 1a). Several of these isoforms, including isoforms initiated at exon-1B, contain splicing variation in and around exon 6, which encodes part of an extended PEST domain. PEST domains are highly enriched for proline, glutamic acid, serine and threonine, and can be associated with control of protein stability. Several unique and constitutively expressed IRF-5 isoforms are initiated at exon-1B, and these isoforms may influence the function of IRF-5 or the transcriptional profile of IRF-5 target genes.

Association Between Elevated IFR-5 Expression and the Exon-1B Splice Site

Experiments were conducted to determine whether elevated expression of IRF-5 might be associated with the exon-1B splice site, using a common variant near IRF-5 that is one of the polymorphisms most strongly associated with variation in gene expression (Morley et al. (2004) *Nature* 430:743-747; and Cheung et al. (2005) *Nature* 437:1365-1369). This variant, the rs22807814 T allele, is about 5 Kb downstream of IRF-5, and has been identified as being, or being in strong linkage disequilibrium (LD) with, a cis-acting determinant of IRF-5 expression.

The relationship between rs2004640 and rs2280714 was evaluated in 30 independent CEPH trios from the HapMap project. D' for the two SNPs is 0.96; i.e., nearly all copies of the splice site rs2004640 T allele are on haplotypes bearing the rs2280714 T allele. However, $r^2$ for these SNPs is only 0.66, since the downstream rs2280714 T allele is also found on haplotypes that lack the splice site rs2004640 T allele (see Table 3 and FIG. 4). While these two SNPs are strongly linked, the fact that the 3' rs2280714 T allele can be observed in the absence of the upstream splice site SNP allowed determination of which variant is the best predictor of IRF-5 expression and also SLE risk.

Figure 2:
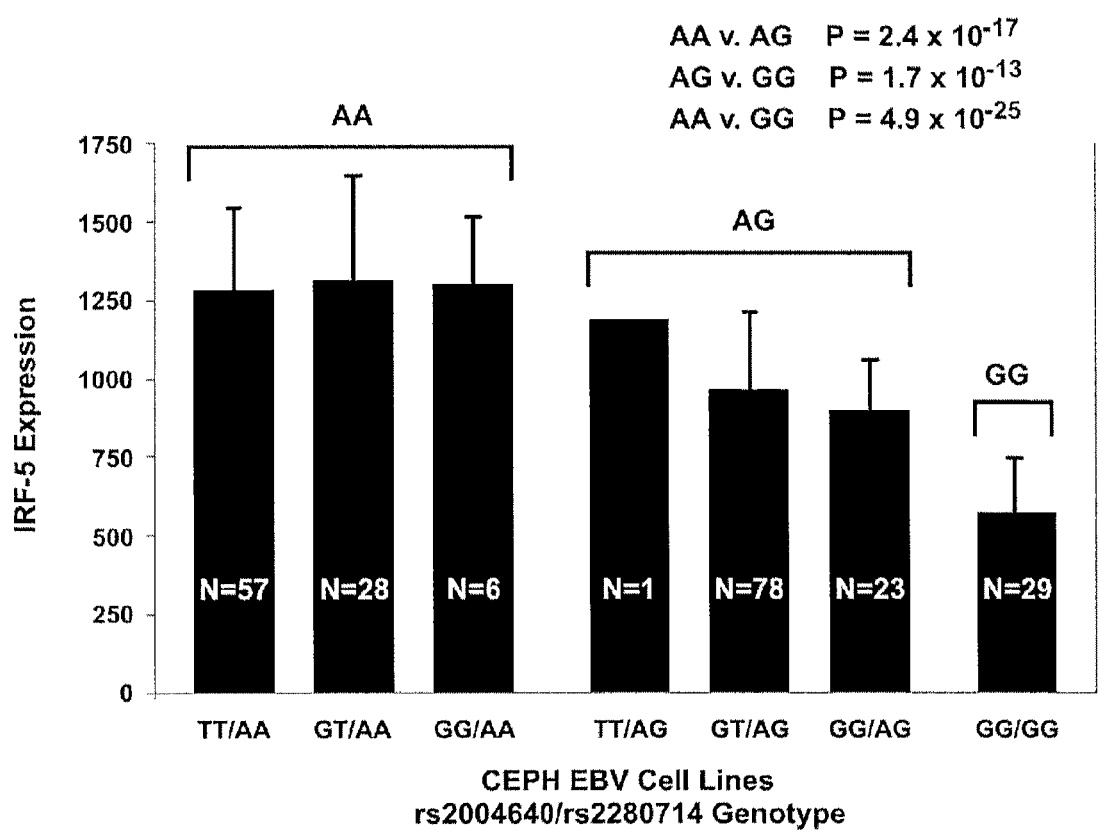
FIG. 2 is a graph showing levels of IRF-5 mRNA as determined by microarray, compared between EBV transformed cell lines from CEPH individuals typed for rs2004640 and rs2280714. Identical findings were observed when only CEPH founders were examined.
Figure 3A:
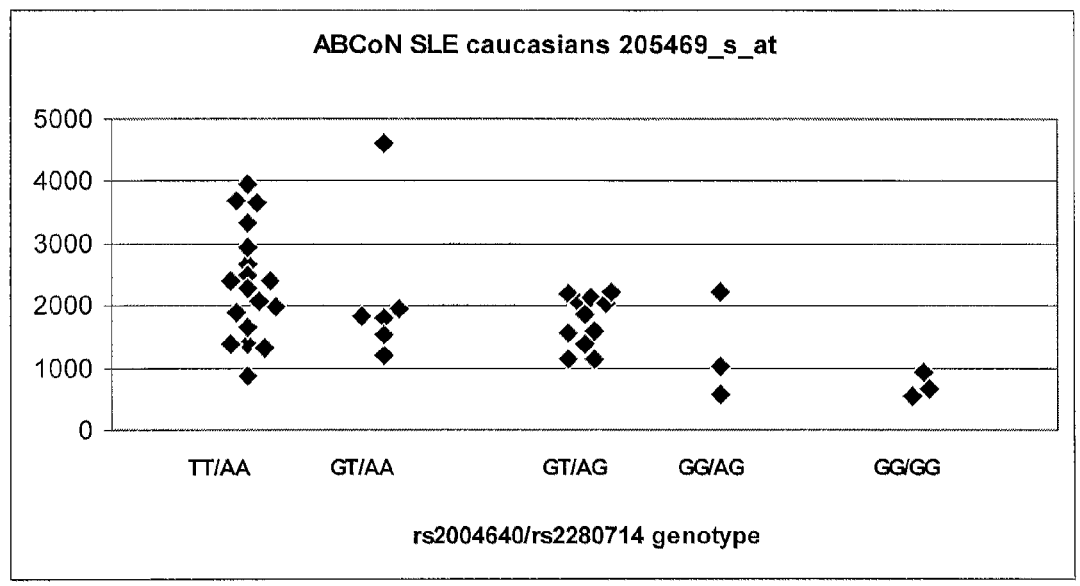
FIG. 3a and FIG. 3b are graphs showing levels of IRF-5 measured by Affymetrix microarrays, compared in whole blood (N=37.
Figure 3B:
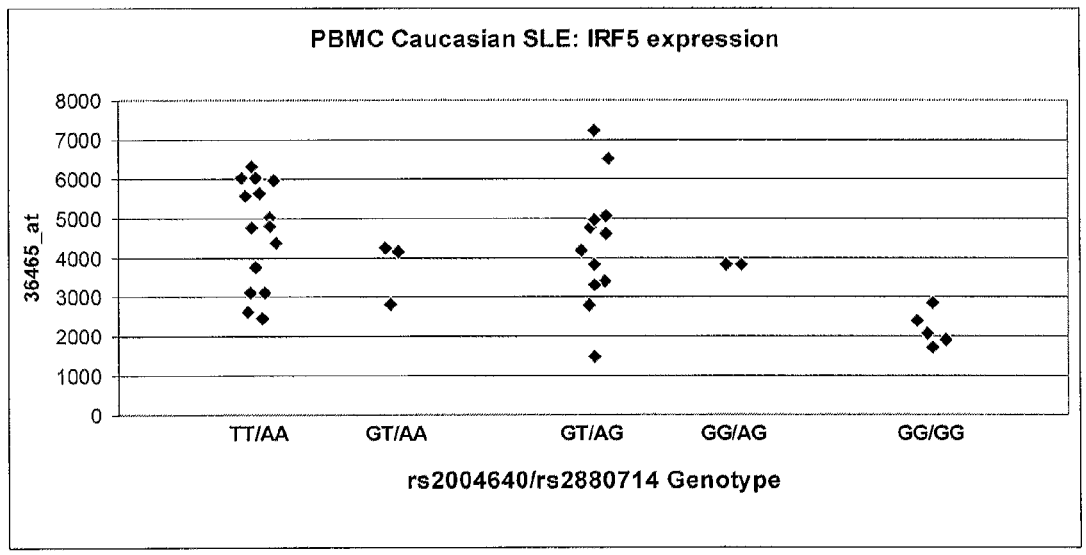

The association of IRF-5 expression to the two SNPs was tested in expression data from EBV-transformed B cells of CEPH family members, and from peripheral blood cells of two independent sets of SLE cases. The rs2004640 and rs2280714 alleles were genotyped in 233 CEPH individuals, used for a genome-wide survey of determinants of gene expression (Morley et al. supra), and examined for association to IRF-5 expression. The T alleles of both rs2004640 and rs2280714 were found to be associated with higher levels of IRF-5 mRNA expression (FIG. 2). However, the rs2280714 T allele was a better predictor of IRF-5 overexpression in 92 unrelated individuals than the rs2004640 T allele ($P=2\times10^{-16}$ vs. $P=5.3\times10^{-11}$, respectively), and in the full data set of 233 individuals, consisting of 14 extended pedigrees and 38 unrelated individuals (FIG. 2). Similar findings were observed in the peripheral blood cells of two independent groups of SLE cases (FIGS. 3a and 3b). Based on these data, the hypothesis that the splice site rs2004640 SNP is the cis-acting variant controlling expression can be rejected, since rs2280714 remains significantly associated with IRF-5 expression ($P=4.7\times10^{-7}$) after logistic regression conditional on rs2004640, whereas rs2004640 no longer remains significant after controlling for rs2280714.

Using phase II HapMap genotype data (~5 million SNPs across the genome), all available variants (including rs2004640 and rs2280714) within 100 kb of IRF-5 were tested for association to IRF-5 expression in EBV-transformed B-cells from 42 unrelated individuals from the HapMap CEPH (CEU) population. The rs2280714 variant and 4 polymorphisms that are perfect proxies of rs2280714 ($r^2=1.0$) are the most strongly associated with IRF-5 gene expression ($P=1.0\times10^{-10}$, Table 4). Given that these variants are well downstream of IRF-5, and that they do not lie in a recognizable regulatory region, there may be additional genetic variation in tight LD with rs2280714 that drives the expression phenotype.

Association of IRF-5 with SLE

Studies were conducted to determine whether over-expression of IRF-5 (rs2280714), the presence of exon-1B initiated IRF-5 isoforms (rs2004640), or both, are associated with SLE. The fact that ~14% of IRF-5 haplotypes are associated with over-expression, but lack the exon-1B splice site, allows the opportunity to test whether the allele associated with overexpression (rs2280714) is independently associated with SLE (Table 3). Indeed, in 470 SLE pedigrees, only haplotypes bearing the exon-1B splice site (rs2004640 T allele) show over-transmission using the transmission disequilibrium test 19 (208:149 T:U, P=0.0021; Table 3). Haplotypes associated with over-expression of IRF-5 (rs2280714 T allele) but lacking the exon-1B splice site show no evidence for risk to SLE (70:108 T:U; Table 3). Supporting the family-based analysis, there was no difference observed in the frequency of the rs2004640/rs2280714 'G/T' haplotype between SLE cases (n=1358, 13%) and controls (n=2278, 15%; P=0.98; Table 5). Additionally, rs2280714 was not significantly associated with SLE in the case-control analysis after logistic regression conditional on rs2004640 (P=0.22). Thus, over-expression of IRF-5 in the absence of the exon-1B splice site does not confer risk to SLE.

Identification of the Cis-Acting Variant Linked to IRF-5 Over-Expression

Figure 5:
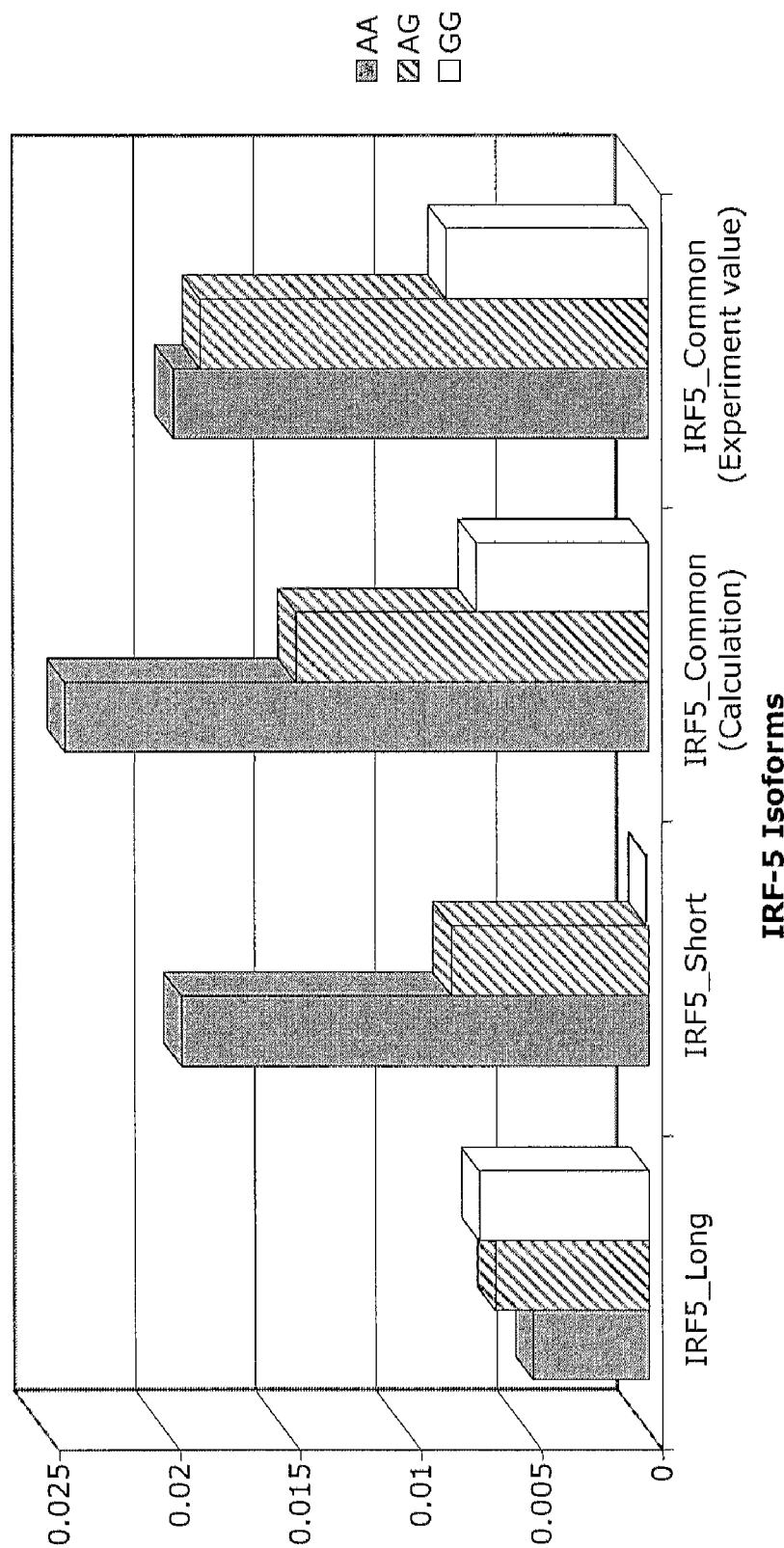
FIG. 5 is a graph showing levels of expression of the long IRF-5 isoform (IRF5_Long), the short IRF-5 isoform (IRF5_Short), or both isoforms (IRF5_Common) as determined in individuals homozygous for the rs10954213 A allele (gray bars), heterozygous for the rs10954213 A allele (striped bars), or homozygous for the rs10954213 G allele (white bars).

Additional studies were conducted to determine whether the rs10954213 A allele is the cis-acting variant that causes IRF-5 over-expression, and whether the presence of this variant augments the risk to SLE conferred by the exon-1B splice site. The presence of the rs10954213 A allele results in a "short form" IRF-5 mRNA having a truncated 3' UTR, as compared to the "long form" IRF-5 mRNA that is produced when an rs10954213 G allele is present. To measure mRNA expression, specific primers were used to amplify the short form IRF-5 isoform, the long form IRF-5 isoform, or both isoforms in samples from individuals homozygous or heterozygous for the rs10954213 A allele, as well as individuals homozygous for the rs10954213 G allele. As shown in FIG. 5, the short form was predominantly expressed in individuals having the rs10954213 A allele. Expression was significantly greater in homozygous individuals than in heterozygous individuals. The presence of an rs10954213 A allele did not preclude expression of the long form, but levels of the long form were significantly less than levels of the short form, particularly in individuals homozygous for the rs10954213 A allele. Further, the overall level of IRF-5 expression was significantly greater in individuals homozygous for the rs10954213 A allele than in individuals heterozygous for the allele (FIG. 5). In turn, the overall level of IRF-5 expression was significantly greater in individuals heterozygous for the rs10954213 A allele than in individuals homozygous for the rs10954213 G allele. Thus, the rs10954213 A allele is linked to increased expression levels of IRF-5.

Genetic analysis of IRF-5 haplotypes demonstrated that the presence of a short-form (rs10954213 A) allele does not confer significant risk for SLE unless an Exon-1B (rs2004640 T) allele also is present (Table 7). Further genetic analysis demonstrated that the presence of a short-form allele augments the risk conferred by the presence of an Exon-1B allele.

As presented in Table 8, haplotypes are indicated such that the first letter represents the rs2004640 SNP and the second letter represents the rs10954213 SNP. "Hap1" and "Hap2" represent the two haplotypes present in each group of individuals. Thus, the first row of Table 8 contains data for individuals homozygous for the rs2004640 T allele and the rs10954213 A allele, whereas the second row of Table 8 contains data for individuals homozygous for the rs2004640 T allele and heterozygous for the rs10954213 A allele. "2×" and "1×" thus refer to the number of copies of the risk alleles at each SNP. These data show that having the short-form allele augments the risk that is conferred by having the Exon-1B transcripts. The data also suggest that having the Exon-1B isoforms does not confer risk to SLE in the absence of the short-form allele, although those combinations of haplotypes (TG/TG and TG/GG) are relatively rare.

Cytokine Secretion in Response to TLR and IFN Signaling

PBMCs (~1×10$^6$ cells/ml) were collected from normal donors with various IRF-5 genotypes at the rs2004640 and rs10954213 alleles. Specifically, cells were collected from four donors having a TT/AA haplotype (i.e., homozygous for the rs2004640 T allele and homozygous for the rs10954213 A allele), and three donors having a GG/GG haplotype (i.e., homozygous for the rs2004640 G allele and homozygous for the rs10954213 G allele). Cells were stimulated with optimal concentrations of TLR7 ligand (R848), IFN-α, or CpG oligos. Controls were treated with phosphate buffered saline (PBS). Luminex assays were used to measure levels of various cytokines secreted after 6 hours of simulation. Specifically, levels of IL-1RA, IL-6, MPC-1, MIP-1α, MIP-1β, and TNF-α were measured using a Luminex xMAP system (Luminex Corp., Austin, Tex.). As shown in Table 9, cells harvested from individuals having a TT/AA haplotype secreted higher levels of the various cytokines in response to TLR and IFN signaling.

Taken together, the data presented herein confirm the association of IRF-5 to SLE, and identify the IRF-5 risk haplotype as the strongest genetic effect outside the HLA yet discovered in this disease. There are three functional variants within IRF-5: the rs2004640 T allele provides a splice donor site that allows expression of multiple IRF-5 isoforms containing exon-1B, while rs2280714 and its proxies, as well as rs10954213, are associated with elevated IRF-5 expression. The IRF-5 exon-1B isoforms are strongly linked to elevated expression of IRF-5 and to risk of SLE; over-expression of IRF-5 in the absence of exon-1B isoforms does not confer risk. Thus, over-expression of exon-1B transcripts may augment the risk to SLE.

TABLE 1

Case/control association analysis of rs2004640 T allele with SLE

| | | N[a] | T[b] | T freq. | G[c] | G freq. | OR (95% CI)[d] | $\chi^2$ | P | Pooled OR[e] | Pooled P |
|---|---|---|---|---|---|---|---|---|---|---|---|
| Argentina | Cases | 284 | 309 | 0.54 | 259 | 0.46 | 1.52 (1.20-1.93) | 12.8 | 0.00035 | 1.45 (1.32-1.58) | $4.4 \times 10^{-16}$ |
| | Controls | 279 | 245 | 0.44 | 313 | 0.56 | | | | | |
| Spain | Cases | 444 | 559 | 0.63 | 329 | 0.37 | 1.31 (1.09-1.57) | 14.3 | 0.00016 | | |
| | Controls | 541 | 589 | 0.54 | 493 | 0.46 | | | | | |
| Sweden-1 | Cases | 208 | 260 | 0.63 | 156 | 0.38 | 1.31 (1.01-1.71) | 4.1 | 0.04268 | | |
| | Controls | 254 | 284 | 0.56 | 224 | 0.44 | | | | | |
| U.S.A. | Cases | 725 | 879 | 0.61 | 571 | 0.39 | 1.47 (1.29-1.67) | 34.8 | $3.6 \times 10^{-9}$ | | |
| | Controls | 1434 | 1467 | 0.51 | 1401 | 0.49 | | | | | |
| Sweden-2[f] | Cases | 480 | 595 | 0.62 | 365 | 0.38 | 1.51 (1.21-1.87) | 13.8 | 0.0002 | 1.59 (1.31-1.94) | $7.1 \times 10^{-7}$ |
| | Controls | 256 | 266 | 0.52 | 246 | 0.48 | | | | | |

TABLE 1-continued

Case/control association analysis of rs2004640 T allele with SLE

| | | N[a] | T[b] | T freq. | G[c] | G freq. | OR (95% CI)[d] | $\chi^2$ | P | Pooled OR[e] | Pooled P |
|---|---|---|---|---|---|---|---|---|---|---|---|
| Finland[f] | Cases | 109 | 137 | 0.63 | 81 | 0.37 | 1.84 (1.27-2.66) | 10.3 | 0.00133 | | |
| | Controls | 121 | 116 | 0.48 | 126 | 0.52 | | | | | |
| Combined | Cases | 2250 | 2739 | 0.61 | 1761 | 0.39 | | | | 1.47 (1.36-1.60) | $4.2 \times 10^{-21}$ |
| Analysis | Controls | 2885 | 2967 | 0.51 | 2803 | 0.49 | | | | | |

[a]Number of individuals
[b]Number of T alleles of rs2004640
[c]Number of G alleles of rs2004640
[d]Odds ratio and 95% confidence intervals
[e]Mantel-Haenszel test of pooled odds ratios and 95% confidence intervals
[f]Data from Sigurdsson et al.

TABLE 2

Genotypic association of rs2004640 with SLE

| | Genotype | Cases | Frequency | Controls | y | | OR (95% CI) | $\chi^2$ | P[a] |
|---|---|---|---|---|---|---|---|---|---|
| | | N[b] = 284 | | N = 282 | | | | | |
| Argentina | GG | 65 | 0.23 | 90 | 0.32 | | | | |
| | GT | 129 | 0.45 | 135 | 0.48 | GT v GG | 1.32 (0.89-1.97) | 1.9 | 0.1692 |
| | TT | 90 | 0.32 | 57 | 0.20 | TT v GG | 2.19 (1.38-3.46) | 11.2 | 0.0008 |
| | | | | | | TT v GT + GG | 1.83 (1.25-2.69) | 9.7 | 0.0019 |
| | | N = 445 | | N = 542 | | | | | |
| Spain | GG | 82 | 0.18 | 112 | 0.21 | | | | |
| | GT | 165 | 0.37 | 269 | 0.49 | GT v GG | 0.84 (0.59-1.18) | 1.0 | 0.3149 |
| | TT | 198 | 0.45 | 161 | 0.30 | TT v GG | 1.68 (1.18-2.39) | 8.4 | 0.0038 |
| | | | | | | TT v GT + GG | 1.90 (1.45-2.47) | 23.1 | $1.6 \times 10^{-6}$ |
| | | N = 208 | | N = 254 | | | | | |
| Sweden | GG | 25 | 0.12 | 47 | 0.18 | | | | |
| | GT | 106 | 0.51 | 130 | 0.51 | GT v GG | 1.53 (0.89-2.65) | 2.3 | 0.1257 |
| | TT | 77 | 0.37 | 77 | 0.30 | TT v GG | 1.88 (1.05-3.35) | 4.6 | 0.0315 |
| | | | | | | TT v GT + GG | 1.35 (0.92-1.99) | 2.3 | 0.1283 |
| | | N = 624 | | N = 967 | | | | | |
| U.S. | GG | 93 | 0.15 | 204 | 0.21 | | | | |
| | GT | 306 | 0.49 | 470 | 0.49 | GT v GG | 1.43 (1.07-1.90) | 6.1 | 0.0138 |
| | TT | 225 | 0.36 | 293 | 0.30 | TT v GG | 1.61 (1.25-2.28) | 11.7 | 0.0006 |
| | | | | | | TT v GT + GG | 1.30 (1.05-1.61) | 5.7 | 0.0167 |
| | | N = 1561 | | N = 2045 | | | | | |
| All | GG | 265 | 0.17 | 453 | 0.22 | | Pooled OR[c] | | Pooled P |
| | GT | 706 | 0.45 | 1004 | 0.49 | GT v GG | 1.22 (1.02-1.47) | | 0.014 |
| | TT | 590 | 0.38 | 588 | 0.29 | TT v GG | 1.78 (1.47-2.16) | | $2.8 \times 10^{-9}$ |
| | | | | | | TT v GT + GG | 1.53 (1.33-1.76) | | $2.0 \times 10^{-9}$ |

[a]P value, uncorrected for multiple tests, 1 degree of freedom
[b]Number of individuals
[c]Mantel-Haenszel test of pooled odds ratios and 95% confidence intervals

TABLE 3

TDT analysis of IRF-5 in 467 U.S. SLE Caucasian pedigrees

| Marker | Allele | Frequency[a] | T[b] | U[b] | T/U | $\chi^2$ | Nominal P[c] | Permuted P[d] |
|---|---|---|---|---|---|---|---|---|
| rs729302 | A | 0.69 | 199 | 130 | 1.53 | 14.5 | 0.0001 | 0.0007 |
| rs2004640 | T | 0.57 | 219 | 153 | 1.43 | 11.7 | 0.0006 | 0.0028 |

TABLE 3-continued

TDT analysis of IRF-5 in 467 U.S. SLE Caucasian pedigrees

| | | | | | | | | |
|---|---|---|---|---|---|---|---|---|
| rs752637 | G | 0.68 | 199 | 161 | 1.24 | 4.0 | 0.0450 | 0.2999 |
| rs2280714 | A | 0.72 | 153 | 127 | 1.20 | 2.4 | 0.1202 | 0.6248 |

| Haplotype[a] | Frequency | T | U | T/U | $\chi^2$ | Nominal P | Permuted P |
|---|---|---|---|---|---|---|---|
| ATGA | 0.54 | 192 | 139 | 1.38 | 8.5 | 0.0035 | 0.0192 |
| CGAG | 0.15 | 69 | 101 | 0.69 | 5.7 | 0.0167 | 0.1093 |
| AGAG | 0.13 | 88 | 77 | 1.14 | 0.7 | 0.4047 | 1.0000 |
| CGGA | 0.10 | 52 | 79 | 0.66 | 5.3 | 0.0216 | 0.1424 |
| CGAA | 0.04 | 18 | 29 | 0.60 | 2.9 | 0.0897 | 0.5105 |
| CTGA | 0.02 | 16 | 11 | 1.54 | 1.2 | 0.2645 | 0.9048 |
| XTXX[f] | 0.56 | 208 | 149 | 1.39 | 9.8 | 0.0017 | — |
| XGXX[f] | 0.42 | 227 | 285 | 0.80 | 6.6 | 0.0102 | — |

[a] Frequency in parental chromosomes
[b] Transmitted and untransmitted chromosomes, and the transmission ratio (T/U)
[c] P value, uncorrected for multiple tests
[d] P value from 1,000,000 random iterations of the genotype data, as described in methods
[e] Haplotype consisting of markers; rs729302, rs2004640, rs752637, rs2280714
[f] Haplotypes carrying "T" or "G" allele of rs2004640

TABLE 4

Association of HapMap phase II variants to IRF-5 expression levels

| Marker[a] | Chr | Position[b] | MAF[c] | $r^2$ to rs2280714[d] | P[e] |
|---|---|---|---|---|---|
| rs729302 | 7 | 128,122,922 | 0.32 | 0.09 | 0.2 |
| rs2004640 | 7 | 128,132,263 | 0.49 | 0.68 | $6.0 \times 10^{-8}$ |
| rs752637 | 7 | 128,133,382 | 0.45 | 0.83 | $2.8 \times 10^{-9}$ |
| rs2280714 | 7 | 128,148,687 | 0.42 | — | $1.0 \times 10^{-10}$ |
| rs7789423 | 7 | 128,175,166 | 0.42 | 1.00 | $1.0 \times 10^{-10}$ |
| rs6948928 | 7 | 128,177,059 | 0.42 | 1.00 | $1.0 \times 10^{-10}$ |
| rs3857852 | 7 | 128,211,235 | 0.42 | 1.00 | $2.6 \times 10^{-10}$ |
| rs13221560 | 7 | 128,217,133 | 0.39 | 1.00 | $7.4 \times 10^{-10}$ |
| rs921403 | 7 | 128,230,682 | 0.43 | 0.97 | $4.0 \times 10^{-10}$ |
| rs10279821 | 7 | 128,237,505 | 0.41 | 0.97 | $4.9 \times 10^{-10}$ |
| rs10156169 | 7 | 128,238,529 | 0.42 | 0.93 | $3.4 \times 10^{-10}$ |

[a] HapMap Phase II markers with P < $1.0 \times 10^{-9}$ are shown, in addition to the results for IRF-5 region markers genotyped in the SLE families (rs729302, rs2004640, rs752637)
[b] Position in HG16 (Build 34).
[c] Minor Allele Frequency in HapMap CEPH (CEU) population.
[d] Correlation to rs2280714.
[e] P calculated using conditional linear regression, testing variants for association to IRF-5 expression in EBV-transformed B cells from CEPH individuals.

TABLE 5

IRF-5 haplotype frequency SLE cases and controls

| | Haplotype[a] | | | | | | | |
|---|---|---|---|---|---|---|---|---|
| | rs2004640 | rs2280714 | Cases | Frequency | Controls | Frequency | $\chi^2$ | P[b] |
| | | | N[c] = 282 | | N = 262 | | | |
| Argentina | T | T | 303 | 0.54 | 227 | 0.43 | 11.8 | 0.0006 |
| | G | T | 54 | 0.10 | 70 | 0.13 | 3.8 | 0.0501 |
| | G | C | 205 | 0.36 | 224 | 0.43 | 4.7 | 0.0309 |
| | | | N = 350 | | N = 527 | | | |
| Spain | T | T | 419 | 0.60 | 547 | 0.52 | 10.8 | 0.0010 |
| | G | T | 109 | 0.16 | 167 | 0.16 | 0.0 | 0.9212 |
| | G | C | 155 | 0.22 | 316 | 0.30 | 13.2 | 0.0003 |
| | T | C | 17 | 0.02 | 25 | 0.02 | 0.0 | 0.9366 |

TABLE 5-continued

IRF-5 haplotype frequency SLE cases and controls

| | Haplotype[a] | | Cases | Frequency | Controls | Frequency | $\chi^2$ | P[b] |
|---|---|---|---|---|---|---|---|---|
| | rs2004640 | rs2280714 | | | | | | |
| | | | N = 82 | | N = 93 | | | |
| Sweden | T | T | 99 | 0.60 | 109 | 0.59 | 0.1 | 0.7514 |
| | G | T | 29 | 0.18 | 32 | 0.17 | 0.2 | 0.6642 |
| | G | C | 36 | 0.22 | 44 | 0.24 | 0.0 | 0.9431 |
| | | | N = 649 | | N = 1405 | | | |
| U.S.A. | T | T | 780 | 0.60 | 1422 | 0.51 | 32.0 | $1.6 \times 10^{-8}$ |
| | G | T | 162 | 0.13 | 413 | 0.15 | 3.5 | 0.0599 |
| | G | C | 348 | 0.27 | 961 | 0.34 | 22.1 | $2.6 \times 10^{-9}$ |
| | | | N = 1358 | | N = 2278 | | | Pooled P[d] |
| ALL | T | T | 1601 | 0.59 | 2305 | 0.51 | | $1.9 \times 10^{-13}$ |
| | G | T | 354 | 0.13 | 682 | 0.15 | | 0.9842 |
| | G | C | 744 | 0.27 | 1545 | 0.34 | | $2.5 \times 10^{-10}$ |
| | T | C | 17 | 0.01 | 25 | 0.01 | | 0.9366 |

[a]Haplotype of rs2004640 and rs2280714, phased using Haploview software. Only samples with complete genotype data were analyzed.
[b]P value, uncorrected for multiple tests, 1 degree of freedom
[c]Number of individuals
[d]Pooled P value from Mantel-Haenszel test of pooled odds ratios

TABLE 6

Hardy-Wienberg equilibrium expectation test in control samples

| Population | rs2004640 P[a] | rs2280714 P |
|---|---|---|
| Argentina | 0.62 | 1.00 |
| Spain | 0.99 | 0.20 |
| Sweden | 0.54 | 0.02 |
| USA | 0.54 | 0.68 |

[a]P value for deviation from genotype frequencies predicted under Hardy-Weinberg Equilibrium expectations

TABLE 7

Genetic analysis of IRF-5 haplotypes

| Exon 1B transcripts | Short form RNA/high expression | Haplotype rs2004640 | rs19054213 | rs2280714 | Cases N = 1343 | Frequency | Controls N = 2288 | Frequency | OR (95% CI) | P |
|---|---|---|---|---|---|---|---|---|---|---|
| YES | YES | T | A | T | 1450 | 0.54 | 2129 | 0.47 | 1.40 (1.27-1.54) | $7.6 \times 10^{-12}$ |
| YES | NO | T | G | T/C | 129 | 0.05 | 202 | 0.04 | 1.09 (0.86-1.37) | 0.2400 |
| NO | YES | G | A | T | 341 | 0.13 | 666 | 0.15 | 0.86 (0.75-1.00) | 0.0246 |
| NO | NO | G | G | C | 732 | 0.27 | 1545 | 0.34 | 0.72 (0.64-0.80) | $5.9 \times 10^{-9}$ |

TABLE 8

Genetic analysis of IRF-5 haplotypes

| Exon 1B transcripts | High expression short form RNA | Hap1 | Hap2 | Cases Frequency N = 1343 | Control Frequency N = 2248 | Pooled OR | Pooled P |
|---|---|---|---|---|---|---|---|
| YES (2X) | YES (2X) | TA | TA | 0.30 | 0.22 | 2.16 (1.65-2.83) | $1.2 \times 10^{-8}$ |
| YES (2X) | YES (1X) | TA | TG | 0.06 | 0.04 | 2.20 (1.50-3.24) | $2.9 \times 10^{-5}$ |
| YES (1X) | YES (2X) | TA | GA | 0.13 | 0.14 | 1.42 (1.05-1.93) | 0.0115 |
| YES (1X) | YES (1X) | TA | GG | 0.29 | 0.31 | 1.40 (1.07-1.81) | 0.0062 |
| YES (2X) | NO | TG | TG | 0.00 | 0.00 | 2.16 (0.62-7.55) | 0.1131 |
| YES (1X) | YES (1X) | TG | GA | 0.01 | 0.02 | 0.56 (0.24-1.36) | 0.9084 |
| YES (1X) | NO | TG | GG | 0.03 | 0.03 | 0.71 (0.71-1.77) | 0.3136 |
| NO | YES (2X) | GA | GA | 0.02 | 0.02 | 1.34 (0.78-2.31) | 0.1247 |
| NO | YES (1X) | GA | GG | 0.08 | 0.10 | 1.21 (0.87-1.69) | 0.1316 |
| NO | NO | GG | GG | 0.08 | 0.11 | | |

TABLE 9

In vitro stimulation of PBMC with TLR7 ligand, IFNα, or CpG oligos

| | PBS | | TLR7 | | IFNα | | CpG | |
|---|---|---|---|---|---|---|---|---|
| | TT/AA | GG/GG | TT/AA | GG/GG | TT/AA | GG/GG | TT/AA | GG/GG |
| IL-1RA | 290 | 5 | 17,310 | 10,975 | 9,029 | 2,136 | 682 | 45 |
| IL-6 | 0 | 0 | 2,955 | 137 | 19 | 17 | 8 | 0 |
| MCP-1 | 7 | 3 | 1,963 | 326 | 413 | 90 | 44 | 6 |
| MIP-1α | 0 | 0 | 5,482 | 170 | 0 | 0 | 0 | 0 |
| MIP-1β | 58 | 23 | 6,861 | 2,538 | 268 | 100 | 151 | 65 |
| TNF-α | 2 | 2 | 1,124 | 67 | 10 | 7 | 10 | 4 |

Example 2

Three Functional Variants of IRF-5 Define Risk and Protective Haplotypes for Human Lupus Resequencing and genotyping in patients with SLE revealed evidence for three functional alleles of IRF5: the exon 1B splice site variant described above, a novel 30 bp in-frame insertion/deletion (indel) variant of exon 6 that alters a PEST domain region, and a novel variant in a conserved polyA$^+$ signal sequence that alters the length of the 3' UTR and stability of IRF5 mRNAs. Haplotypes of these three variants define at least three distinct levels of risk to SLE.

Materials and Methods

Whole blood donors and cell lines. Whole blood cells were collected from 5 healthy self-described European-ancestry donors who have the TT/AA genotype (rs2004640/rs10954213), 5 donors who have TG/AG genotype and 4 donors who have GG/GG genotype, and were used for quantitative PCR analyses. In addition, Epstein-Barr virus (EBV) infected immortalized B lymphocyte cell lines from CEPH family members were obtained from the Coriell Cell Repository and genotyped for rs2004640 and rs10954213. Three cell lines each for the TT/AA genotype (GM12239, GM12154, and GM12761), the TG/AG genotype (GM7034, GM7345, and GM11881), and the GG/GG genotype (GM12145, GM7000, and GM12155) were selected for Northern, qPCR and Western analyses. CEPH cells were cultured in RPMI1640 medium (Cellgro) supplemented with 2 mM L-glutamine and 15% fetal bovine serum at 37° C. in a humidified chamber with 5% $CO_2$. Tet-off 293 cells were purchased from BD Biosciences and were cultured in Eagle Minimum Essential Media (Invitrogen Life Technologies) with 10% FBS, 4 mM L-glutamine, 100 units/ml penicillin G and 100 µg/ml streptomycin.

RNA extraction and cDNA synthesis. Whole blood total RNA was extracted from healthy donors using RNeasy® Mini Kits (Qiagen). Poly-A$^+$ RNA was extracted from CEPH cell lines using FastTrack® 2.0 Kits (Invitrogen). First-strand cDNAs were synthesized from RNAs using SuperScript II reverse transcriptase (Invitrogen) with Oligo(dT)12-18 primers (Invitrogen).

Quantitative PCR. Expression of IRF5 mRNA was quantified by real-time PCR with TaqMan assays using an ABI PRISM 7900HT Sequence Detector (Applied Biosystems). Primers and probes used to distinguish short form 3' UTRs, long form 3' UTRs, and all 3' UTRs are listed in Table 10. A TaqMan® Gene Expression Assay (Applied Biosystems) was used for glyceraldehyde-3-phosphate dehydrogenase (GAPDH). Fifty-five cycles of two-step PCR (95° C. for 15 seconds and 60° C. for 1 minute) were carried out for common primer and probe sets and GAPDH, and 55 cycles of three-step PCR (95° C. for 15 seconds, 48° C. for 15 seconds, and 60° C. for 40 seconds) were carried out for the short and long form IRF5 assays. PCR reaction mixtures contained 10 ng of cDNA from total RNAs or 2 ng of cDNA from poly-A$^-$ RNAs, 1× TagMan® Universal PCR Master mix (Applied Biosystems), 1 µM each of forward and reverse primers, and 250 nM of TagMan® MGB Probe (Applied Biosystems). Expression levels were normalized to GAPDH expression.

Northern Blotting. 0.5 µg of poly-A$^+$ RNA from CEPH cell lines was analyzed by Northern blotting. Poly-A RNA$^+$ was denatured with glyoxile/dimethylsulfoxide (DMSO) sample dye (NorthernMax-Gly Based system, Ambion), resolved on 1.2% agarose gels, and blotted onto BrightStar-Plus Nylon membranes (Ambion). Membranes were crosslinked with UV and hybridized for 16-18 hours with a $^{32}$P-labeled probe from the IRF5 proximal 3' UTR region and a with control GAPDH probe. Probes were generated by random primed DNA labeling using a DECAprime II kit (Ambion). Following stringent washes, membranes were exposed to a PhosphorImager® screen overnight and relative RNA levels were assessed using PhosphorImager® software (Molecular Dynamics (Sunnyvale, Calif.)). Total RNA was isolated from transfected Tet-off 293 cells, and probed with a radiolabeled cDNA fragment of beta-globin and GFP.

Western blotting. $1.5 \times 10^7$ cells from each of the CEU cell lines were solubilized using 0.6 ml of 1% SDS lysis buffer (150 mM NaCl, 50 mM Tris-HCl, pH 7.5) containing Complete Mini Protease Inhibitor (Roche). Cells were sheared through a 26G needle and incubated on ice for 30 minutes. The lysate was immediately centrifuged for 10 minutes at 14000 rpm and 4° C., and the supernatant was used for subsequent SDS-PAGE and Western blot analyses. Lysates were resolved on 12% SDS-poly-Acrylamide gels (Invitrogen) and transferred under semi-dry conditions onto polyvinylidene difluoride (PVDF) membrane using Semi-Dry Electroblot Buffer Kit (Owl). Membranes were blocked using Tris Buffered Saline (TBS) containing 0.1% Tween 20 (TBS-T) and 5% non-fat dry milk for 1 hour at room temperature, or overnight at 4° C. All washing stages were carried out using TBS-T. Blots were incubated for 1 hour at room temperature with a 1:2000 dilution of mouse monoclonal anti-IRF5 antibody (M03; Abnova Corp., Taipei City, Taiwan), or a 1:1000 dilution of Goat polyclonal anti-IRF5 antibody (ab2932; Abcam Inc., Cambridge, Mass.). Signals were detected using horseradish peroxidase (HRP) conjugated secondary Abs (1:2000 dilution of rabbit antimouse/goat IgG; Zymed Laboratories, Inc., South San Francisco, Calif.), and ECL chemiluminescence system (Amersham). Membranes also were reprobed with a 1:5000 dilution of rabbit polyclonal anti-GAPDH antibody (sc-154; Santa Cruz Biotechnology, Santa Cruz, Calif.) and a 1:10000 dilution of goat anti-rabbit IgG HRP conjugate (Zymed).

Transient Transfection and mRNA Decay Assay. Tet-Off 293 cells ($1.6 \times 10^6$ cells/mL) were transfected with 3.0 µg of Tet-responsive reporter constructs that encoded chimeric rabbit betaglobin transcripts linked to the 3' UTR of IRF5 that contained either the A or G allele of rs10954213 and with 1 µg of the pTracer-EF/V5-His/lacZ construct (Invitrogen Life Technologies), which produces GFP, to control for transfection efficiency. Transfections were performed with 2.5 U of TransIT-293 reagent (Mirus, Madison, Wis.) per µg of plasmid DNA. After 48 hours, 300 ng/ml of doxycycline was added to stop transcription from the Tet-off constructs. Total RNA was isolated at 0, 1, 3 and 6 hours following doxycycline treatment using the TRIzol® reagent (Invitrogen Life Technologies). RNA was further purified and DNase treated using the RNeasy Mini kit (Qiagen) according to the manufacturer's instructions, and Northern blots were performed. The hybridization intensity of each chimeric beta-globin: IRF5 transcript was normalized to the hybridization intensity of the GFP transcript, and the normalized values were used to calculate transcript half-lives.

Clinical Samples. A collection of family samples of European descent consisting of 555 pedigrees was recruited at the University of Minnesota and at Imperial College, UK (Gaffney et al. (1998) *Proc. Natl. Acad. Sci. USA* 95:14875-14879; Gaffney et al. (2000) *Am. J. Hum. Genet.* 66:547-556; Graham et al. (2006) *Hum. Mol. Genet.* 15:3195-3205; and Graham et al. (2001) *Arthritis Res.* 3:299-305). The following independent European descent case/control populations were studied: 173 unrelated SLE cases from the University of Minnesota, 55 unrelated SLE cases from Imperial College in London, UK, 540 cases from the UCSF Lupus Genetics Project collection (Parsa et al. (2002) *Genes Immunol.* 3 Suppl. 1:S42-S46), and 1439 controls from the NYCP project (Mitchell et al. (2004) *J. Urban Health* 81:301-310). The study also included 338 SLE patients from Sweden, 213 of them recruited at the Karolinska Hospital in Stockholm (Svenungsson et al. (2003) *Arthritis Rheum.* 48:2533-2540) and 125 at Uppsala University Hospital (Sigurdsson et al. (2005) *Am. J. Hum. Genet.* 76:528-537), with 363 healthy, age- and sex matched controls from the same geographical regions as the SLE patients. The SLE patients fulfilled the American College of Rheumatology revised criteria for SLE (Tan et al. (1982) *Arthritis Rheum.* 25:1271-1277). In addition, 270 samples from the International Haplotype Map Consortium ((2005) *Nature* 437:1299-1320), 233 CEPH individuals (14 extended pedigrees, including 21 trios that are part of the HapMap CEU samples, and 38 unrelated individuals) described in Morley et al. ((2004) *Nature* 430:743-747) were genotyped for IRF5 region markers.

Resequencing and genotyping. IRF5 was resequenced in 8 controls and 40 SLE cases collected at Uppsala, Sweden using 23 PCR fragments that covered 1 kb upstream of exon 1a, and all exons and introns. In addition, all exons of IRF5 and 1 kb upstream of exon 1A were resequenced in 96 SLE cases of European descent from the Minnesota SLE cohort. Bidirectional sequencing was conducted using an ABI 3700 and standard methodology. Polymorphisms were identified using Sequencer (Gene Codes Corp) or SNPcompare (de Bakker et al. (2005) *Nat. Genet.* 37:1217-1223), an algorithm that assigns a confidence score to putative SNPs. All putative SNPs were manually verified by examining the traces. All exonic SNPs and SNPs seen in 2 or more samples were validated in the HapMap CEU population.

In the Swedish samples the SNPs were genotyped at the SNP technology platform in Uppsala (available on the World Wide Web at genotyping.se) by multiplex, fluorescent single-base extension using the SNPstream system (Beckman Coulter), with the exception of SNP rs4728142, which was typed by homogeneous fluorescent single-base extension with detection by florescence polarization (Analyst AD, Molecular Probes). The exon 6 deletion was amplified as a 145 bp or 115 bp PCR fragment with primers located in exon 6, and the amplified fragments were separated on 2% agarose gels. The genotype call rate was on average 97.2%, and the accuracy estimated from 5156 genotype comparisons between repeated assays (61% of the genotypes) was 99.3%. The genotypes conferred to Hardy-Weinberg equilibrium (Fisher's exact test, P>0.01). Fragment analysis and the sequencing runs for the Swedish samples were performed by the core facility of the Rudbeck Laboratory in Uppsala, Sweden.

Genotype data in the MN and UK samples were generated using iPLEX and hME chemistries on the Sequenom platform (see Table 10 for assay information). The following quality standards were applied: no more than 1 Mendel error per 100 trios, HWE P>0.001, genotyping completeness>95%, and samples with <75% genotyping were excluded from the analysis. The exon 6 deletion was genotyped by amplifying the region using primers listed in Table 10 at an annealing temperature of 63° C. Fragments were separated using a 4% agarose gel (E-Gel 48, Invitrogen). All allele calls were made independently by two individuals blinded to sample ID.

Expression analysis in EBV cell lines. Normalized IRF5 mRNA expression levels were obtained from data made available by the GENEVAR project at the Sanger Centre from EBV transformed B-cells derived from the 270 HapMap samples (IRF5 exon 9 probe GI_38683858-A). In addition, IRF5 expression values (probeset 205469_s_at) were obtained from a dataset of 233 CEPH EBV transformed B cell lines (Cheung et al. (2005) *Nature* 437:1365-1369; GEO accession number GSE1485). Association of genotype to IRF5 expression levels and conditional logistic regression analyses were conducted using WHAP (available online at pngu.mgh.harvard.edu/purcell//whap).

Association analysis. Family-based and case/control association analyses, including permutation testing, were conducted using Haploview v3.3 (Barrett et al. (2005) *Bioinformatics* 21:263-265). Single marker association results for the population-based cohorts are shown in Table 11. Conditional logistic regression analyses of single markers and haplotypes was performed using the WHAP software program. Haplotypic association results in the family-based US and UK cohort, the case-control cohort collected in the US and UK and the Swedish case-control cohort were combined using the Mantel-Haenszel meta-analysis of the odds ratios (ORs) (Lohmueller et al. (2003) *Nat. Benet.* 33:177-182; and Woolson and Bean (1982) *Stat. Med.* 1:37-39).

Expression Analysis in Whole Blood. Total RNA was isolated from whole blood drawn into PAXgene tubes from 38 independent Caucasian SLE cases (Affymetrix 133A chips, IRF5 probe set 205469_s_at). The analysis included 23 patients that were AA at the rs10954213 SNP (17 TT and 6 GT at rs2004640), 11 patients that were GA at rs10954213 (8 GT and 3 GG at rs2004640), and 4 patients that were GG at rs10954213 (1 GT and 3 GG at rs2004640).

Characterization of Sequence Variation at IRF5

To more fully characterize genetic variation at IRF5, the exons and 1 kb upstream of the IRF5 exon 1A were sequenced in DNA from 136 cases of SLE. Each of the introns in 40 SLE cases and 8 controls also were sequenced (Tables 12 and 13). In total, 52 variants were observed, of which 32 were novel, while 20 had been previously identified (present in dbSNP). Of the novel variants, 13 had minor allele frequency greater than 1%. Each such variant was genotyped in the HapMap CEU samples, allowing them to be integrated with data from the International HapMap Project.

While no common single nucleotide missense variants of IRF5 were observed, a 30 bp inframe insertion/deletion (indel) in exon 6 was observed. The exon 6 indel is located in a proline-, glutamic acid-, serine- and threonine-rich (PEST) domain, a motif previously shown to influence protein stability and function in the IRF family of proteins (Levi et al. (2002) *J. Interferon Cytokine Res.* 22:153-160). TagSNPs were selected to serve as proxies ($r^2$>0.8) for all SNPs with minor allele frequency>1% in the combined data from HapMap Phase II ((2005) *Nature* 437:1299-1320) and genotype data in the same samples for the SNPs discovered in the sequencing effort.

Association of Common Variation in IRF5 to Risk of SLE

Each tagSNP was individually tested for association to SLE in a combined trio and family collection of 555 families from the US and the UK (Table 14). The strongest association with SLE was for three highly correlated SNPs (rs2070197, rs10488631, and rs12539741, pairwise $r^2$>0.95). These SNPs (referred to herein as "Group 1") do not include the exon 1B splice site variant (rs2004640) described above, and showed highly significant association: Transmitted/Untransmitted (T/U) ratio=1.8; P=1.2×10$^{-7}$. To assess whether the Group 1 variants could explain the association to SLE, conditional logistic regression incorporating one of the Group 1 SNPs (rs2070197) was performed. This model was rejected, because a second set of correlated SNPs (rs729302, rs4728142, rs2004640, and rs6966125; referred to herein as Group 2) were independently associated with risk to SLE (P<0.002-0.008, Table 11). Group 2 includes rs2004640.

To test the hypothesis that the combination of Group 1 and Group 2 variants fully account for the association observed to SLE, the conditional logistic regression analysis was repeated, including a Group 1 and a Group 2 variant in the model (represented by rs2070197 and rs2004640, respectively). A third set of six highly correlated SNPs (rs4728142, rs3807135, rs752637, rs10954213, rs2280714, and rs17166351; referred to as Group 3) was associated with risk of SLE (p<0.001-0.01; Table 11). These results indicate that three independent sets of correlated IRF5 variants (Groups 1, 2, and 3) each provide statistically independent evidence for association with risk of SLE. Thus, while the exon 1B splice site (rs2004640) has been shown to be strongly associated with SLE, it is clear that rs2004640 does not explain all of the effect of IRF5 on risk to SLE—indeed, it is not even the strongest contributor. As such, experiments were conducted to identify other putative functional alleles that might explain the independent signals of association observed for Groups 1 and 3.

Cis-Acting Alleles Underlying Variation in IRF5 Expression

One approach to finding causal alleles is to examine other phenotypes that might be less complex in their inheritance, providing power to distinguish the effects of highly correlated alleles, and offer in vitro assays to assess function. In vitro expression levels provide one such phenotype. Given the previous observation that one of the Group 3 variants (rs2280714) is associated with levels of IRF5 mRNA expression, the more complete set of IRF5 variants was systematically examined for alleles that might be associated to levels of IRF5 mRNA expression in lymphoblastoid cell lines.

The same set of tagSNPs genotyped in the SLE family cohort was studied in the HapMap samples, allowing correlation of genotype to mRNA expression data collected at the Sanger Institute (on the World Wide Web at sanger.ac.uk/humgen/genevar/). A variant in the 3' UTR (rs10954213, Group 3) showed the strongest association with IRF5 expression: P=3.5×10$^{-55}$ (Table 14). This variant and one other (rs10954214) reside in conserved elements within the 3' UTR, a region that often contains sequences that influence mRNA expression (Conne et al. (2000) *Nat. Med.* 6:637-641).

Figure 7:
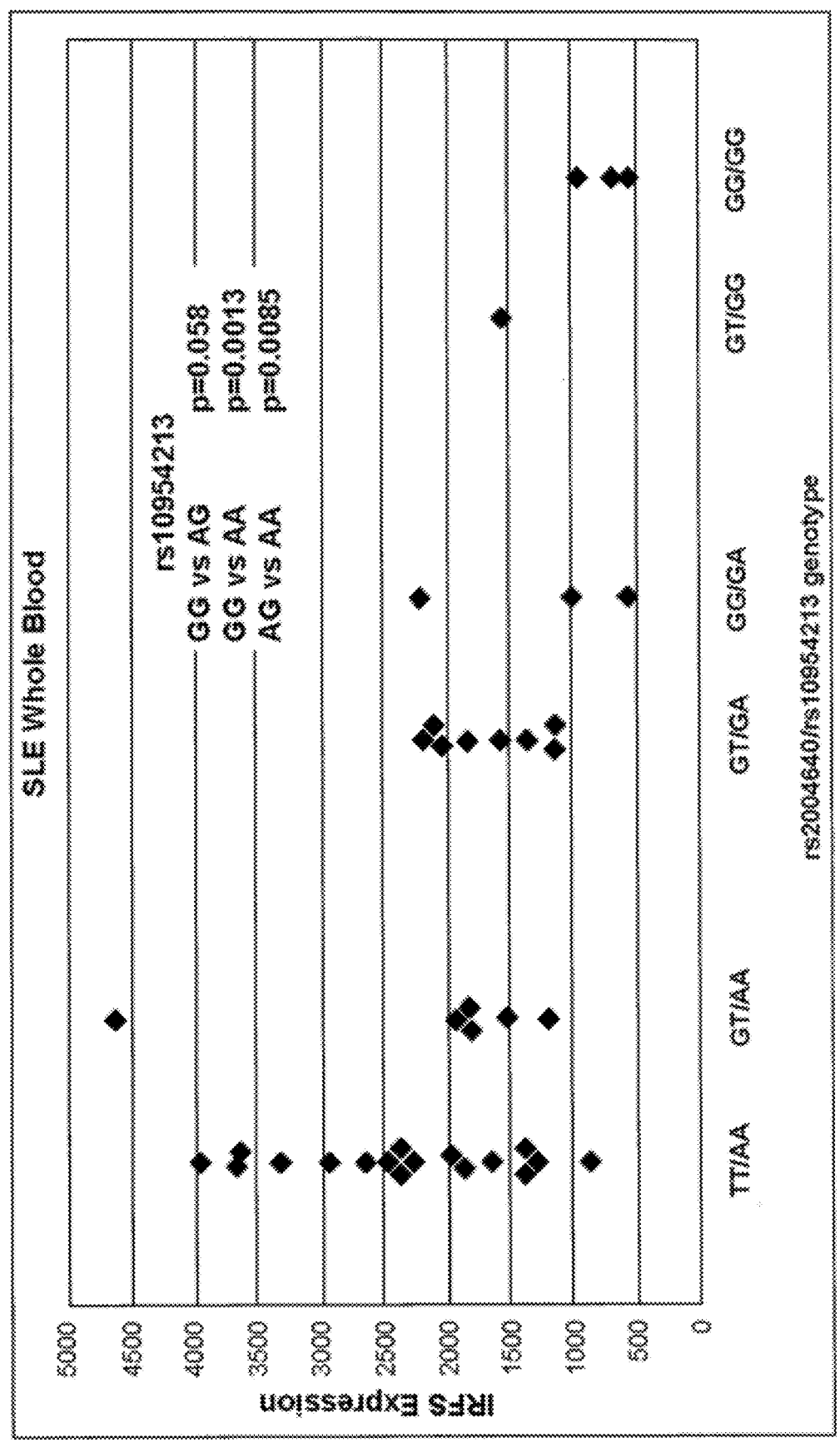
FIG. 7 is a graph plotting microarray expression levels of IRF5 in whole blood RNA samples from SLE patients. Each symbol represents the expression level in a single patient.

To increase the power to distinguish effects of correlated SNPs, a subset of the associated IRF5 variants was genotyped in an independent dataset in 233 CEPH samples for which microarray gene expression data was publicly available (Morley et al., supra) (Table 15). Again, rs10954213 was the best predictor of IRF5 expression. Specifically, rs10954213 showed stronger association than either the neighboring rs10954214 or the rs2280714 SNP studied previously (Table 15, FIG. 7). Formally, rs10954213 remained strongly associated with IRF5 mRNA levels after conditioning on rs2280714 (P=5×10$^{-9}$), while conditioning on rs10954213 nearly eliminated association of rs2280714 to IRF5 expression (P=0.004). Finally, similar findings were observed for expression of IRF5 in whole blood of SLE cases (FIG. 7).

These results indicated that rs10954213 was the best predictor of IRF5 expression in this survey of lymphoblastoid cell lines, clearly distinguishable in its effect from the other SNPs with which it is in strong linkage disequilibrium. As rs10954213 also is a member of Group 3, it became a candidate to explain the association of Group 3 SNPs to SLE. It is noted that the greater strength of the signal of association of IRF5 expression levels ($P<10^{-55}$) allowed the signal of rs10954213 to be distinguished from the other members of Group 3 for IRF5 expression. The weaker signals of association to risk of SLE were not able to be clearly distinguished.

Figure 6:
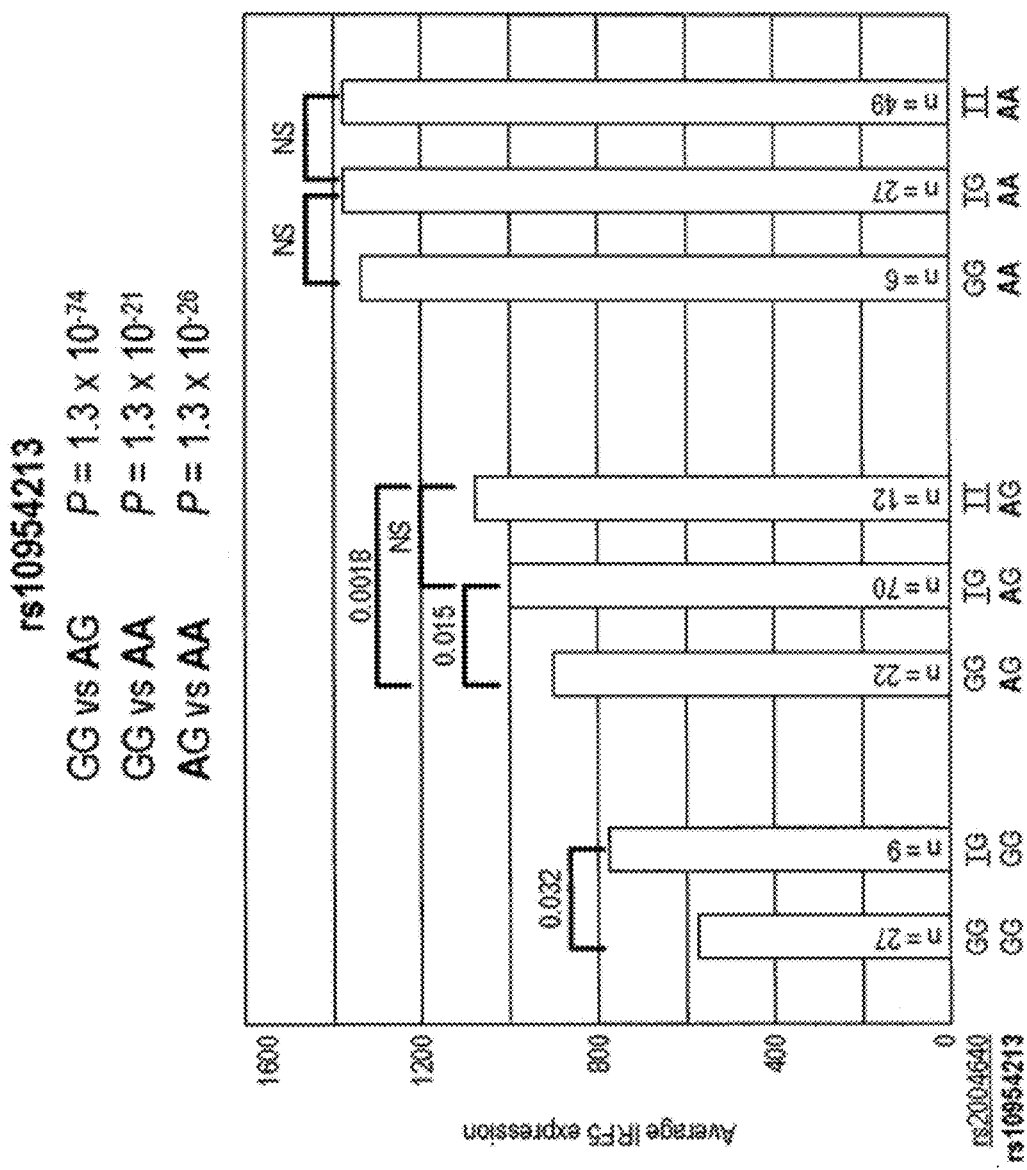
FIG. 6 is a graph plotting expression levels of IRF5 mRNA in CEU cell lines carrying various genotypes for rs2004640 and rs10954213.

While rs10954213 was the strongest determinant of IRF5 expression in the survey of common variation at IRF5, conditioning on this SNP did not account for all variance in IRF5 expression. After conditioning on rs10954213, the exon 1B splice site (rs2004640) and other linked SNPs were the next strongest association to IRF5 levels (Table 15). Specifically, the presence of the T allele at rs2004640, which allows expression of exon 1B isoforms, was associated with significantly higher levels of IRF5 expression in cell lines carrying GG or AG genotype at rs10954213 (FIG. 6). After incorporating a two-locus model of both rs10954213 and rs2004640, no other SNP has a nominally significant association to IRF5 expression in the CEU cell lines (Tables 15 and 16).

Thus, the systematic search for a common variation that influences levels of IRF5 mRNA led to identification of rs10954213, a SNP in a conserved element within the 3' UTR and a member of Group 3, as well as the exon 1B splice site variant (rs2004640), a member of Group 2.

A Group 3 Variant Alters a Polyadenylation Signal and Influences IRF5 Expression While the data described in Example 1 show that the exon 1B SNP influences IRF5 mRNA levels through its effect on splicing (Graham (2006) *Nat. Genet.* (38:550-555), the function, if any, of rs10954213 was unknown. The sequence surrounding rs10954213 has been highly conserved throughout evolution. Moreover, the rs10954213 G allele is predicted to disrupt a polyA$^+$ signal sequence (AAUAAA→AAUGAA) located 552 bp downstream of the stop codon of IRF5 in the 3' UTR region of exon 9. The canonical motif is a binding site for a protein complex known as cleavage and polyadenylation specificity factor (CPSF). During RNA polymerase II transcription, CPSF binds to the AAUAAA sequence and is part of a complex that cuts the mRNA strand 10-30 bp downstream of the polyA$^-$ signal and initiates polyadenylation of the transcripts (Edmonds (2002) *Prog. Nucl. Acid. Res. Mol. Biol.* 71:285-389).

Figure 8:
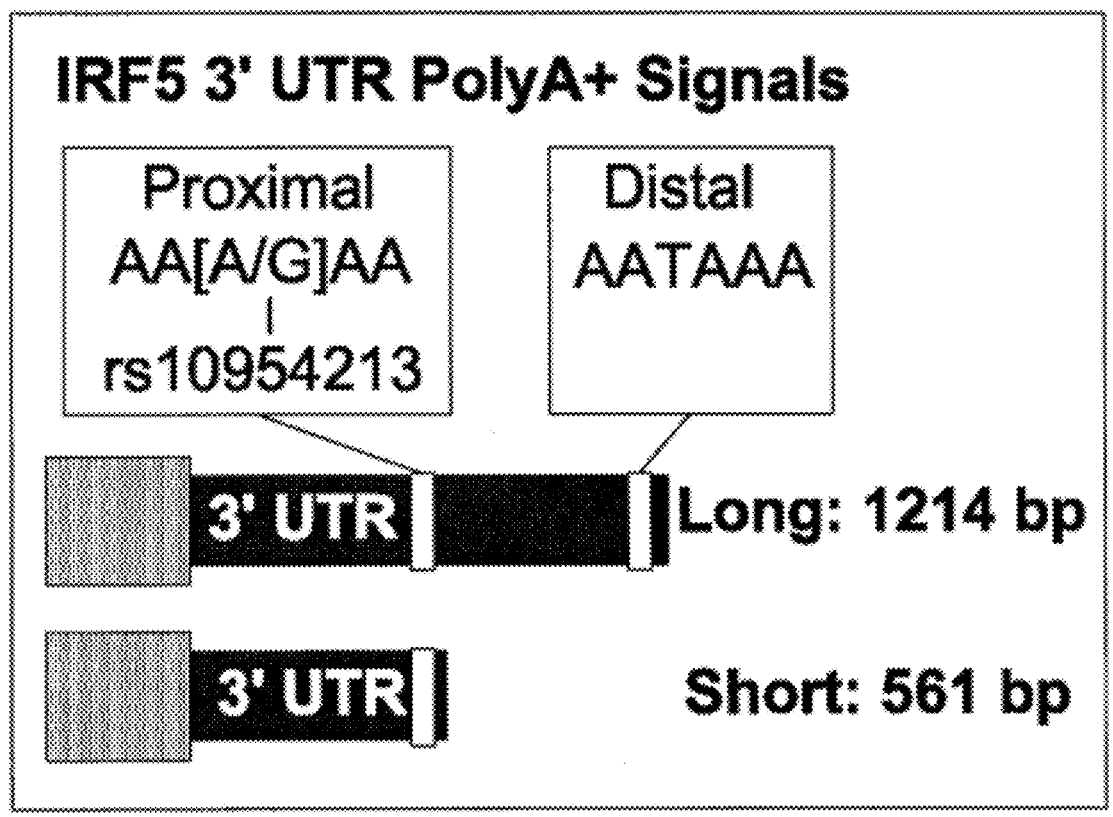
FIG. 8 is a schematic of the 3' UTR region of IRF5.

Based on the location of rs10954213 in a conserved CPSF site, it was hypothesized that the different alleles of rs10954213 might influence polyadenylation, and thereby the length and stability of the IRF5 message. Specifically, the A allele of rs10954213 might allow efficient polyadenylation approximately 12 bp downstream, while the G allele favors the use of a distal polyA$^+$ site 648 bp downstream (FIG. 8).

Figure 9:
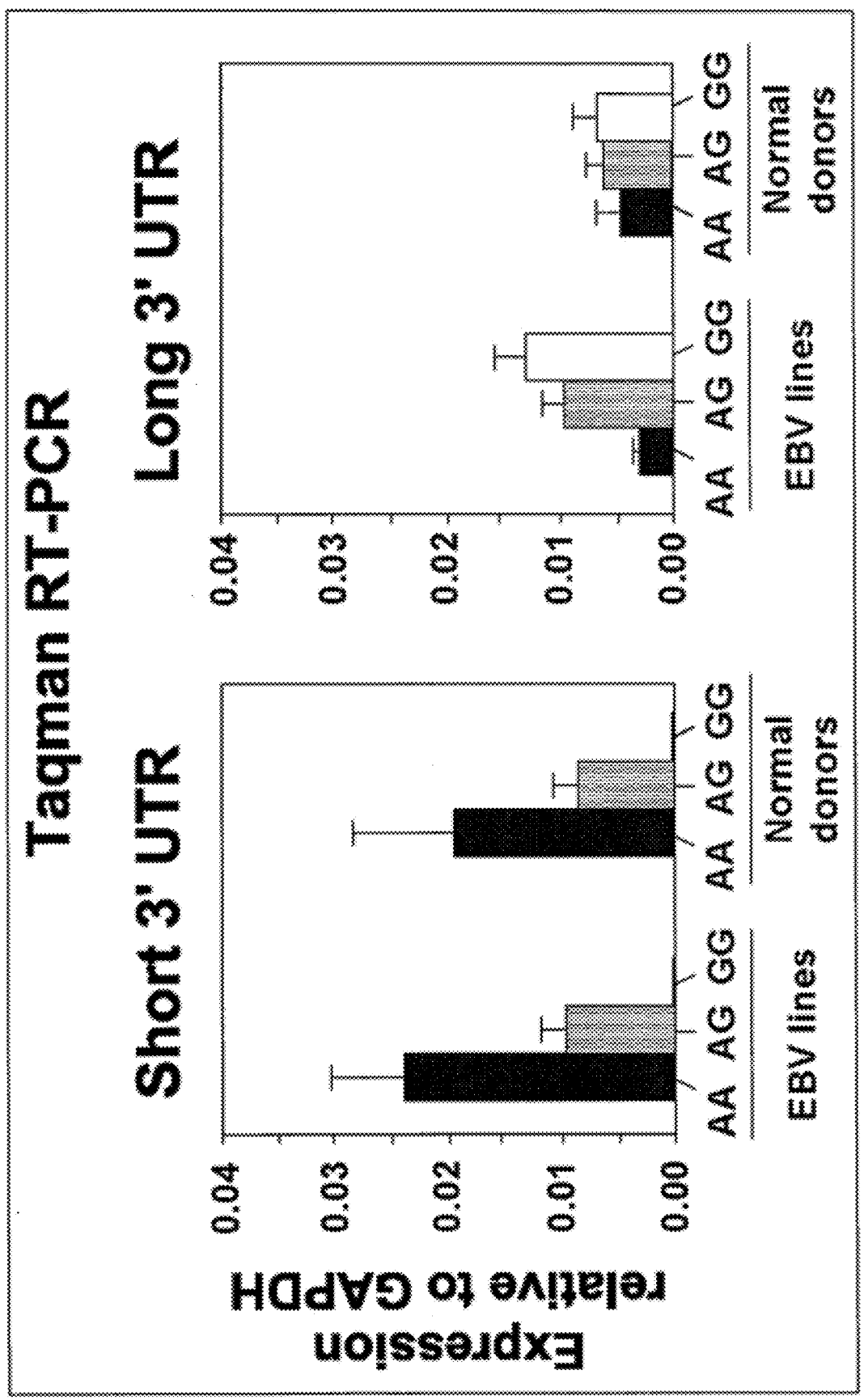
FIG. 9 is a pair of graphs plotting levels of IRF5 isoforms carrying the short (left panel) or long (right panel) 3' UTR, as determined by quantitative TaqMan RT-PCR in EBV cell lines (N=9) and in control PBMCs (N=14).

To directly test this hypothesis, Northern blotting and quantitative PCR were performed using IRF5 mRNA from cell lines and PBMC of known genotype at rs10954213, as well as chimeric mRNAs that attach the two alleles of the 3' UTR to heterologous expression constructs. Total and polyA$^+$ enriched RNA were isolated from the HapMap CEU population, selecting individuals based on genotype at rs10954213. Northern blotting of polyA$^+$ RNA showed that cell lines homozygous for the A allele at rs10954213, carrying the wild-type AAUAAA on both alleles, expressed mainly a short version of IRF5 mRNAs. In contrast, cell lines homozygous for the G allele (AAUGAA) expressed almost exclusively a longer mRNA that utilized the second downstream polyA$^+$ site. AG heterozygote cell lines showed expression of both isoforms. Identical results were obtained in Northern blots of total RNA isolated from the cell lines. These results were confirmed with TaqMan quantitative PCR assays in both EBV-transformed cell lines and normal donor PBMCs (FIG. 9). These data confirmed that the allele at rs10954213 determines the site of polyadenylation. Thus, rs10954213 is referred to hereafter as the polyA$^+$ variant, with the A allele termed the "short" allele, and the G allele the "long" allele.

Figure 10:
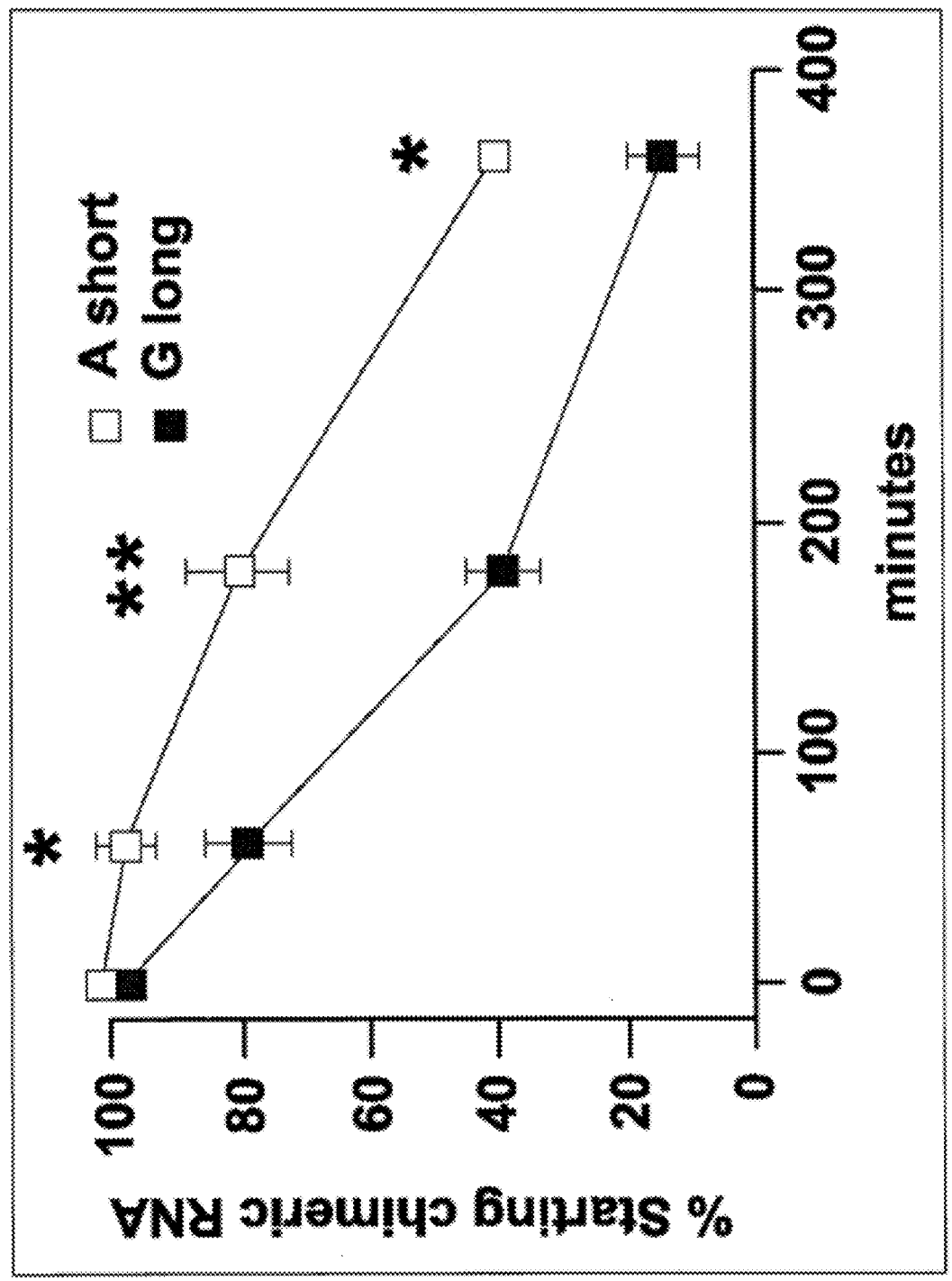
FIG. 10 is a graph plotting the decay of beta-globin 3' IRF5 UTR mRNAs following suppression of new transcription with doxycycline. Results represent 4 independent experiments. *P<0.05; **P<0.01.

To determine whether the long allele of the 3' UTR might be unstable, the two versions of the 3' UTR downstream from the coding region of rabbit beta-globin were cloned, and 293 'Tet-off' kidney cells were transfected with expression plasmids driving chimeric cDNAs carrying either the short or long allele. Northern blotting of mRNA isolated 48 hours after transfection showed that chimeric cDNAs used the expected polyA$^+$ site, and that the long mRNAs had a shorter half-life than short chimeric transcripts (FIG. 10). Estimates for the half-life of these transcripts, based on regression curves, were 342±88 min for the short allele, and 125±21 min for the long allele. By comparison, the calculated half-life of beta-globin mRNA alone (lacking the IRF5 3' UTR) was 11,631±1,574 min. These experiments document that disruption of the proximal polyA$^+$ signal by rs10954213 leads to transcription of long and relatively unstable IRF5 mRNA transcripts. These effects on IRF5 mRNA are reflected in levels of IRF5 protein, as shown by Western blots of whole cell lysates from EBV cell lines carrying the various polyA$^+$ SNP genotypes: cells carrying the AA genotype showed ~5-fold higher levels of immunoreactive IRF5 protein than cells carrying the GG genotype.

The Exon 6 Indel and Risk of SLE

The experimental results discussed herein suggest that (a) the association of Group 2 SNPs to SLE is likely explained by the exon 1B splice site allele (rs2004640), and (b) the association of the Group 3 SNPs is likely due to the polyA$^+$ variant (rs10954213). In contrast, none of the Group 1 SNPs were found to alter the coding region of IRF5, lie in evolutionarily conserved regions, or change an annotated sequence motif. This suggests either that the Group 1 SNPs (or an undiscovered but strongly linked mutation) have an as yet unrecognized effect on IRF5 function, or that the Group 1 SNPs have no functional consequence but instead tag a combination of other functional variants in IRF5.

Figure 11:
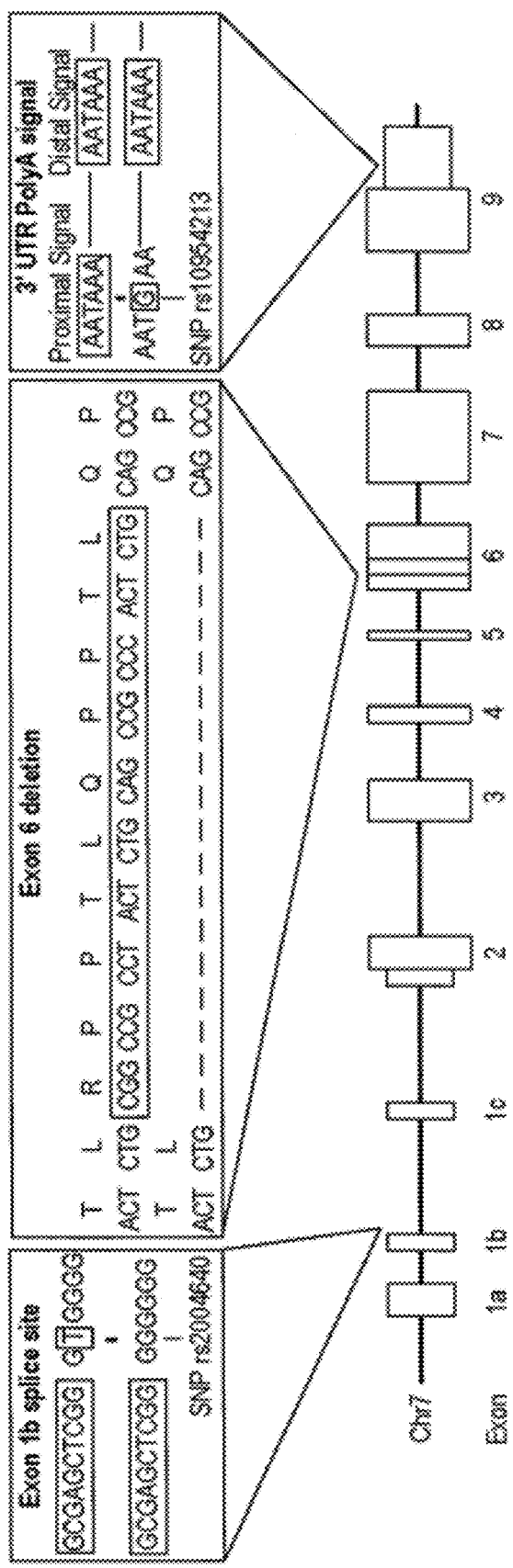
FIG. 11 is a diagram showing the location of the three common functional alleles identified in IRF5. The exon 1b splice site is shown on the left [rs2004640; variant sequence (top), SEQ ID NO:253; wild type sequence (bottom), SEQ ID NO:254]. The exon 6 insertion/deletion is shown in the center [amino acid sequence with insertion (top), SEQ ID NO:255; nucleic acid sequence with insertion (second line), SEQ ID NO:256; nucleic acid sequence with deletion (third line), SEQ ID NO:257; amino acid sequence with deletion (bottom), SEQ ID NO:258]. The 3' untranslated region (UTR) polyA signal (rs10954213) is shown on the right.

To assess the second model (having found no evidence for a functional allele among the Group 1 SNPs), the conditional logistic regression analysis was performed not in order of statistical significance (as above), but instead starting with the two putative functional alleles identified above (exon 1B splice site variant and polyA$^+$ variant). Multiple variants were observed that showed significant association to SLE in this analysis (Table 11), including the 30 bp in-frame insertion/deletion (indel) polymorphism that was discovered within exon 6 (FIG. 11). This indel is located in a PEST domain known to influence stability and function of the IRF family of proteins. Previous studies have shown that IRF5 protein isoforms which, in part, differ by the 30 bp (10aa) exon 6 indel (which had previously been observed in cDNA, but not recognized to be a germline polymorphism) have differential ability to initiate transcription of IRF5 target genes (Barnes et al. (2004) *J. Biol. Chem.* 279:45194-45207; Mancl et al.

(2005) *J. Biol. Chem.* 280:21078-21090; and Barnes et al. (2002) *Mol. Cell. Biol.* 22:5721-5740).

It is noted that association of the exon 6 indel to SLE was only observed when conditioned on the exon 1B splice site and polyA+ variants. The association previously had been masked by the signal of the Group 1 variants in the initial analysis that proceeded in order of statistical significance. Consistent with a model in which the three putative functional alleles (exon 1B, polyA+, and exon 6 indel) are sufficient to explain the observed association to SLE, however, a logistic regression that includes these three variants revealed no additional SNP with p<0.01. That is, the effect of Group 1 SNPs is statistically indistinguishable from their linkage disequilibrium with the three alleles that have putative functional effects on the structure of IRF5 protein and/or its expression.

Haplotype Analysis Identifies Three Levels of SLE Risk

To better understand the observed combinations of the three putative functional alleles (and the Group 1 SNPs), the four marker haplotypes defined by: (a) the exon 1B splice site (rs2004640, Group 2), (b) the polyA+ variant (rs10954213, Group 3), (c) the exon 6 indel, and (d) Group 1 (using rs2070197 as a proxy) were examined (Table 17). These four variants defined five common haplotypes, each carrying unique combinations of the exon 1B splice site, the exon 6 indel, and the polyA+ variant.

These haplotypes were studied for association to SLE in large family-based and case-control samples totaling 2,188 case and 3,596 control chromosomes. Haplotype 1 (Table 17) was strongly associated with risk of SLE, appearing on 19.0% of SLE chromosomes in comparison to 11.9% of control chromosomes (P=1.4×10$^{-19}$, Table 17). In the case-control sample, a single copy of haplotype 1 was associated with an odds ratio (OR) of 1.46, while two copies were associated with an OR of 2.96 (Table 18). No other IRF5 haplotypes showed positive association with SLE. The high-risk haplotype 1 is predicted to be the only haplotype with the ability to express exon 1B isoforms (due to rs2004640), carries the exon 6 insertion, and is expressed at high levels due to the polyA+ variant.

Figure 12:
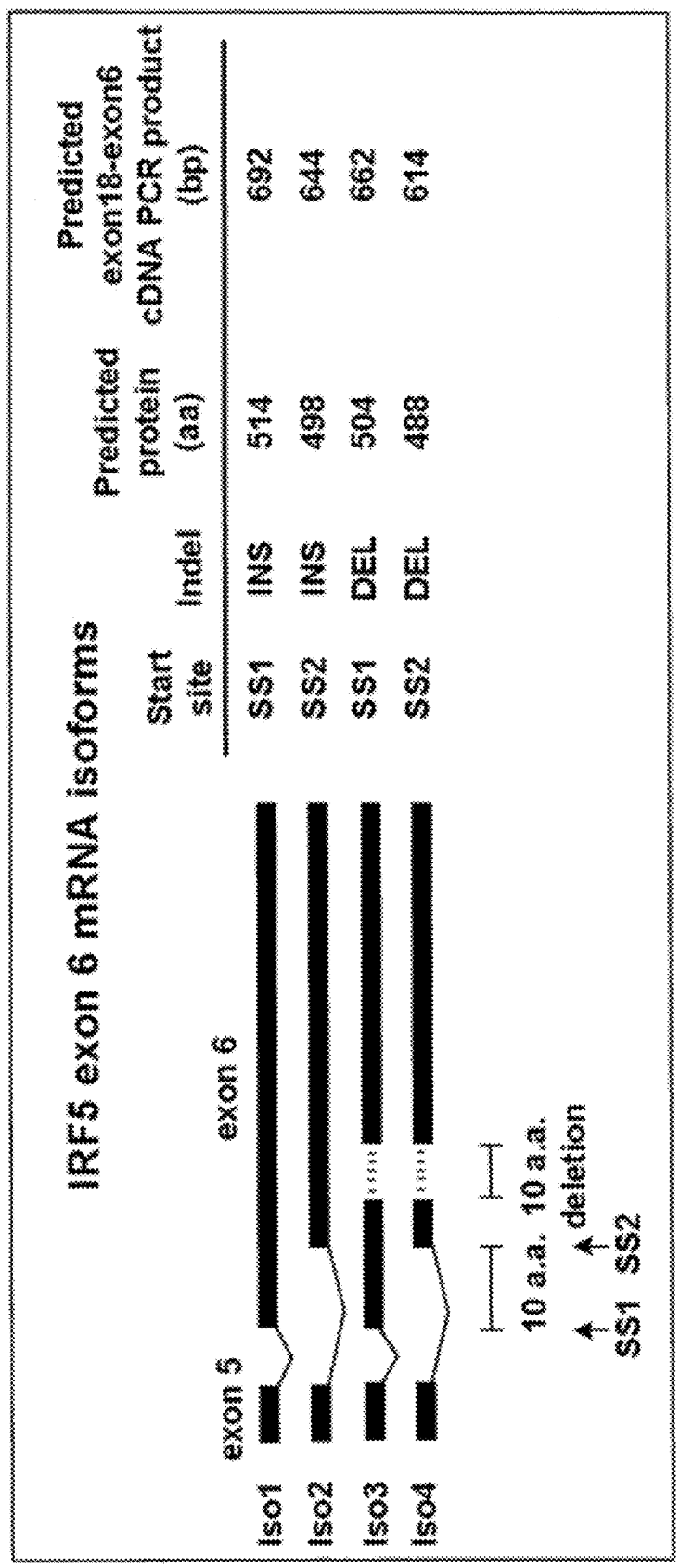
FIG. 12 is a diagram showing IRF5 exon 6 mRNA isoforms determined by the common indel and two alternatively spliced exon 6 start sites (SS1 and SS2). The expected full-length protein isoform lengths in amino acids (aa) are noted. The predicted lengths of PCR fragments from an exon 1B primer site to a region just downstream of the exon 6 indel are shown for each of the isoforms.

Alternative proximal splice acceptors for exon six, termed SS1 and SS2, which are proximate to the exon 6 indel, have been shown to influence activation of downstream genes (Barnes et al. (2004), supra; Mancl et al., supra; and Barnes et al. (2002), supra). As shown in FIG. 12, both SS1 and SS2 are used regardless of the exon 6 indel genotype.

While haplotypes 2 and 3 showed no evidence for association to SLE as compared to the overall population (OR=1.09 and 0.95, P>=0.05, respectively), haplotypes 4 and 5 showed strong evidence for protection. Specifically, each was associated with a ~25% reduction in risk (OR=0.76) that was statistically highly significant (P<5×10$^{-8}$ and 3×10$^{-5}$, respectively). Moreover, individuals that carry haplotype 1 in trans with either of the haplotypes that lack exon 1B isoform expression (4 and 5) show a reduction in risk of SLE (Table 18).

Frequency of IRF5 Haplotypes in World Populations

The Human Genome Diversity Panel was genotyped to assess the frequency of IRF5 alleles in world populations, and genotype data was submitted to the Human Genome Diversity panel (HGDP) database (Rosenberg et al. (2002) *Science* 298:2381-2385; and Cann et al. (2002) *Science* 296:261-262). It was noted that high-risk haplotype 1 is common in a European-derived population, but rare in West-African and East-Asian HapMap populations (15% in CEU, 0% in YRI, <1% in JPT/HCB). Extending these observations into a broader array of populations in the HGDP revealed that haplotype 1 is found in Central Asia and derived populations (European and Native American), but is rare in other world populations (Table 19). Haplotype 1 was examined for evidence of recent rapid positive selection using extended haplotype homozygosity algorithms (Sabeti et al. (2002) *Nature* 419:832-837; and Walsh et al. (2006) *Hum. Genet.* 119:92-102), but there was no evidence for selection.

In summary, these data reveal that the highest risk for SLE is observed with a haplotype that is predicted to express at high levels of transcripts containing exon 1B and the exon 6 insertion (FIG. 13). Haplotypes 2 and 3, which carry only 2 of the 3 risk associated functional alleles, show average risk to SLE. Haplotypes 4 and 5, which carry only 1 of the 3 risk associated functional alleles—and, in particular, lack exon 1B isoforms—are protective for SLE.

TABLE 10

Assay Information

| Assay Name | Forward Primer (SEQ ID NO:) | Reverse Primer (SEQ ID NO:) | Extension Primer/Probe (SEQ ID NO:) | Platform | Samples |
| --- | --- | --- | --- | --- | --- |
| Genotyping assays used in US and UK cohorts | | | | | |
| rs2070197 | AGCGGATAACAGACAGC CCAGGAGAGAAAG (28) | AGCGGATAACTCCTACC TCTGGGTTTCCTG (29) | TCTCCTTCTTGGCCCA (30) | Sequenom iPlex | HapMap, HGDP, MN and UK SLE cohorts |
| rs10488631 | AGCGGATAACATTCACTG CCTTGTAGCTCG (31) | AGCGGATAACGTCTATC AGGTACCAAAGGC (32) | AGCTCGGAAATGGTTC (33) | Sequenom iPlex | HapMap, HGDP, MN and UK SLE cohorts |
| rs2004640 | AGCGGATAACTCCAGCT GCGCCTGGAAAG (34) | AGCGGATAACAGGCGC TTTGGAAGTCCCAG (35) | GGAAAGCGAGCTCGGG (36) | Sequenom iPlex | HapMap, HGDP, MN and UK SLE cohorts |

TABLE 10-continued

| rs960633 | AGCGGATAACTTCCTGCT ACTGTTAGTCCC (37) | AGCGGATAACTCACAGA TCTGCAGACATGG (38) | CTCAACATTCCTTGCTG (39) | Sequenom iPlex | HapMap, HGDP, MN and UK SLE cohorts |
|---|---|---|---|---|---|
| rs2280714 | AGCGGATAACTGGACTG AGAGAATGAACGG (40) | AGCGGATAACGCTTTCT ATCGTGGTCACAT (41) | taTGACCCTGGCAGGTCC (42) | Sequenom iPlex | HapMap, HGDP, MN and UK SLE cohorts |
| rs11761242 | AGCGGATAACACCTCATT CTGAAGTCTGCC (43) | AGCGGATAACTTAAAGC AGTAGCTCCCTTG (44) | AAAGTCTGGCGTTTTAAC (45) | Sequenom iPlex | HapMap, HGDP, MN and UK SLE cohorts |
| rs4728142 | AGCGGATAACCCTTCCTC CCCATTTCTTAC (46) | AGCGGATAACAGGTGTC CATGTAACAGTGC (47) | CCCCATTTCTTACTAACAC (48) | Sequenom iPlex | HapMap, HGDP, MN and UK SLE cohorts |
| rs6948542 | AGCGGATAACCTCATCTC TACTGGAGATGG (49) | AGCGGATAACCCTCGTC TGCAGGTCCTTAT (50) | CCTGCTATTCCATCTCCTTC (51) | Sequenom iPlex | HapMap, HGDP, MN and UK SLE cohorts |
| rs6966125 | AGCGGATAACCCAGCCA GGAAGCAATTCTT (52) | AGCGGATAACTTGAATC CTTGGCTGTAGGC (53) | ATTCTTAATATGCTTGCCTT (54) | Sequenom iPlex | HapMap, HGDP, MN and UK SLE cohorts |
| rs4731523 | AGCGGATAACATCTTTAC TGCCCTAGGGTG (55) | AGCGGATAACGTCACAG GCTTCAGCTAGG (56) | ATTACAGTAAGAAAAAGCCC (57) | Sequenom iPlex | HapMap, HGDP, MN and UK SLE cohorts |
| rs729302 | AGCGGATAACTGGACTCT GGTGTGTAGGTG (58) | AGCGGATAACGAAATAG ACCAGAGACCAGG (59) | aTGGTGTGTAGGTGATCCTG (60) | Sequenom iPlex | HapMap, HGDP, MN and UK SLE cohorts |
| rs6968225 | AGCGGATAACTCCTCACA GCACCATAAGTC (61) | AGCGGATAACAGCAGCA GCTGCCATTCCAT (62) | ggCCACCCCACTGTTTAGAGG (63) | Sequenom iPlex | HapMap, HGDP, MN and UK SLE cohorts |
| rs12539741 | AGCGGATAACAATTCATA CCTCCTGCCCTG (64) | AGCGGATAACACCCTCC AGATGTAATGAGC (65) | ccACCTCCTGCCCTGGTCAAAA (66) | Sequenom iPlex | HapMap, HGDP, MN and UK SLE cohorts |
| rs11770589 | AGCGGATAACCCTTTTAC TACTACCAGTTGC (67) | AGCGGATAACCCAGTTG GCATCCGAAACAG (68) | cACTACCAGTTGCTCCCATGCT (69) | Sequenom iPlex | HapMap, HGDP, MN and UK SLE cohorts |
| rs10954213 | AGCGGATAACGAAAGAAA CAGCTGAGTCTG (70) | AGCGGATAACCTTGAGA GTCCAAGAACCTG (71) | gGCTGAGTCTGTTTTAACATT (72) | Sequenom iPlex | HapMap, HGDP, MN and UK SLE cohorts |
| rs1874328 | AGCGGATAACGCTAAACC TGCACATAGGAC (73) | AGCGGATAACACCCTCA CCTCACCTAATTG (74) | CAGGCTCGAGACACTGGAGCT G (75) | Sequenom iPlex | HapMap, HGDP, MN and UK SLE cohorts |
| rs1495461 | AGCGGATAACGTGGCTT CCGACTTCTGGT (76) | AGCGGATAACAAAAGGA ACATTGAGGGCGG (77) | tCTTCCGACTTCTGGTCTTTAT G (78) | Sequenom iPlex | HapMap, HGDP, MN and UK SLE cohorts |
| rs17166351 | AGCGGATAACCCGGCCT TTGTAAACAAAATC (79) | AGCGGATAACGTAGGCT GCTACAACAACAC (80) | gGAGGAAACTTATGAGAGCCG TA (81) | Sequenom iPlex | HapMap, HGDP, MN and UK SLE cohorts |
| rs10954214 | AGCGGATAACGGCCTTC ATAAACACTCACC (82) | AGCGGATAACATTCCAC ACCCTTGCTTCAG (83) | AAACACTCACCTGGCTGGCTT TGC (84) | Sequenom iPlex | HapMap, HGDP, MN and UK SLE cohorts |

TABLE 10-continued

| | | | | | |
|---|---|---|---|---|---|
| rs7780972 | AGCGGATAACTAGGGTC CGGATTAGAAGTG (85) | AGCGGATAACGAAGAGT AATTTGCCCCCTG (86) | tgAGAAGTGTACACCCTTATTC TA (87) | Sequenom iPlex | HapMap, HGDP, MN and UK SLE cohorts |
| rs3847098 | AGCGGATAACGGTGAAT GTTTCAGTTCTGG (88) | AGCGGATAACTGGTTTC CTGGTGAACTTTC (89) | cccTCTGTTTAGTCTTCCTTTTT TT (90) | Sequenom iPlex | HapMap, HGDP, MN and UK SLE cohorts |
| rs7808907 | AGCGGATAACTCCATATA CACACATGTGC (91) | AGCGGATAACCTGTGCT CTCTCCAATAATC (92) | gatCAAAAACTATTATGCGAGG TAC (93) | Sequenom iPlex | HapMap, HGDP, MN and UK SLE cohorts |
| rs3807135 | AGCGGATAACACTGTGTT CTAGGGCGAGAG (94) | AGCGGATAACACACAAA TGAGGGCGCAGTG (95) | CACCCTCGCCAGGGGTG (96) | Sequenom iPlex | HapMap, HGDP, MN and UK SLE cohorts |
| rs9656375 | AGCGGATAACCTGATGTC TAATAGGCCCTG (97) | AGCGGATAACAGCATTT CACGGCAGGAAAG (98) | TCAGGGTGGTAGGGACA (99) | Sequenom iPlex | HapMap, HGDP, MN and UK SLE cohorts |
| rs10488630 | AGCGGATAACGGGAGTT GGGTTACTCTTTC (100) | AGCGGATAACCAGGTCA GGAAACTGTCTAC (101) | TCAGTTAAACAGTGTGGTA (102) | Sequenom iPlex | HapMap, HGDP, MN and UK SLE cohorts |
| rs752637 | AGCGGATAACTTTTCCCC TGTACCCTGGTC (103) | AGCGGATAACGCAAAAG GTGCCCAGAAAGA (104) | ACCCTGACCCTGGGAGGAAG C (105) | Sequenom iPlex | HapMap, HGDP, MN and UK SLE cohorts |
| rs2935017 | ACGTTGGATGAGCAGGG GGACCCAGCACCA (106) | ACGTTGGATGATGTCAA GTGGCCGCCCA (107) | CCAGCACCACGGGCGGC (108) | Sequenom iPlex | HapMap, HGDP, MN and UK SLE cohorts |
| IRF5_exon6_indel | CTCAAAGAGGATGTCAAG TGG (109) | GGCTGGGGTCTGGAGC AG (110) | NA | 4% Agarose Gel | HapMap, MN and UK SLE cohorts |
| Genotyping assays used in Swedish cohort | | | | | |
| rs10954213 | TACCCCCTTCTTGAGAGT CC (111) | ATGGGAGCAACTGGTAG TAGTAAA (112) | AGCGATCTGCGAGACCGTATA ATTTTTATGTATTTTTGGATTAA T (113) | SNPstream | Swedish SLE case_controls |
| rs2004640 | GAGGCGCTTTGGAAGTC C (114) | ATGAAGACTGGAGTAGG GCG (115) | GGATGGCGTTCCGTCCTATTG CGCACCCTGCTGTAGGCACCC (116) | SNPstream | Swedish SLE case_controls |
| rs2070197 | AGCGGATAACAGACAGC CCAGGAGAGAAAG (117) | AGCGGATAACTCCTACC TCTGGGTTTCCTG (118) | CCCTCTCCTTCTTGGCCCA (119) | FP_TDI | Swedish SLE case_controls |
| Ex6_indel30 | CCCCACATGACACCCTAT TC (120) | GGCTGGGGTCTGGAGC AG (121) | | 2% agaorose gel | Swedish SLE case_controls |
| IRF5 sequencing primers used in US SLE cases | | | | | |
| IRF5_e01_a0 01_0-100 | AGGTACGGGGTTGTCAA ATG (122) | TACTCCAGTCTTCATCC CGC (123) | | Sequencing | |
| IRF5_e02_a0 01_0-100 | CTGCAGTTGCCAGGTCA GT (124) | GAAAGTAAGGATCGGG CCTC (125) | | Sequencing | |
| IRF5_e03_a0 01_0-100 | CTCCTTCCCTTCCTCCAA AC (126) | aggcaggagaattgcttgaa (127) | | Sequencing | |
| IRF5_e04_a0 01_0-100 | ACACTGTTTCACCCTCCC AG (128) | GCCATTCCTGATATGCC AGT (129) | | Sequencing | |
| IRF5_e05_a0 01_0-100 | CTGGCATATCAGGAATGG CT (130) | AGACCTACCAAGCCCCA ACT (131) | | Sequencing | |
| IRF5_e06_a0 01_0-100 | TTCCTCCTGGGATTCTGAA CG (132) | GAATAGGGTGTCATGTG GGG (133) | | Sequencing | |

TABLE 10-continued

| | | | |
|---|---|---|---|
| IRF5_e07_a0 01_0-100 | TTGCCTCATAGTTCTCGC CT (134) | GTCCTTACGAGGCAGCA TGT (135) | Sequencing |
| IRF5_e08_a0 01_0_100 | TGGTGGTTGGGGGTCTA GTA (136) | ATCTCCAGGTCGGTCAC TGT (137) | Sequencing |
| IRF5_e10_a0 01_0-100 | GTAGGATTGGCAAGGAG GGT (138) | TTCCCCAAAGCAGAAGA AGA (139) | Sequencing |
| IRF5_e11_a0 01_0-100 | AGGACATCCCCAGTGAC AAG (140) | GGGGTGAGTAATAGACC GCA (141) | Sequencing |
| IRF5_e12_a0 01_0-26 | CTGAGCAGTGTGAACTTG GC (142) | GGGAGAGTTCTTTCCCT GCT (143) | Sequencing |
| IRF5_e12_a0 02_10-38 | TGGAGATGTTCTCAGGG GAG (144) | CAGAGGACAGGGAGAT GAGG (145) | Sequencing |
| IRF5_e12_a0 03_32-59 | TTTCCTGGAAGTGGATTT GG (146) | TTATGAAGGCCCAACTG ACC (147) | Sequencing |
| IRF5_e12_a0 04_48-77 | AGAGTGTTGTGGGCCAA GTC (148) | ACTCACTCACTGTCCCC ACC (149) | Sequencing |
| IRF5_e12_a0 05_65-94 | ACTACCAGTTGCTCCCAT GC (150) | TTGCGTTGCTGTAAACG AAG (151) | Sequencing |
| IRF5_e12_a0 06_78-100 | CTGAAGCAAGGGTGTGG AAT (152) | CAGGCCACTTAACCATG TGA (153) | Sequencing |
| IRF5_2kb_Up streamRegion _a001_0-18 | GCTCCAGATACGACCAG CAT (154) | GAACTTTGACCTTCCCT CCC (155) | Sequencing |
| IRF5_2kb_Up streamRegion _a002_18-40 | CATTCACATTTTCCCCAT CC (156) | GTCAACAGGCAGCAGG TGTA (157) | Sequencing |
| IRF5_2kb_Up streamRegion _a003_37-59 | TGGTGAAACCCCGTCTCT AC (158) | ATGGAATGTTCTTCGCT TGG (159) | Sequencing |
| IRF5_2kb_Up streamRegion _a004_48-69 | CATCAAAATTGAAACCCG CT (160) | TTCTCATCCTCAAACCC TGC (161) | Sequencing |
| IRF5_2kb_Up streamRegion _a005_63-84 | ccctggcaatccataacaAA (162) | TAGACTGGCCACTGGCT CTT (163) | Sequencing |
| IRF5_2kb_Up streamRegion _a006_74-96 | ATGGAATCGAAAACGGTT CA (164) | CAAGCTGAGCTCTGCCC A (165) | Sequencing |
| IRF5_2kb_Up streamRegion _a007_83-100 | CACATCTGGAAGGGGTG TCT (166) | CTAGACTTGGGGGCAGT AGC (167) | Sequencing |
| Exon1c_a001 _0-100 | CTGAGTTGTCCCGGTCTA GC (168) | GGAAACAGAAGCCACA GCTC (169) | Sequencing |
| IRF5_e01_a0 02_0-100 | AAGAGCCAGTGGCCAGT CTA (170) | CTCCTCTGTGGTCCAAG CC (171) | Sequencing |
| IRF5_e03_a0 02_0-100 | CTCCTTCCCTTCCTCCAA AC (172) | AGGCAGGAGAATTGCTT GAA (173) | Sequencing |
| IRF5_e11_a0 02_0-100 | AGGACATCCCCAGTGAC AAG (174) | GGGGTGAGTAATAGACC GCA (175) | Sequencing |
| IRF5_e12_a0 07_0-17 | AACCCGAGAGAAGAAG CTC (176) | AATCCACTTCCAGGAAA CCC (177) | Sequencing |
| IRF5_2kb_Up streamRegion _a008_57-82 | CTCCCCTCTCAACAGCTC AC (178) | TGTCATTTGACAACCCC GTA (179) | Sequencing |

TABLE 10-continued

| | | | | |
|---|---|---|---|---|
| IRF5_2kb_Upstream Region_a009_82-100 | GTGACTAGAGGATTCCC GCC (180) | TACTCCAGTCTTCATCC CGC (181) | | Sequencing |

| IRF5 primers used in Swedish samples | | | | |
|---|---|---|---|---|
| Assay Name | PCR Primer Forward (SEQ ID NO:) | PCR Primer Reverse (SEQ ID NO:) | Sequencing Primer Forward (SEQ ID NO:) | Sequencing Primer Reverse (SEQ ID NO:) | Platform |
| UUmolmed_IRF5_seq01 | TGTAAAACGACGGCCAGT CCGCTGAATTTTCCAAAA AG (182) | CAGGAAACAGCTATGACC CCTACCTTGACCGTCGA CCTG (183) | TGTAAAACGACGGCCAGT (184) | CAGGAAACAGCTATGACC (185) | |
| UUmolmed_IRF5_seq02 | TGTAAAACGACGGCCAGT GCAAGAGTTACCAAGCG AAGA (186) | CAGGAAACAGCTATGACC CCTCCAGGGAGATGCC AGAC (187) | TGTAAAACGACGGCCAGT (188) | CAGGAAACAGCTATGACC (189) | |
| UUmolmed_IRF5_seq03 | TGTAAAACGACGGCCAGT TGACAGTTTTGCCATTCC AG (190) | CAGGAAACAGCTATGACC CGAGGGAGAGCAGCAG AGC (191) | TGTAAAACGACGGCCAGT (192) | CAGGAAACAGCTATGACC (193) | |
| UUmolmed_IRF5_seq04 | TGTAAAACGACGGCCAGT CTTTTGGTGTCAGGCAGT CA (194) | CAGGAAACAGCTATGACC CTTATGTGCGCTCCTCT TCTG (195) | TGTAAAACGACGGCCAGT (196) | CAGGAAACAGCTATGACC (197) | |
| UUmolmed_IRF5_seq05 | TGTAAAACGACGGCCAGT TTATTCTGCATCCCCTGG AG (198) | CAGGAAACAGCTATGACC CTCGTTGGCTTCCTTTA GCAT (199) | TGTAAAACGACGGCCAGT (200) | CAGGAAACAGCTATGACC (201) | |
| UUmolmed_IRF5_seq06 | TGTAAAACGACGGCCAGT TTGTAAAGACAGGAGTCT CGTTATG (202) | CAGGAAACAGCTATGACC CTCGTAGATGAGGCGG AAGTC (203) | TGTAAAACGACGGCCAGT (204) | CAGGAAACAGCTATGACC (205) | |
| UUmolmed_IRF5_seq07 | TGTAAAACGACGGCCAGT GCCAAGGAGACAGGGAA ATA (206) | CAGGAAACAGCTATGACC CCTCCTCTCCTGCACCA AAAG (207) | TGTAAAACGACGGCCAGT (208) | CAGGAAACAGCTATGACC (209) | |
| UUmolmed_IRF5_seq08 | TGTAAAACGACGGCCAGT TCTCCTCCGACATTGACT CC (210) | CAGGAAACAGCTATGACC CAGGCTTGGCAACATCC TCT (211) | TGTAAAACGACGGCCAGT (212) | CAGGAAACAGCTATGACC (213) | |
| UUmolmed_IRF5_seq09 | TGTAAAACGACGGCCAGT CCCCAGGTCAGTGGAAT AAC (214) | CAGGAAACAGCTATGACC CAGGTCTGGCAGGAGC TGTT (215) | TGTAAAACGACGGCCAGT (216) | CAGGAAACAGCTATGACC (217) | |
| UUmolmed_IRF5_seq10 | TGTAAAACGACGGCCAGT GGCTTCAGGGAGCTTCT CTC (218) | CAGGAAACAGCTATGACC CCCTGTAGCTGGAGGAT GAGC (219) | TGTAAAACGACGGCCAGT (220) | CAGGAAACAGCTATGACC (221) | |
| UUmolmed_IRF5_seq11 | TGTAAAACGACGGCCAGT CCGACCTGGAGATCAAG TTT (222) | CAGGAAACAGCTATGACC CTTCCCCAAAGCAGAAG AAGA (223) | TGTAAAACGACGGCCAGT (224) | CAGGAAACAGCTATGACC (225) | |
| UUmolmed_IRF5_seq12 | TGTAAAACGACGGCCAGT TTGATGCAGAGCTCATCC TG (226) | CAGGAAACAGCTATGACC CGATGGAGCTCCTTGAA TTGC (227) | TGTAAAACGACGGCCAGT (228) | CAGGAAACAGCTATGACC (229) | |
| UUmolmed_IRF5_seq13 | TGTAAAACGACGGCCAGT CAGGGGAGCTATCTTGG TCA (230) | CAGGAAACAGCTATGACC CAAATGGGGCAATCACA AGAG (231) | TGTAAAACGACGGCCAGT (232) | CAGGAAACAGCTATGACC (233) | |
| UUmolmed_IRF5_seq14 | TGTAAAACGACGGCCAGT TGGGGCCTAGCTGTATA GGA (234) | CAGGAAACAGCTATGACC CATTCCACACCCTTGCT TCAG (235) | TGTAAAACGACGGCCAGT (236) | CAGGAAACAGCTATGACC (237) | |
| UUmolmed_IRF5_seq15 | TGTAAAACGACGGCCAGT GGTCAGTTGGGCCTTCAT AA (238) | CAGGAAACAGCTATGACC CGGGCAAGGTATCCTTG AACAT (239) | TGTAAAACGACGGCCAGT (240) | CAGGAAACAGCTATGACC (241) | |

TABLE 10-continued qPCR assay information

| Assay Name | Forward Primer (SEQ ID NO:) | Reverse Primer (SEQ ID NO:) | Extension Primer/Probe (SEQ ID NO:) |
|---|---|---|---|
| Short form | CCCTTCTTGAGAGTCCAA (242) | TTTTTTTTTTTTTTTTTC TGTT (243) | CCTGGAGCAGAAATAATTT (244) |
| Long form | CCCTTCTTGAGAGTCCAA (245) | TAGTAGTAAAAGGAAAG AAACAG (246) | CCTGGAGCAGAAATAATTT (247) |
| Common | CCTTCCCGGGCCTTTCT (248) | TTCCCTGCTCATGGCTG AAT (249) | TGTCTCTGGTCTGGTCAG (250) |
| GAPDH | Man Gene Expression Assay ID Hs 99999905_m1 (Applied Biosystems) | | |

TABLE 11

Single marker transmission and conditional analyses in SLE trios from US and UK

| Marker | Position[1] | Allele[2] | T[3] | U[3] | T/U[3] | X[2] | P[4] | P[5] conditional on Group 1 variants (rs2070197) | P conditional on Group 1 (rs2070197) and Group 2 (rs2004640) variants | P conditional on Group 1 (rs2070197), Group 2 (rs2004640), and Group 3 (rs10954213) variants |
|---|---|---|---|---|---|---|---|---|---|---|
| rs7780972 | 128, 113, 113 | C | 88 | 73 | 1.2 | 1.4 | 0.237 | 0.03 | 0.14 | 0.25 |
| rs9656375 | 128, 115, 191 | G | 213 | 210 | 1 | 0 | 0.884 | 0.87 | 0.65 | 0.58 |
| rs4731523 | 128, 124, 227 | A | 241 | 211 | 1.1 | 2 | 0.158 | 0.36 | 0.32 | 0.4 |
| rs6948542 | 128, 141, 463 | G | 184 | 166 | 1.1 | 0.9 | 0.336 | 0.29 | 0.27 | 0.37 |
| rs1495461 | 128, 145, 691 | G | 260 | 220 | 1.2 | 3.3 | 0.068 | 0.37 | 0.59 | 0.45 |
| rs960633 | 128, 154, 711 | T | 257 | 209 | 1.2 | 4.9 | 0.026 | 0.54 | 0.75 | 0.56 |
| rs6968225 | 128, 157, 557 | G | 106 | 105 | 1 | 0 | 0.945 | 0.48 | 0.08 | 0.19 0.82 |
| rs729302 | 128, 162, 910 | A | 270 | 195 | 1.4 | 12.1 | $5.0 \times 10^{-4}$ | 0.0024 | 0.56 | 0.82 |
| rs4728142 | 128, 167, 917 | A | 363 | 257 | 1.4 | 18.1 | $2.1 \times 10^{-5}$ | 0.0054 | 0.0096 | 0.2 |
| rs3807135 | 128, 171, 568 | C | 298 | 241 | 1.2 | 6 | 0.0141 | 0.28 | 0.0008 | 0.31 |
| rs2004640 | 128, 172, 251 | T | 344 | 233 | 1.5 | 21.4 | $3.8 \times 10^{-6}$ | 0.0019 | — | — |
| rs752637 | 128, 173, 371 | G | 297 | 238 | 1.2 | 6.5 | 0.011 | 0.28 | 0.001 | 0.14 |
| rs1874328 | 128, 179, 054 | T | 280 | 275 | 1 | 0 | 0.832 | 0.47 | 0.04 | 0.94 |
| Exon 6 indel | 128, 181, 324-54 | A | 337 | 294 | 1.1 | 2.9 | 0.087 | 0.25 | 0.01 | NA |
| rs2070197 | 128, 182, 950 | C | 205 | 111 | 1.8 | 28 | $1.2 \times 10^{-7}$ | — | — | — |
| rs10954213 | 128, 183, 377 | A | 282 | 226 | 1.2 | 6.2 | 0.013 | 0.14 | 0.0089 | — |
| rs11770589 | 128, 183, 438 | G | 338 | 288 | 1.2 | 4 | 0.046 | 0.16 | 0.01 | NA |
| rs10954214 | 128, 183, 583 | T | 281 | 232 | 1.2 | 4.7 | 0.031 | 0.14 | 0.02 | NA |
| rs10488630 | 128, 187, 899 | G | 280 | 263 | 1.1 | 0.5 | 0.466 | 0.42 | 0.11 | 0.9 |
| rs10488631 | 128, 188, 133 | C | 223 | 125 | 1.8 | 27.6 | $1.5 \times 10^{-7}$ | 1 | NA[6] | NA |
| rs2280714 | 128, 188, 675 | A | 268 | 219 | 1.2 | 4.9 | 0.026 | 0.18 | 0.0078 | NA |
| rs3847098 | 128, 189, 099 | G | 211 | 199 | 1.1 | 0.4 | 0.553 | 0.28 | 0.06 | 0.83 |
| rs11761242 | 128, 189, 556 | T | 25 | 20 | 1.3 | 0.6 | 0.456 | 0.03 | 0.06 | 0.06 |
| rs12539741 | 128, 190, 755 | T | 222 | 125 | 1.8 | 27.1 | $1.9 \times 10^{-7}$ | 1 | NA | NA |
| rs17166351 | 128, 191, 754 | C | 336 | 290 | 1.2 | 3.4 | 0.066 | 0.17 | 0.005 | NA |
| rs6966125 | 128, 192, 475 | C | 153 | 124 | 1.2 | 3 | 0.081 | 0.03 | 0.825 | 0.29 |

| | Single marker[7] | | | | Two marker | | | | |
|---|---|---|---|---|---|---|---|---|---|
| Marker | P conditional on rs2004640 | P conditional on exon6 indel | P conditional on rs2070197 | P conditional on rs10954213 | P conditional on rs2004640, exon6_indel | P conditional on rs2004640, rs2070197 | P conditional on rs2004640, rs10954213 | P conditional on exon6_indel, rs2070197 | P conditional on exon6_indel, rs10954213 |
| rs7780972 | 0.06 | 0.02 | 0.03 | 0.11 | 0.20 | 0.14 | 0.21 | 0.10 | 0.12 |
| rs9656375 | 0.46 | 0.52 | 0.87 | 0.35 | 0.56 | 0.65 | 0.27 | 0.78 | 0.75 |
| rs4731523 | 0.17 | 0.72 | 0.36 | 0.24 | 0.34 | 0.32 | 0.23 | 0.38 | 0.43 |
| rs6948542 | 0.56 | 0.08 | 0.29 | 0.47 | 0.13 | 0.27 | 0.92 | 0.40 | 0.41 |
| rs1495461 | 0.88 | 0.17 | 0.37 | 0.22 | 0.80 | 0.59 | 0.63 | 0.21 | 0.08 |
| rs960633 | 0.91 | 0.10 | 0.54 | 0.09 | 0.52 | 0.75 | 0.29 | 0.14 | 0.06 |
| rs6968225 | 0.13 | 0.13 | 0.48 | 0.31 | 0.10 | 0.08 | 0.19 | 0.17 | 0.31 |
| rs729302 | 0.97 | $4.5 \times 10^{-5}$ | 0.0024 | $1.1 \times 10^{-5}$ | 0.70 | 0.56 | 0.81 | 0.0046 | 0.0037 |
| rs4728142 | 0.02 | $7.7 \times 10^{-9}$ | 0.0054 | $2.3 \times 10^{-6}$ | 0.0081 | 0.0096 | 0.24 | $4.4 \times 10^{-5}$ | $4.7 \times 10^{-5}$ |
| rs3807135 | $2.3 \times 10^{-4}$ | $6.8 \times 10^{-6}$ | 0.28 | 0.01 | 0.56 | $8.3 \times 10-4$ | 0.31 | 0.16 | 0.13 |
| rs2004640 | — | $8.8 \times 10^{-10}$ | 0.0019 | $5.1 \times 10^{-9}$ | — | — | — | $1.4 \times 10^{-4}$ | $2.9 \times 10^{-5}$ |
| rs752637 | $4.8 \times 10^{-4}$ | $9.5 \times 10^{-6}$ | 0.28 | 0.02 | 0.23 | 0.0010 | 0.11 | 0.20 | 0.19 |
| rs1874328 | $1.3 \times 10^{-4}$ | 0.04 | 0.47 | 0.03 | 0.88 | 0.04 | 0.0016 | 0.04 | 0.02 |
| Exon 6 indel | $1.3 \times 10^{-4}$ | — | 0.25 | $1.3 \times 10^{-6}$ | — | 0.01 | $4.3 \times 10^{-3}$ | — | — |

TABLE 11-continued

Single marker transmission and conditional analyses in SLE trios from US and UK

| | | | | | | | | | |
|---|---|---|---|---|---|---|---|---|---|
| rs2070197 | $4.8 \times 10^{-4}$ | $8.0 \times 10^{-8}$ | — | $1.9 \times 10^{-6}$ | $9.2 \times 10^{-5}$ | — | $6.1 \times 10^{-5}$ | — | NA |
| rs10954213 | 0.0047 | $3.7 \times 10^{-7}$ | 0.14 | — | $1.1 \times 10^{-4}$ | 0.0089 | — | NA | — |
| rs11770589 | $5.5 \times 10^{-4}$ | NA | 0.16 | $2.2 \times 10^{-5}$ | NA | 0.01 | $3.2 \times 10^{-4}$ | NA | NA |
| rs10954214 | 0.0071 | $4.4 \times 10^{-6}$ | 0.14 | 0.56 | NA | 0.02 | NA | 0.74 | 0.73 |
| rs10488630 | $1.3 \times 10^{-4}$ | 0.14 | 0.42 | 0.0057 | 0.81 | 0.11 | $1.9 \times 10^{-4}$ | 0.14 | 0.10 |
| rs10488631 | $9.6 \times 10^{-5}$ | $1.4 \times 10^{-7}$ | 1.00 | $7.3 \times 10^{-6}$ | $1.5 \times 10^{-4}$ | NA | $1.9 \times 10^{-4}$ | NA | NA |
| rs2280714 | 0.0034 | $9.7 \times 10^{-6}$ | 0.18 | 0.54 | NA | 0.0078 | NA | 0.53 | 0.52 |
| rs3847098 | 0.0027 | 0.10 | 0.28 | 0.03 | 0.78 | 0.06 | 0.0032 | 0.10 | 0.07 |
| rs11761242 | 0.0097 | 0.06 | 0.03 | 0.02 | 0.04 | 0.06 | 0.01 | 0.08 | 0.09 |
| rs12539741 | $6.2 \times 10^{-5}$ | $9.9 \times 10^{-8}$ | 1.00 | $5.5 \times 10^{-6}$ | $9.6 \times 10^{-5}$ | NA | $1.4 \times 10^{-4}$ | NA | NA |
| rs17166351 | $3.3 \times 10^{-4}$ | NA | 0.17 | $1.1 \times 10^{-5}$ | NA | 0.005 | $3.3 \times 10^{-4}$ | NA | NA |
| rs6966125 | 0.78 | $3.2 \times 10^{-4}$ | 0.0078 | 0.20 | 0.45 | 0.82 | 0.30 | 0.36 | 0.23 |

| Marker | Two marker P conditional on rs2070197, rs10954213 | Three marker P conditional on rs2004640, exon6_indel, and rs2070197 | Three marker P conditional on rs2004640, exon6_indel, and rs10954213 | Three marker P conditional on rs2004640, rs2070197, and rs10954213 | Three marker P conditional on exon6_indel, rs2070197, and rs10954213 | Three marker P conditional on rs3807135, rs2004640, and rs2070197 | Four marker P conditional on rs2004640, exon6_indel, rs2070197, and rs10954213 | $r^2$ to rs2070197[8] |
|---|---|---|---|---|---|---|---|---|
| rs7780972 | 0.16 | 0.11 | 0.30 | 0.25 | 0.13 | 0.11 | 0.15 | 0.00 |
| rs9656375 | 0.50 | 0.66 | 0.70 | 0.58 | 0.72 | 0.83 | 0.64 | 0.00 |
| rs4731523 | 0.35 | 0.40 | 0.49 | 0.40 | 0.48 | 0.61 | 0.47 | 0.02 |
| rs6948542 | 0.51 | 0.18 | 0.11 | 0.37 | 0.47 | 0.29 | 0.15 | 0.00 |
| rs1495461 | 0.09 | 0.71 | 0.86 | 0.45 | 0.20 | 0.55 | 0.87 | 0.00 |
| rs960633 | 0.10 | 0.73 | 0.76 | 0.56 | 0.08 | 0.55 | 0.69 | 0.01 |
| rs6968225 | 0.18 | 0.14 | 0.16 | 0.19 | 0.26 | 0.06 | 0.19 | 0.02 |
| rs729302 | 0.0055 | 0.66 | 0.66 | 0.82 | 0.0023 | 0.73 | 0.79 | 0.08 |
| rs4728142 | $1.7 \times 10^{-5}$ | 0.17 | 0.16 | 0.20 | $9.3 \times 10^{-6}$ | 0.02 | 0.18 | 0.11 |
| rs3807135 | 0.16 | 0.32 | 0.35 | 0.31 | 0.12 | — | 0.29 | 0.09 |
| rs2004640 | $7.1 \times 10^{-5}$ | — | — | — | $1.5 \times 10^{-5}$ | — | — | 0.14 |
| rs752637 | 0.15 | 0.10 | 0.11 | 0.14 | 0.17 | NA | 0.09 | 0.09 |
| rs1874328 | 0.0049 | 0.88 | 0.88 | 0.94 | 0.02 | 0.27 | 0.95 | 0.13 |
| Exon 6 indel | NA | — | — | NA | — | 0.24 | — | 0.19 |
| rs2070197 | — | — | NA | — | — | — | — | — |
| rs10954213 | — | NA | — | — | — | 0.17 | — | 0.09 |
| rs11770589 | NA | NA | NA | NA | NA | 0.06 | 1.00 | 0.20 |
| rs10954214 | 0.73 | NA | NA | NA | 0.78 | 0.13 | 1.00 | 0.08 |
| rs10488630 | 0.05 | 0.75 | 0.65 | 0.90 | 0.08 | 0.48 | 0.76 | 0.11 |
| rs10488631 | NA | NA | NA | NA | NA | NA | 1.00 | 1.00 |
| rs2280714 | 0.68 | NA | NA | NA | 0.62 | 0.07 | 1.00 | 0.08 |
| rs3847098 | 0.07 | 0.82 | 0.72 | 0.83 | 0.05 | 0.52 | 0.82 | 0.12 |
| rs11761242 | 0.12 | 0.04 | 0.04 | 0.06 | 0.10 | 0.06 | 0.04 | 0.01 |
| rs12539741 | NA | NA | NA | NA | NA | NA | 1.00 | 0.99 |
| rs17166351 | NA | NA | NA | NA | NA | 0.09 | 1.00 | 0.20 |
| rs6966125 | 0.29 | 0.38 | 0.35 | 0.29 | 0.22 | 0.46 | 0.29 | 0.03 |

[1]Position in the HG17 assembly of the Human Genome
[2]The overtransmitted allele
[3]Number of transmitted alleles (T), untransmitted alleles (U), and transmitted to untransmitted allele ratio (T/U)
[4]Nominal P value for association to SLE
[5]P value for the association to SLE under the model that the indicated markers fully explain the association, as determined by conditional logistic regression
[6]NA indicates that the association to SLE cannot be calculated because it is statistically indistinguishable from the proposed model
[7]P value for the association to SLE under the model that the indicated single marker, or two-, three-, or four-marker haplotype fully explains the association to SLE, as determined by conditional logistic regression
[8]Correlation of marker to rs207019

TABLE 12

Variants discovered by resequencing all IRF5 exons and introns and 1 Kb upstream of exon 1A in 42 Swedish SLE cases

| Internal ID | Rs number[1] | Chromosome | Position[2] | MAF[3] | Minor Allele | Number of chromosomes[4] | Number of chromosomes with minor allele | Description |
|---|---|---|---|---|---|---|---|---|
| UUmolmed_IRF5_01 | rs3757386 | 7 | 128, 171, 248 | 0.17 | A | 42 | 7 | Promoter |
| UUmolmed_IRF5_02 | rs3757385 | 7 | 128, 171, 255 | 0.21 | A | 42 | 9 | Promoter |
| UUmolmed_IRF5_03 | rs3834330 | 7 | 128171273-5 | 0.16 | TG "deletion" | 44 | 7 | Promoter |

TABLE 12-continued

Variants discovered by resequencing all IRF5 exons and introns and 1 Kb upstream of exon 1A in 42 Swedish SLE cases

| Internal ID | Rs number[1] | Chromosome | Position[2] | MAF[3] | Minor Allele | Number of chromosomes[4] | Number of chromosomes with minor allele | Description |
|---|---|---|---|---|---|---|---|---|
| UUmolmed_IRF5_04 | rs3807134 | 7 | 128, 171, 289 | 0.15 | G | 46 | 7 | Promoter |
| UUmolmed_IRF5_05 | rs3807135 | 7 | 128, 171, 568 | 0.26 | A | 46 | 12 | Promoter |
| UUmolmed_IRF5_06 | rs6968563 | 7 | 128, 171, 682 | 0.04 | A | 46 | 2 | Promoter |
| UUmolmed_IRF5_07 | | 7 | 128, 172, 086 | 0.06 | G | 72 | 4 | Promoter |
| UUmolmed_IRF5_08 | gcccc clusters | 7 | 128171882-7 | 0.37 | GCCCC "insertion" | 86 | 32 | Promoter |
| UUmolmed_IRF5_09 | rs6953165 | 7 | 128, 172, 161 | 0.04 | G | 28 | 1 | Intron |
| UUmolmed_IRF5_10 | rs2004640 | 7 | 128, 172, 252 | 0.49 | G | 90 | 44 | Intron |
| UUmolmed_IRF5_11 | rs11767834 | 7 | 128, 175, 227 | 0.02 | A | 46 | 1 | Intron |
| UUmolmed_IRF5_12 | | 7 | 128, 175, 684 | 0.02 | A | 46 | 1 | Intron |
| UUmolmed_IRF5_13 | | 7 | 128, 175, 305 | 0.02 | C | 46 | 1 | Intron |
| UUmolmed_IRF5_14 | | 7 | 128, 175, 281 | 0.02 | G | 46 | 1 | Intron |
| UUmolmed_IRF5_15 | rs11761199 | 7 | 128, 175, 786 | 0.5 | G | 42 | 21 | Intron |
| UUmolmed_IRF5_16 | | 7 | 128, 175, 834 | 0.18 | A | 44 | 8 | Intron |
| UUmolmed_IRF5_17 | rs1874327 | 7 | 128, 179, 327 | 0.27 | A | 56 | 15 | Intron |
| UUmolmed_IRF5_18 | | 7 | 128, 179, 567 | 0.23 | C | 56 | 13 | Intron |
| UUmolmed_IRF5_19 | | 7 | 128, 179, 704 | 0.03 | A | 30 | 1 | Intron |
| UUmolmed_IRF5_20 | | 7 | 128, 180, 368 | 0.02 | A | 48 | 1 | Intron |
| UUmolmed_IRF5_21 | | 7 | 128, 180, 688 | 0.07 | A | 30 | 2 | Intron |
| UUmolmed_IRF5_22 | | 7 | 128181324-54 | 0.45 | 30nt deletion | 76 | 34 | In-frame deletion |
| UUmolmed_IRF5_23 | | 7 | 128182387-8 | 0.18 | G "insertion" | 84 | 15 | Intron |
| UUmolmed_IRF5_24 | rs2070197 | 7 | 128, 182, 951 | 0.32 | G | 44 | 14 | 3'UTR |
| UUmolmed_IRF5_25 | rs10954213 | 7 | 128, 183, 378 | 0.24 | T | 50 | 12 | 3'UTR |
| UUmolmed_IRF5_26 | rs11770589 | 7 | 128, 183, 439 | 0.42 | C | 52 | 22 | 3'UTR |
| UUmolmed_IRF5_27 | rs10954214 | 7 | 128, 183, 584 | 0.24 | T | 34 | 8 | 3'UTR |

[1]Number assigned to variant by dbSNP (World Wide Web at ncbi.nlm.nih.gov/entrez/query.fcgi?db=snp);
[2]Position in the HG17 assembly of the Human Genome;
[3]Minor Allele Frequency;
[4]Number of chromosomes with high quality data

TABLE 13

Variants discovered by resequencing all IRF5 exons and 1 Kb upstream of exon 1A in 96 US SLE cases

| Internal_ID | Rs Number[1] | Chromosome | Position[2] | MAF[3] | Minor Allele | Number of chromosomes[4] | Number of chromosomes with minor allele | Description | Frequency in HapMap CEU |
|---|---|---|---|---|---|---|---|---|---|
| Broad11429372 | rs3757388 | 7 | 128, 169, 974 | 0.27 | G | 166 | 44 | promoter | failed_design |
| Broad11429376 | rs4639458 | 7 | 128, 170, 037 | 0.42 | T | 166 | 69 | promoter | failed_QC |
| Broad11374596 | | 7 | 128, 170, 524 | 0.03 | A | 176 | 6 | promoter | |
| Broad11374705 | | 7 | 128, 170, 965 | 0.01 | A | 190 | 2 | promoter | |
| Broad11374729 | | 7 | 128, 171, 076 | 0.01 | A | 190 | 1 | promoter | |

TABLE 13-continued

Variants discovered by resequencing all IRF5 exons and 1 Kb upstream of exon 1A in 96 US SLE cases

| Internal_ID | Rs Number[1] | Chromosome | Position[2] | MAF[3] | Minor Allele | Number of chromosomes[4] | Number of chromosomes with minor allele | Description | Frequency in HapMap CEU |
|---|---|---|---|---|---|---|---|---|---|
| Broad11374811 | | 7 | 128, 171, 232 | 0.02 | A | 190 | 3 | promoter | |
| Broad11374827 | rs3757386 | 7 | 128, 171, 248 | 0.12/0.02 | T/G | 192 | 22/3 | promoter | failed_design |
| Broad11374834 | rs3757385 | 7 | 128, 171, 255 | 0.26 | T | 184 | 47 | promoter | failed_design |
| Broad11374851 | rs3840553 | 7 | 128, 171, 277 | 0.11 | A | 188 | 21 | promoter | failed QC |
| Broad11374863 | rs3807134 | 7 | 128, 171, 289 | 0.12 | C | 190 | 23 | promoter | failed_design |
| Broad11374900 | rs3807135 | 7 | 128, 171, 568 | 0.27 | T | 172 | 46 | promoter | 0.44 |
| Broad11374958 | rs6968563 | 7 | 128, 171, 682 | 0.03 | C | 164 | 5 | promoter | 0.05 |
| Broad11374970 | | 7 | 128, 171, 699 | 0.01 | C | 166 | 1 | promoter | |
| Broad11880969 | | 7 | 128, 174, 987 | 0.01 | T | 190 | 1 | intronic | |
| Broad11880979 | rs3807305 | 7 | 128, 175, 084 | 0.01 | A | 192 | 2 | intronic | |
| Broad11880984 | | 7 | 128, 175, 162 | 0.01 | G | 192 | 2 | intronic | |
| Broad11375359 | | 7 | 128, 179, 704 | 0.01 | A | 192 | 2 | intronic | |
| Broad11375713 | | 7 | 128, 180, 096 | 0.01 | A | 192 | 1 | intronic | |
| Broad11375787 | | 7 | 128, 180, 663 | 0.01 | T | 192 | 1 | intronic | |
| Broad11375788 | | 7 | 128, 180, 688 | 0.02 | A | 192 | 3 | intronic | 0.01 |
| Broad11376007 | | 7 | 128, 180, 986 | 0.01 | T | 192 | 1 | intronic | |
| Exon6_Deletion | | 7 | 128, 181, 324-54 | 0.48 | 30nt deletion | 190 | 92 | In-frame deletion | 0.48 |
| Broad11376731 | rs2230117 | 7 | 128, 181, 996 | 0.01 | G | 192 | 1 | synonymous | 0 |
| Broad11376908 | | 7 | 128, 182, 399 | 0.13 | G | 166 | 22 | intronic | |
| Broad11376919 | | 7 | 128, 182, 426 | 0.03 | A | 174 | 5 | intronic | 0.04 |
| Broad11376973 | | 7 | 128, 182, 546 | 0.02 | G | 176 | 4 | intronic | |
| Broad11376984 | | 7 | 128, 182, 561 | 0.02 | G | 192 | 3 | intronic | 0.02 |
| Broad11376997 | | 7 | 128, 182, 579 | 0.01 | G | 182 | 1 | missense | |
| Broad11377186 | rs2070197 | 7 | 128, 182, 951 | 0.18 | C | 190 | 35 | 3'UTR | 0.17 |
| Broad11377207 | | 7 | 128, 182, 978 | 0.01 | G | 192 | 1 | 3'UTR | |
| Broad11377253 | | 7 | 128, 183, 044 | 0.02 | C | 178 | 4 | 3'UTR | 0 |
| Broad11377330 | rs10954213 | 7 | 128, 183, 378 | 0.36 | G | 192 | 69 | 3'UTR | 0.46 |
| Broad11377356 | rs11770589 | 7 | 128, 183, 439 | 0.4 | G | 192 | 77 | 3'UTR | 0.38 |
| Broad11377358 | | 7 | 128, 183, 459 | 0.01 | A | 192 | 1 | 3'UTR | |
| Broad11429458 | rs10954214 | 7 | 128, 183, 584 | 0.22 | C | 192 | 43 | 3'UTR | 0.42 |
| Broad11429530 | | 7 | 128, 184, 089 | 0.01 | T | 192 | 1 | 3'UTR | |

[1]Number assigned to variant by dbSNP (World Wide Web at ncbi.nlm.nih.gov/entrez/query.fcgi?db=snp)
[2]Position in the HG17 assembly of the Human Genome
[3]Minor Allele Frequency
[4]Number of chromosomes with high quality data

TABLE 14

Association with IRF5 mRNA expression in transformed B-cells from HapMap CEU, CHB, JPT, and YRI populations

| Variant | Chromosome | Position[1] | P value[2] |
|---|---|---|---|
| rs7780972 | 7 | 128, 113, 113 | 0.66 |
| rs4731523 | 7 | 128, 124, 227 | 0.45 |
| rs6948542 | 7 | 128, 141, 463 | 0.9 |
| rs1495461 | 7 | 128, 145, 691 | 0.57 |
| rs960633 | 7 | 128, 154, 711 | 0.0036 |
| rs6968225 | 7 | 128, 157, 557 | $6.0 \times 10^{-25}$ |
| rs729302 | 7 | 128, 162, 910 | 0.0075 |
| rs4728142 | 7 | 128, 167, 917 | $6.5 \times 10^{-21}$ |
| rs2004640 | 7 | 128, 172, 251 | $4.2 \times 10^{-14}$ |
| rs1874328 | 7 | 128, 179, 054 | $1.3 \times 10^{-22}$ |
| Exon6 indel | 7 | 128, 181, 324 | $2.0 \times 10^{-31}$ |
| rs2070197 | 7 | 128, 182, 950 | $8.7 \times 10^{-7}$ |
| rs10954213 | 7 | 128, 183, 377 | $3.5 \times 10^{-55}$ |
| rs11770589 | 7 | 128, 183, 438 | $3.7 \times 10^{-33}$ |
| rs10954214 | 7 | 128, 183, 583 | $1.7 \times 10^{-40}$ |
| rs10488631 | 7 | 128, 188, 133 | $7.9 \times 10^{-7}$ |
| rs2280714 | 7 | 128, 188, 675 | $1.7 \times 10^{-40}$ |
| rs3847098 | 7 | 128, 189, 099 | $2.0 \times 10^{-11}$ |
| rs11761242 | 7 | 128, 189, 556 | 0.0011 |
| rs12539741 | 7 | 128, 190, 755 | $2.1 \times 10^{-6}$ |
| rs17166351 | 7 | 128, 191, 754 | $7.4 \times 10^{-34}$ |
| rs6966125 | 7 | 128, 192, 475 | $1.8 \times 10^{-24}$ |

[1]Position of variant in the HG17 assembly of the human genome
[2]Association of variant to IRF5 mRNA levels in 210 unrelated EBV transformed B-cells lines derived from the HapMap samples (GENEVAR dataset, World Wide Web at sanger-.ac.uk/humgen/genevar/)

TABLE 15

Association of genotype with IRF5 expression in 233 transformed B-cell lines

| Marker | Chromosome | Position[1] | Location | MAF[2] | Nominal P[3] | P conditional on rs10954213[4] | P conditional on RS2004640 and rs10954213[5] |
|---|---|---|---|---|---|---|---|
| rs729302 | 7 | 128, 162, 911 | Promoter | 0.32 | 0.02 | 0.34 | 0.201 |
| rs2004640 | 7 | 128, 172, 252 | Exon 1B splice site | 0.49 | $1.9 \times 10^{-17}$ | 0.0016 | — |
| rs752637 | 7 | 128, 173, 371 | intron | 0.45 | $1.2 \times 10^{-9}$ | 0.11 | 0.809 |
| rs2070197 | 7 | 128, 182, 951 | 3' UTR | 0.09 | 0.004 | 0.74 | 0.649 |
| rs10954213 | 7 | 128, 183, 378 | 3' UTR | 0.43 | $1.7 \times 10^{-38}$ | — | — |
| rs11770589 | 7 | 128, 183, 439 | 3' UTR | 0.48 | $2.4 \times 10^{-25}$ | 1 | 0.487 |
| rs10954214 | 7 | 128, 183, 584 | 3' UTR | 0.37 | $1.5 \times 10^{-34}$ | 0.0018 | NA 6 |
| rs2280714 | 7 | 128, 188, 676 | 5 kb 3' of IRF5 | 0.42 | $1.4 \times 10^{-35}$ | 0.0012 | NA 6 |

[1]Position of marker in the HG17 assembly of the human genome
[2]Minor Allele Frequency
[3]Uncorrected P value for association of the indicated marker to IRF5 mRNA levels in 233 CEPH EBV-transformed B cells
[4]Association of the indicated marker under the model that rs10954213 fully explains all the variance in IRF5 expression
[5]Association of the indicated marker under the model that rs10954213 and rs2004640 fully explain all the variance in IRF5 expression
[6]NA indicates that the association to IRF5 expression cannot be calculated because it is statistically indistinguishable from the proposed model

TABLE 16

Association of IRF5 region markers with IRF5 expression in the HapMap CEU population

| Chromosome | Marker | Position[1] | MAF[2] | P[3] | P conditional on rs10954213 and rs2004640[4] |
|---|---|---|---|---|---|
| 7 | rs13238831 | 128, 070, 432 | 0.19 | 0.34 | 1 |
| 7 | rs1532222 | 128, 070, 907 | 0.26 | 0.67 | 1 |
| 7 | rs7780972 | 128, 073, 124 | 0.1 | 0.65 | 1 |
| 7 | rs9656375 | 128, 075, 202 | 0.28 | 0.37 | 1 |
| 7 | rs10954211 | 128, 075, 393 | 0.26 | 0.47 | 0.1 |
| 7 | rs4731523 | 128, 084, 238 | 0.19 | 1 | 0.41 |
| 7 | rs7782976 | 128, 086, 942 | 0.27 | 0.23 | 1 |
| 7 | rs6972002 | 128, 093, 690 | 0.24 | 0.56 | 1 |
| 7 | rs6948542 | 128, 101, 474 | 0.26 | 0.83 | 0.84 |
| 7 | rs7786945 | 128, 102, 425 | 0.26 | 0.46 | 1 |
| 7 | rs6467218 | 128, 102, 916 | 0.28 | 0.99 | 1 |
| 7 | rs7792282 | 128, 103, 530 | 0.27 | 0.77 | 1 |
| 7 | rs1495461 | 128, 105, 702 | 0.22 | 0.46 | 0.92 |
| 7 | rs960633 | 128, 114, 723 | 0.28 | 0.58 | 1 |
| 7 | rs6968225 | 128, 117, 569 | 0.18 | 0.0036 | 1 |
| 7 | rs729302 | 128, 122, 922 | 0.32 | 0.23 | 1 |
| 7 | rs4728142 | 128, 127, 929 | 0.41 | 7.47E−06 | 0.84 |
| 7 | rs2004640 | 128, 132, 263 | 0.49 | 8.72E−09 | — |
| 7 | rs752637 | 128, 133, 382 | 0.45 | 6.60E−10 | 1 |
| 7 | rs6975315 | 128, 136, 447 | 0.02 | 0.71 | 0.43 |
| 7 | rs7808907 | 128, 138, 046 | 0.47 | 1 | 0.86 |
| 7 | rs2070197 | 128, 142, 962 | 0.09 | 0.11 | 0.2 |
| 7 | rs10954213 | 128, 143, 389 | 0.43 | 2.83E−09 | — |
| 7 | rs11770589 | 128, 143, 450 | 0.48 | 1.04E−06 | 1 |
| 7 | rs10954214 | 128, 143, 595 | 0.37 | 1.19E−10 | NA |
| 7 | rs13242262 | 128, 145, 326 | 0.5 | 6.82E−09 | NA |
| 7 | rs10488630 | 128, 147, 910 | 0.28 | 0.001 | 0.63 |
| 7 | rs10488631 | 128, 148, 145 | 0.16 | 0.14 | 1 |
| 7 | rs2280714 | 128, 148, 687 | 0.42 | 2.75E−11 | NA |
| 7 | rs10229001 | 128, 153, 359 | 0.45 | 6.77E−09 | NA |
| 7 | rs1495458 | 128, 156, 954 | 0.03 | 0.19 | 0.55 |
| 7 | rs2172876 | 128, 157, 254 | 0.38 | 9.30E−07 | 0.12 |
| 7 | rs6957529 | 128, 159, 422 | 0.08 | 0.06 | 1 |
| 7 | rs7385716 | 128, 159, 556 | 0.47 | 1.30E−08 | NA |
| 7 | rs4731535 | 128, 159, 929 | 0.38 | 3.95E−07 | 0.12 |
| 7 | rs8043 | 128, 161, 346 | 0.38 | 3.95E−07 | 0.12 |
| 7 | rs1258897 | 128, 162, 375 | 0.01 | NA | NA |
| 7 | rs1874332 | 128, 168, 575 | 0.38 | 1 | 0.12 |
| 7 | rs2293492 | 128, 169, 028 | 0.08 | 0.06 | 0.75 |
| 7 | rs12531711 | 128, 171, 428 | 0.17 | 0.16 | 0.06 |
| 7 | rs17338998 | 128, 172, 521 | 0.16 | 0.27 | 0.03 |
| 7 | rs2272347 | 128, 173, 377 | 0.47 | 3.69E−09 | NA |
| 7 | rs3817555 | 128, 173, 483 | 0.04 | 0.46 | NA |
| 7 | rs7789423 | 128, 175, 166 | 0.42 | 2.75E−11 | NA |
| 7 | rs6948928 | 128, 177, 059 | 0.42 | 2.75E−11 | NA |
| 7 | rs12534421 | 128, 178, 035 | 0.17 | 0.16 | 0.06 |
| 7 | rs12535158 | 128, 178, 981 | 0.17 | 0.16 | 0.06 |
| 7 | rs12669885 | 128, 179, 251 | 0.04 | 0.46 | NA |
| 7 | rs1154330 | 128, 179, 750 | 0.2 | 0.00619 | 0.36 |
| 7 | rs17339221 | 128, 179, 876 | 0.2 | 0.01 | 0.36 |
| 7 | rs2290231 | 128, 180, 519 | 0.04 | 0.46 | NA |
| 7 | rs11770317 | 128, 183, 433 | 0.38 | 9.10E−07 | 0.12 |
| 7 | rs6969930 | 128, 184, 275 | 0.46 | 3.69E−09 | NA |
| 7 | rs2305323 | 128, 187, 680 | 0.28 | 0.000998 | 1 |
| 7 | rs3958094 | 128, 189, 225 | 0.28 | 0.000998 | 0.63 |
| 7 | rs7807018 | 128, 194, 146 | 0.45 | 9.99E−09 | NA |
| 7 | rs2305324 | 128, 195, 184 | 0.36 | 3.69E−06 | 0.15 |
| 7 | rs11768572 | 128, 199, 250 | 0.27 | 0.00281 | 1 |
| 7 | rs2305325 | 128, 208, 798 | 0.36 | 3.69E−06 | 0.15 |
| 7 | rs6965542 | 128, 209, 876 | 0.48 | 1.73E−08 | NA |
| 7 | rs3857852 | 128, 211, 235 | 0.42 | 6.28E−11 | NA |
| 7 | rs12539476 | 128, 211, 441 | 0.17 | 0.16 | 0.06 |
| 7 | rs17424179 | 128, 211, 953 | 0.03 | 0.57 | 0.53 |
| 7 | rs12155080 | 128, 212, 697 | 0.46 | 3.69E−09 | NA |
| 7 | rs13236009 | 128, 217, 131 | 0.17 | 0.19 | 0.05 |
| 7 | rs13221560 | 128, 217, 133 | 0.39 | 2.07E−10 | NA |
| 7 | rs10239340 | 128, 222, 468 | 0.46 | 3.69E−09 | NA |
| 7 | rs11762968 | 128, 224, 922 | 0.38 | 3.95E−07 | 0.12 |
| 7 | rs9649520 | 128, 226, 603 | 0.34 | 9.03E−06 | 0.16 |
| 7 | rs921403 | 128, 230, 682 | 0.43 | 8.49E−11 | 0.94 |
| 7 | rs4731541 | 128, 232, 194 | 0.45 | 8.15E−08 | 0.94 |
| 7 | rs1839600 | 128, 236, 681 | 0.02 | 0.34 | 0.03 |
| 7 | rs3807301 | 128, 236, 970 | 0.28 | 0.00416 | 0.84 |
| 7 | rs10279821 | 128, 237, 505 | 0.41 | 2.46E−10 | 0.91 |
| 7 | rs10156169 | 128, 238, 529 | 0.42 | 1.80E−10 | 0.66 |
| 7 | rs11767238 | 128, 240, 296 | 0.29 | 0 | 0.84 |
| 7 | rs17424602 | 128, 241, 898 | 0.15 | 0.33 | 0.02 |
| 7 | rs2167273 | 128, 243, 371 | 0.36 | 3.69E−06 | 0.15 |
| 7 | rs6960994 | 128, 246, 615 | 0.26 | 1 | 0.33 |
| 7 | rs6961014 | 128, 246, 668 | 0.25 | 0.00026 | 0.26 |
| 7 | rs6980198 | 128, 247, 954 | 0.02 | 0.71 | 0.44 |
| 7 | rs3807300 | 128, 248, 049 | 0.02 | 0.32 | 0.97 |
| 7 | rs2242028 | 128, 248, 934 | 0.25 | 0.00069 | 0.35 |
| 7 | rs13239597 | 128, 249, 941 | 0.17 | 0.16 | 0.06 |
| 7 | rs13246321 | 128, 255, 289 | 0.17 | 0.19 | 0.06 |
| 7 | rs17424921 | 128, 262, 080 | 0.17 | 0.05 | 0.34 |
| 7 | rs17340351 | 128, 262, 755 | 0.18 | 0.13 | 0.02 |
| 7 | rs17167079 | 128, 263, 129 | 0.02 | 0.11 | 0.97 |

TABLE 16-continued

Association of IRF5 region markers with IRF5 expression in the HapMap CEU population

| Chromosome | Marker | Position[1] | MAF[2] | P[3] | P conditional on rs10954213 and rs2004640[4] |
|---|---|---|---|---|---|
| 7 | rs1901198 | 128, 263, 747 | 0.38 | 1.91E−06 | 0.04 |
| 7 | rs7794772 | 128, 264, 168 | 0.02 | 0.32 | 0.97 |
| 7 | rs7795214 | 128, 264, 418 | 0.03 | 0.32 | 0.97 |
| 7 | rs13222967 | 128, 265, 186 | 0.27 | 0.18 | 0.49 |
| 7 | rs7783840 | 128, 265, 657 | 0.26 | 0.12 | 0.21 |
| 7 | rs12537496 | 128, 266, 826 | 0.23 | 0.01 | 1 |
| 7 | rs12536719 | 128, 271, 698 | 0.15 | 0.19 | 0.53 |
| 7 | rs12537284 | 128, 271, 864 | 0.16 | 0.12 | 0.04 |
| 7 | rs12537264 | 128, 271, 923 | 0.18 | 1 | 1 |
| 7 | rs17340542 | 128, 274, 003 | 0.17 | 0.16 | 1 |
| 7 | rs17425212 | 128, 275, 682 | 0.18 | 0.16 | 0.21 |
| 7 | rs17340646 | 128, 276, 472 | 0.26 | 1 | 0.03 |
| 7 | rs13227095 | 128, 277, 901 | 0.25 | 0.00176 | 0.1 |
| 7 | rs12706862 | 128, 279, 283 | 0.39 | 0.00163 | 1 |
| 7 | rs6959557 | 128, 279, 508 | 0.37 | 0.00595 | 1 |
| 7 | rs6959965 | 128, 279, 680 | 0.37 | 0.01 | 1 |
| 7 | rs7458937 | 128, 282, 712 | 0.32 | 0.00114 | 1 |
| 7 | rs2084654 | 128, 283, 086 | 0.38 | 0.00595 | 0.13 |
| 7 | rs4731545 | 128, 286, 220 | 0.41 | 0.39 | 0.09 |

TABLE 17

Association of IRF5 haplotypes with SLE

| | Haplotype | Group 2 Exon 1B[1] (rs2004640) | Exon 6 Indel[2] | Group 1 rs2070197 | Group 3 polyA+ signal[3] (rs10954213) | T[4] | U[5] | OR (95% c.i.)[6] | X[2] | P[7] |
|---|---|---|---|---|---|---|---|---|---|---|
| USA and UK | 1 | T | Insertion | C | A | 181 | 99 | 1.90 (1.50-2.41) | 24.2 | 8.5 × 10−7 |
| 555 trio pedigrees | 2 | T | Deletion | T | A | 248 | 222 | 1.12 (0.93-1.34) | 1.5 | 0.2269 |
| | 3 | T | Insertion | T | G | 43 | 50 | 0.86 (0.57-1.29) | 0.6 | 0.4384 |
| | 4 | G | Insertion | T | G | 195 | 234 | 0.83 (0.69-1.01) | 3.7 | 0.0553 |
| | 5 | G | Deletion | T | A | 104 | 165 | 0.63 (0.50-0.80) | 13.9 | 2.0 × 10−4 |

| | Haplotype | rs2004640 | Exon 6 Indel | rs2070197 | rs10954213 | Case Freq[8] | Control Freq[9] | OR (95% c.i.) | X[2] | P |
|---|---|---|---|---|---|---|---|---|---|---|
| USA and UK | 1 | T | Insertion | C | A | 0.175 | 0.114 | 1.66 (1.40-1.98) | 32.8 | 1.0 × 10−8 |
| Cases = 1532 | 2 | T | Deletion | T | A | 0.377 | 0.363 | 1.06 (0.94-1.21) | 0.9 | 0.3406 |
| Controls = 2878 | 3 | T | Insertion | T | G | 0.038 | 0.038 | 1.00 (0.72-1.38) | 0 | 0.9981 |
| | 4 | G | Insertion | T | G | 0.29 | 0.351 | 0.76 (0.66-0.87) | 16.4 | 5.3 × 10−5 |
| | 5 | G | Deletion | T | A | 0.119 | 0.135 | 0.86 (.71-1.04) | 2.4 | 0.1233 |

| | Haplotype | rs2004640 | Exon 6 Indel | rs2070197 | rs10954213 | Case Freq | Control Freq | OR (95% c.i.) | X[2] | P |
|---|---|---|---|---|---|---|---|---|---|---|
| Sweden | 1 | T | Insertion | C | A | 0.226 | 0.131 | 1.94 (1.47-2.57) | 21.4 | 3.6 × 10−6 |
| Cases = 656 | 2 | T | Deletion | T | A | 0.372 | 0.349 | 1.10 (0.89-1.38) | 0.8 | 0.3763 |
| Controls = 718 | 3 | T | Insertion | T | G | 0.046 | 0.047 | 0.97 (0.59-1.61) | 0 | 0.9176 |
| | 4 | G | Insertion | T | G | 0.219 | 0.296 | 0.67 (0.52-0.85) | 10.4 | 0.0012 |
| | 5 | G | Deletion | T | A | 0.137 | 0.177 | 0.73 (0.55-0.99) | 4.3 | 0.0393 |

| | Haplotype | rs2004640 | Exon 6 Indel | rs2070197 | rs10954213 | OR (95% c.i.) | Pooled P |
|---|---|---|---|---|---|---|---|
| Meta-analysis | 1 | T | Insertion | C | A | 1.78 (1.57-2.02) | 1.4 × 10−19 |
| 555 trio pedigrees | 2 | T | Deletion | T | A | 1.09 (0.99-1.19) | 0.0437 |
| Cases = 2188 | 3 | T | Insertion | T | G | 0.95 (0.76-1.19) | 0.6743 |
| Controls = 3596 | 4 | G | Insertion | T | G | 0.76 (0.69-0.84) | 5.0 × 10−8 |
| | 5 | G | Deletion | T | A | 0.76 (0.67-0.87) | 2.8 × 10−5 |

[1]Exon 1B Splice donor site (T allele allows expression of exon 1B transcripts)
[2]In-frame insertion/deletion of 30 bp in exon 6 of IRF5, chr7: 128,181,324-54 (HG17)
[3]polyA+ Signal variant ("A" allele is associated with 561 bp 3' UTR; "G" allele is associated with enrichment of 1214 bp 3' UTR
[4]Number of transmitted haplotypes
[5]Number of untransmitted haplotypes
[6]Odds Ratio and 95% confidence intervals
[7]Nominal P value for association to SLE
[8]Frequency of haplotypes in SLE cases
[9]Frequency of haplotypes in controls

TABLE 18

IRF5 genotype frequencies in SLE cases and controls

| Genotype[1] | Cases N[2] | Cases Frequency[3] | Controls N | Controls Frequency | OR[4] | I[2] | P |
|---|---|---|---|---|---|---|---|
| US and UK cases and controls ||||||||
| 1 1 | 26 | 0.028 | 14 | 0.01 | 2.96 | 11.5 | 0.00068 |
| 1 2 | 108 | 0.117 | 115 | 0.08 | 1.53 | 9.2 | 0.00249 |
| 1 3 | 17 | 0.018 | 9 | 0.006 | 2.99 | 7.7 | 0.00561 |
| 1 4 | 89 | 0.097 | 124 | 0.086 | 1.13 | 0.8 | 0.38648 |
| 1 5 | 41 | 0.045 | 51 | 0.035 | 1.27 | 1.2 | 0.26741 |
| 2 2 | 132 | 0.143 | 187 | 0.13 | 1.12 | 0.9 | 0.35655 |
| 2 3 | 32 | 0.035 | 52 | 0.036 | 0.96 | 0 | 0.85803 |
| 2 4 | 207 | 0.225 | 359 | 0.249 | 0.87 | 1.9 | 0.17033 |
| 2 5 | 83 | 0.09 | 144 | 0.1 | 0.89 | 0.6 | 0.42371 |
| 3 3 | 2 | 0.002 | 1 | 0.001 | 3.13 | 1 | 0.32719 |
| 3 4 | 20 | 0.022 | 46 | 0.032 | 0.67 | 2.2 | 0.14073 |
| 3 5 | 0 | 0 | 0 | 0 | | | |
| 4 4 | 87 | 0.094 | 162 | 0.113 | 0.82 | 2 | 0.16259 |
| 4 5 | 65 | 0.071 | 156 | 0.108 | 0.62 | 9.5 | 0.00209 |
| 5 5 | 12 | 0.013 | 19 | 0.013 | 0.99 | 0 | 0.97477 |
| Total | 921 | | 1439 | | | | |
| 1 X | 281 | 0.305 | 313 | 0.218 | 1.58 | 22.9 | 1.7 × 10⁻⁶ |
| 2 X | 562 | 0.61 | 857 | 0.596 | 1.06 | 0.5 | 0.47862 |
| 3 X | 71 | 0.077 | 108 | 0.075 | 1.03 | 0 | 0.85585 |
| 4 X | 468 | 0.508 | 847 | 0.589 | 0.72 | 14.7 | 0.00012 |
| 5 X | 201 | 0.218 | 370 | 0.257 | 0.81 | 4.6 | 0.03142 |
| Swedish cases and controls ||||||||
| 1 1 | 21 | 0.065 | 10 | 0.028 | 2.36 | 5.1 | 0.024 |
| 1 2 | 45 | 0.139 | 24 | 0.068 | 2.2 | 9.1 | 0.0025 |
| 1 3 | 7 | 0.022 | 3 | 0.009 | 2.56 | 2 | 0.161 |
| 1 4 | 37 | 0.114 | 31 | 0.088 | 1.33 | 1.2 | 0.264 |
| 1 5 | 20 | 0.062 | 14 | 0.04 | 1.58 | 1.7 | 0.195 |
| 2 2 | 47 | 0.145 | 44 | 0.125 | 1.18 | 0.6 | 0.454 |
| 2 3 | 12 | 0.037 | 9 | 0.026 | 1.46 | 0.7 | 0.394 |
| 2 4 | 53 | 0.164 | 82 | 0.234 | 0.64 | 5.2 | 0.023 |
| 2 5 | 36 | 0.111 | 41 | 0.117 | 0.95 | 0.1 | 0.816 |
| 3 3 | 0 | 0 | 0 | 0 | | | |
| 3 4 | 6 | 0.019 | 14 | 0.04 | 0.45 | 2.7 | 0.102 |
| 3 5 | 1 | 0.003 | 9 | 0.026 | 0.12 | 5.9 | 0.015 |
| 4 4 | 17 | 0.052 | 23 | 0.066 | 0.79 | 0.5 | 0.473 |
| 4 5 | 15 | 0.046 | 32 | 0.091 | 0.48 | 5.2 | 0.022 |
| 5 5 | 7 | 0.022 | 15 | 0.043 | 0.49 | 2.4 | 0.122 |
| Total | 324 | | 351 | | | | |
| 1 X | 130 | 0.401 | 82 | 0.234 | 2.2 | 22 | 2.8 × 10⁻⁶ |
| 2 X | 193 | 0.596 | 200 | 0.57 | 1.11 | 0.5 | 0.496 |
| 3 X | 26 | 0.08 | 35 | 0.1 | 0.79 | 0.8 | 0.378 |
| 4 X | 128 | 0.395 | 182 | 0.519 | 0.61 | 10.3 | 0.0013 |
| 5 X | 79 | 0.244 | 111 | 0.316 | 0.7 | 4.4 | 0.037 |

[1]Genotype of the IRF5 haplotypes defined in Table 17
[2]Number of individuals with the indicated genotype
[3]Genotype frequency
[4]Odds Ratio

TABLE 19

Frequency of IRF5 haplotypes in representative world populations from the Human Genome Diversity Project

| | | N[1] | Haplotype[2] 1 | 2 | 3 | 4 | 5 |
|---|---|---|---|---|---|---|---|
| Africa | Biaka Pygmies | 72 | — | 0.4 | — | 0.44 | 0.15 |
| | Mbuti Pygmies | 30 | — | 0.7 | — | 0.23 | 0.07 |
| | Mandenka | 48 | — | 0.38 | — | 0.54 | 0.08 |
| | Yoruba | 50 | — | 0.28 | — | 0.52 | 0.2 |
| | Bantu | 38 | — | 0.39 | 0.03 | 0.45 | 0.13 |
| | San | 14 | — | 0.21 | 0.29 | 0.14 | 0.36 |
| America | Colombian | 22 | 0.09 | — | — | 0.77 | 0.14 |
| | Karitiana | 48 | 0.02 | — | — | 0.9 | 0.08 |
| | Maya | 50 | 0.34 | 0.1 | — | 0.44 | 0.12 |
| | Pima | 50 | 0.36 | 0.02 | — | 0.5 | 0.12 |
| | Surui | 42 | — | — | — | 1 | — |
| Central/South Asia | Balochi | 50 | 0.04 | 0.38 | 0.06 | 0.32 | 0.2 |
| | Brahui | 50 | 0.3 | 0.16 | 0.08 | 0.16 | 0.3 |
| | Burusho | 50 | 0.18 | 0.32 | 0.14 | 0.3 | 0.06 |
| | Hazara | 50 | 0.02 | 0.38 | 0.06 | 0.3 | 0.24 |
| | Kalash | 50 | 0.04 | 0.32 | 0.04 | 0.56 | 0.04 |
| | Makrani | 50 | 0.14 | 0.36 | 0.04 | 0.24 | 0.22 |
| | Pathan | 49 | 0.14 | 0.25 | 0.12 | 0.27 | 0.2 |
| | Sindhi | 49 | 0.2 | 0.37 | 0.06 | 0.31 | 0.04 |
| | Uygur | 20 | 0.1 | 0.35 | — | 0.35 | 0.2 |
| East Asia | Cambodian | 20 | — | 0.3 | 0.25 | 0.3 | 0.15 |
| | Dai | 18 | — | — | 0.11 | 0.56 | 0.33 |
| | Daur | 20 | — | 0.25 | — | 0.6 | 0.15 |
| | Han | 90 | — | 0.18 | 0.06 | 0.33 | 0.43 |
| | Hezhen | 20 | — | 0.25 | 0.05 | 0.5 | 0.2 |
| | Japanese | 60 | 0.02 | 0.23 | 0.07 | 0.47 | 0.22 |
| | Lahu | 20 | — | 0.1 | 0.15 | 0.35 | 0.4 |
| | Miaozu | 20 | — | 0.1 | 0.15 | 0.35 | 0.4 |
| | Mongola | 18 | — | 0.17 | 0.06 | 0.33 | 0.44 |
| | Naxi | 20 | — | 0.3 | — | 0.35 | 0.35 |
| | Oroqen | 20 | 0.05 | 0.35 | 0.05 | 0.5 | 0.05 |
| | She | 20 | — | 0.25 | 0.05 | 0.25 | 0.45 |
| | Tu | 20 | 0.05 | 0.45 | 0.1 | 0.2 | 0.2 |
| | Tujia | 18 | — | 0.17 | 0.17 | 0.33 | 0.33 |
| | Xibo | 18 | — | 0.22 | 0.17 | 0.39 | 0.22 |
| | Yakut | 50 | — | 0.26 | 0.06 | 0.56 | 0.12 |
| | Yizu | 20 | — | 0.35 | 0.1 | 0.3 | 0.25 |
| Europe | Adygei | 30 | 0.23 | 0.33 | 0.03 | 0.27 | 0.13 |
| | French | 40 | 0.08 | 0.25 | 0.13 | 0.45 | 0.1 |
| | French Basque | 42 | 0.24 | 0.26 | 0.05 | 0.17 | 0.29 |
| | North Italian | 26 | 0.08 | 0.42 | 0.04 | 0.31 | 0.15 |
| | Orcadian | 30 | 0.13 | 0.43 | — | 0.3 | 0.13 |
| | Russian | 50 | 0.12 | 0.3 | 0.06 | 0.36 | 0.16 |
| | Sardinian | 52 | 0.04 | 0.38 | 0.08 | 0.31 | 0.19 |
| | Tuscan | 14 | — | 0.57 | 0.07 | 0.14 | 0.21 |
| Middle East | Bedouin | 98 | 0.1 | 0.4 | 0.1 | 0.34 | 0.06 |
| | Druze | 94 | 0.17 | 0.38 | 0.15 | 0.26 | 0.04 |
| | Mozabite | 58 | 0.02 | 0.4 | 0.03 | 0.36 | 0.19 |
| | Palestinian | 100 | 0.2 | 0.39 | 0.13 | 0.22 | 0.06 |
| Oceania | Melanesian | 40 | — | 0.1 | — | 0.75 | 0.15 |
| | Papuan | 34 | — | 0.03 | 0.12 | 0.5 | 0.35 |

[1]Number of chromosomes. Haplotypes with frequency >0.01 were analyzed.
[2]Phased haplotypes of IRF5 at rs2004640, rs2070197, and rs10954213.1 = TCA, 2 = TTA, 3 = TTG, 4 = GTG, 5 = GTA.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for assessing the predisposition of a human to develop systemic lupus erythematosus (SLE), comprising:
   (a) assaying nucleic acid from a biological sample of said human to determine whether or not said human has an IRF-5 haplotype comprising an rs2004640 T allele, the 30 base pair IRF-5 exon 6 insertion allele depicted in FIG. 11 herein, and an rs10954213 A allele; and
   (b) classifying said human as being predisposed to develop SLE if said human has said IRF-5 haplotype, or classifying said human as not being predisposed to develop SLE if said human does not contain said IRF-5 haplotype.

2. The method of claim 1, further comprising determining whether a biological sample from said human contains elevated levels of interferon-α (IFN-α), interleukin-1 receptor antagonist (IL-1RA), interleukin-6 (IL-6), monocyte chemoattractant protein-1 (MCP-1), macrophage inflammatory protein-1α (MIP-1α), macrophage inflammatory protein-1β (MIP-1β), or tumor necrosis factor-α (TNF-α).

3. A method for assessing the predisposition of a human to develop SLE, comprising:
   (a) assaying nucleic acid from a biological sample of said human to determine whether or not said human has an IRF-5 haplotype comprising an rs2004640 T allele, the 30 base pair IRF-5 exon 6 insertion allele depicted in FIG. 11 herein, an rs10954213 A allele, and an rs2070197 C allele; and
   (b) classifying said human as being predisposed to develop SLE if said human has said IRF-5 haplotype, or classifying said human as not being predisposed to develop SLE if said human does not have said IRF-5 haplotype.

4. The method of claim 3, further comprising determining whether a biological sample from said human contains elevated levels of interferon-α (IFN-α), interleukin-1 receptor antagonist (IL-1RA), interleukin-6 (IL-6), monocyte chemoattractant protein-1 (MCP-1), macrophage inflammatory protein-1α (MIP-1α), macrophage inflammatory protein-1β (MIP-1β), or tumor necrosis factor-α (TNF-α).

* * * * *

SEQUENCE LISTING

<160> NUMBER OF SEQ ID NOS: 258

<210> SEQ ID NO 1
<211> LENGTH: 30
<212> TYPE: DNA
<213> ORGANISM: Artificial Sequence
<220> FEATURE:
<223> OTHER INFORMATION: Primer

<400> SEQUENCE: 1
agcggataac aaatagacca gagaccaggg                                        30

<210> SEQ ID NO 2
<211> LENGTH: 30
<212> TYPE: DNA
<213> ORGANISM: Artificial Sequence
<220> FEATURE:
<223> OTHER INFORMATION: Primer

<400> SEQUENCE: 2
agcggataac aagtctaagt gagtggcagg                                        30

<210> SEQ ID NO 3
<211> LENGTH: 18
<212> TYPE: DNA
<213> ORGANISM: Artificial Sequence
<220> FEATURE:
<223> OTHER INFORMATION: Primer

<400> SEQUENCE: 3
atgggacaag gtgaagac                                                     18

<210> SEQ ID NO 4
<211> LENGTH: 30
<212> TYPE: DNA
<213> ORGANISM: Artificial Sequence
<220> FEATURE:
<223> OTHER INFORMATION: Primer

<400> SEQUENCE: 4
agcggataac aggcgctttg gaagtcccag                                        30

<210> SEQ ID NO 5
<211> LENGTH: 30
<212> TYPE: DNA
<213> ORGANISM: Artificial Sequence
<220> FEATURE:
<223> OTHER INFORMATION: Primer

<400> SEQUENCE: 5
agcggataac atgaagactg gagtagggcg                                        30

<210> SEQ ID NO 6
<211> LENGTH: 17
<212> TYPE: DNA
<213> ORGANISM: Artificial Sequence
<220> FEATURE:
<223> OTHER INFORMATION: Primer

<400> SEQUENCE: 6
ccctgctgta ggcaccc                                                      17

<210> SEQ ID NO 7
<211> LENGTH: 30
<212> TYPE: DNA

-continued

```
<213> ORGANISM: Artificial Sequence
<220> FEATURE:
<223> OTHER INFORMATION: Primer

<400> SEQUENCE: 7
agcggataac tctaaaggcc ctactttggg                                      30

<210> SEQ ID NO 8
<211> LENGTH: 30
<212> TYPE: DNA
<213> ORGANISM: Artificial Sequence
<220> FEATURE:
<223> OTHER INFORMATION: Primer

<400> SEQUENCE: 8
agcggataac aaaggtgccc agaaagaagc                                      30

<210> SEQ ID NO 9
<211> LENGTH: 18
<212> TYPE: DNA
<213> ORGANISM: Artificial Sequence
<220> FEATURE:
<223> OTHER INFORMATION: Primer

<400> SEQUENCE: 9
ctgaccctgg gaggaagc                                                   18

<210> SEQ ID NO 10
<211> LENGTH: 30
<212> TYPE: DNA
<213> ORGANISM: Artificial Sequence
<220> FEATURE:
<223> OTHER INFORMATION: Primer

<400> SEQUENCE: 10
agcggataac ccataaattc tgaccctggc                                      30

<210> SEQ ID NO 11
<211> LENGTH: 30
<212> TYPE: DNA
<213> ORGANISM: Artificial Sequence
<220> FEATURE:
<223> OTHER INFORMATION: Primer

<400> SEQUENCE: 11
agcggataac aggaggagta agcaaggaac                                      30

<210> SEQ ID NO 12
<211> LENGTH: 19
<212> TYPE: DNA
<213> ORGANISM: Artificial Sequence
<220> FEATURE:
<223> OTHER INFORMATION: Primer

<400> SEQUENCE: 12
ttctgaccct ggcaggtcc                                                  19

<210> SEQ ID NO 13
<211> LENGTH: 17
<212> TYPE: DNA
<213> ORGANISM: Artificial Sequence
<220> FEATURE:
<223> OTHER INFORMATION: Primer

<400> SEQUENCE: 13
cagctgcgcc tggaaag                                                    17
```

```
<210> SEQ ID NO 14
<211> LENGTH: 18
<212> TYPE: DNA
<213> ORGANISM: Artificial Sequence
<220> FEATURE:
<223> OTHER INFORMATION: Primer

<400> SEQUENCE: 14
gggaggcgct ttggaagt                                                 18

<210> SEQ ID NO 15
<211> LENGTH: 16
<212> TYPE: DNA
<213> ORGANISM: Artificial Sequence
<220> FEATURE:
<223> OTHER INFORMATION: Primer

<400> SEQUENCE: 15
tgtaggcacc cccccg                                                   16

<210> SEQ ID NO 16
<211> LENGTH: 16
<212> TYPE: DNA
<213> ORGANISM: Artificial Sequence
<220> FEATURE:
<223> OTHER INFORMATION: Primer

<400> SEQUENCE: 16
tgtaggcacc cacccg                                                   16

<210> SEQ ID NO 17
<211> LENGTH: 22
<212> TYPE: DNA
<213> ORGANISM: Artificial Sequence
<220> FEATURE:
<223> OTHER INFORMATION: Primer

<400> SEQUENCE: 17
gcaaaaggtg cccagaaaga ag                                            22

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
tcccctgtac cctggtcttc                                               20

<210> SEQ ID NO 19
<211> LENGTH: 17
<212> TYPE: DNA
<213> ORGANISM: Artificial Sequence
<220> FEATURE:
<223> OTHER INFORMATION: Primer

<400> SEQUENCE: 19
cttctttcag cttcctc                                                  17

<210> SEQ ID NO 20
<211> LENGTH: 15
<212> TYPE: DNA
<213> ORGANISM: Artificial Sequence
<220> FEATURE:
<223> OTHER INFORMATION: Primer
```

-continued

```
<400> SEQUENCE: 20
tctttcggct cctc                                                        15

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
acgcaggcgc accgcagaca                                                  20

<210> SEQ ID NO 22
<211> LENGTH: 21
<212> TYPE: DNA
<213> ORGANISM: Artificial Sequence
<220> FEATURE:
<223> OTHER INFORMATION: Primer

<400> SEQUENCE: 22
agctgcgcct ggaaagcgag c                                                21

<210> SEQ ID NO 23
<211> LENGTH: 23
<212> TYPE: DNA
<213> ORGANISM: Artificial Sequence
<220> FEATURE:
<223> OTHER INFORMATION: Primer

<400> SEQUENCE: 23
aggcggcact aggcaggtgc aac                                              23

<210> SEQ ID NO 24
<211> LENGTH: 28
<212> TYPE: DNA
<213> ORGANISM: Artificial Sequence
<220> FEATURE:
<223> OTHER INFORMATION: Primer

<400> SEQUENCE: 24
tcgtagatct tgtagggctg aggtggca                                         28

<210> SEQ ID NO 25
<211> LENGTH: 32
<212> TYPE: DNA
<213> ORGANISM: Artificial Sequence
<220> FEATURE:
<223> OTHER INFORMATION: Primer

<400> SEQUENCE: 25
ccatgaacca gtccatccca gtggctccca cc                                    32

<210> SEQ ID NO 26
<211> LENGTH: 24
<212> TYPE: DNA
<213> ORGANISM: Artificial Sequence
<220> FEATURE:
<223> OTHER INFORMATION: Primer

<400> SEQUENCE: 26
gaaacttgat ctccaggtcg gtca                                             24

<210> SEQ ID NO 27
<211> LENGTH: 22
<212> TYPE: DNA
```

```
<213> ORGANISM: Artificial Sequence
<220> FEATURE:
<223> OTHER INFORMATION: Primer

<400> SEQUENCE: 27
ctgagaacat ctccagcagc ag                                              22

<210> SEQ ID NO 28
<211> LENGTH: 30
<212> TYPE: DNA
<213> ORGANISM: Artificial Sequence
<220> FEATURE:
<223> OTHER INFORMATION: Primer

<400> SEQUENCE: 28
agcggataac agacagccca ggagagaaag                                      30

<210> SEQ ID NO 29
<211> LENGTH: 30
<212> TYPE: DNA
<213> ORGANISM: Artificial Sequence
<220> FEATURE:
<223> OTHER INFORMATION: Primer

<400> SEQUENCE: 29
agcggataac tcctacctct gggtttcctg                                      30

<210> SEQ ID NO 30
<211> LENGTH: 16
<212> TYPE: DNA
<213> ORGANISM: Artificial Sequence
<220> FEATURE:
<223> OTHER INFORMATION: Primer

<400> SEQUENCE: 30
tctccttctt ggccca                                                     16

<210> SEQ ID NO 31
<211> LENGTH: 30
<212> TYPE: DNA
<213> ORGANISM: Artificial Sequence
<220> FEATURE:
<223> OTHER INFORMATION: Primer

<400> SEQUENCE: 31
agcggataac attcactgcc ttgtagctcg                                      30

<210> SEQ ID NO 32
<211> LENGTH: 30
<212> TYPE: DNA
<213> ORGANISM: Artificial Sequence
<220> FEATURE:
<223> OTHER INFORMATION: Primer

<400> SEQUENCE: 32
agcggataac gtctatcagg taccaaaggc                                      30

<210> SEQ ID NO 33
<211> LENGTH: 16
<212> TYPE: DNA
<213> ORGANISM: Artificial Sequence
<220> FEATURE:
<223> OTHER INFORMATION: Primer

<400> SEQUENCE: 33
agctcggaaa tggttc                                                     16
```

```
<210> SEQ ID NO 34
<211> LENGTH: 29
<212> TYPE: DNA
<213> ORGANISM: Artificial Sequence
<220> FEATURE:
<223> OTHER INFORMATION: Primer

<400> SEQUENCE: 34
agcggataac tccagctgcg cctggaaag                                    29

<210> SEQ ID NO 35
<211> LENGTH: 30
<212> TYPE: DNA
<213> ORGANISM: Artificial Sequence
<220> FEATURE:
<223> OTHER INFORMATION: Primer

<400> SEQUENCE: 35
agcggataac aggcgctttg gaagtcccag                                   30

<210> SEQ ID NO 36
<211> LENGTH: 16
<212> TYPE: DNA
<213> ORGANISM: Artificial Sequence
<220> FEATURE:
<223> OTHER INFORMATION: Primer

<400> SEQUENCE: 36
ggaaagcgag ctcggg                                                  16

<210> SEQ ID NO 37
<211> LENGTH: 30
<212> TYPE: DNA
<213> ORGANISM: Artificial Sequence
<220> FEATURE:
<223> OTHER INFORMATION: Primer

<400> SEQUENCE: 37
agcggataac ttcctgctac tgttagtccc                                   30

<210> SEQ ID NO 38
<211> LENGTH: 30
<212> TYPE: DNA
<213> ORGANISM: Artificial Sequence
<220> FEATURE:
<223> OTHER INFORMATION: Primer

<400> SEQUENCE: 38
agcggataac tcacagatct gcagacatgg                                   30

<210> SEQ ID NO 39
<211> LENGTH: 17
<212> TYPE: DNA
<213> ORGANISM: Artificial Sequence
<220> FEATURE:
<223> OTHER INFORMATION: Primer

<400> SEQUENCE: 39
ctcaacattc cttgctg                                                 17

<210> SEQ ID NO 40
<211> LENGTH: 30
<212> TYPE: DNA
<213> ORGANISM: Artificial Sequence
<220> FEATURE:
<223> OTHER INFORMATION: Primer
```

-continued

<210> SEQ ID NO 40
<211> LENGTH: 30
<212> TYPE: DNA
<213> ORGANISM: Artificial Sequence
<220> FEATURE:
<223> OTHER INFORMATION: Primer

<400> SEQUENCE: 40
agcggataac tggactgaga gaatgaacgg                                30

<210> SEQ ID NO 41
<211> LENGTH: 30
<212> TYPE: DNA
<213> ORGANISM: Artificial Sequence
<220> FEATURE:
<223> OTHER INFORMATION: Primer

<400> SEQUENCE: 41
agcggataac gctttctatc gtggtcacat                                30

<210> SEQ ID NO 42
<211> LENGTH: 18
<212> TYPE: DNA
<213> ORGANISM: Artificial Sequence
<220> FEATURE:
<223> OTHER INFORMATION: Primer

<400> SEQUENCE: 42
tatgaccctg gcaggtcc                                             18

<210> SEQ ID NO 43
<211> LENGTH: 30
<212> TYPE: DNA
<213> ORGANISM: Artificial Sequence
<220> FEATURE:
<223> OTHER INFORMATION: Primer

<400> SEQUENCE: 43
agcggataac acctcattct gaagtctgcc                                30

<210> SEQ ID NO 44
<211> LENGTH: 30
<212> TYPE: DNA
<213> ORGANISM: Artificial Sequence
<220> FEATURE:
<223> OTHER INFORMATION: Primer

<400> SEQUENCE: 44
agcggataac ttaaagcagt agctcccttg                                30

<210> SEQ ID NO 45
<211> LENGTH: 18
<212> TYPE: DNA
<213> ORGANISM: Artificial Sequence
<220> FEATURE:
<223> OTHER INFORMATION: Primer

<400> SEQUENCE: 45
aaagtctggc gttttaac                                             18

<210> SEQ ID NO 46
<211> LENGTH: 30
<212> TYPE: DNA
<213> ORGANISM: Artificial Sequence
<220> FEATURE:
<223> OTHER INFORMATION: Primer

<400> SEQUENCE: 46
agcggataac ccttcctccc catttcttac                                30

<210> SEQ ID NO 47
<211> LENGTH: 30
<212> TYPE: DNA

```
<213> ORGANISM: Artificial Sequence
<220> FEATURE:
<223> OTHER INFORMATION: Primer

<400> SEQUENCE: 47
agcggataac aggtgtccat gtaacagtgc                                  30

<210> SEQ ID NO 48
<211> LENGTH: 19
<212> TYPE: DNA
<213> ORGANISM: Artificial Sequence
<220> FEATURE:
<223> OTHER INFORMATION: Primer

<400> SEQUENCE: 48
ccccatttct tactaacac                                              19

<210> SEQ ID NO 49
<211> LENGTH: 30
<212> TYPE: DNA
<213> ORGANISM: Artificial Sequence
<220> FEATURE:
<223> OTHER INFORMATION: Primer

<400> SEQUENCE: 49
agcggataac ctcatctcta ctggagatgg                                  30

<210> SEQ ID NO 50
<211> LENGTH: 30
<212> TYPE: DNA
<213> ORGANISM: Artificial Sequence
<220> FEATURE:
<223> OTHER INFORMATION: Primer

<400> SEQUENCE: 50
agcggataac cctcgtctgc aggtccttat                                  30

<210> SEQ ID NO 51
<211> LENGTH: 20
<212> TYPE: DNA
<213> ORGANISM: Artificial Sequence
<220> FEATURE:
<223> OTHER INFORMATION: Primer

<400> SEQUENCE: 51
cctgctattc catctccttc                                             20

<210> SEQ ID NO 52
<211> LENGTH: 30
<212> TYPE: DNA
<213> ORGANISM: Artificial Sequence
<220> FEATURE:
<223> OTHER INFORMATION: Primer

<400> SEQUENCE: 52
agcggataac ccagccagga agcaattctt                                  30

<210> SEQ ID NO 53
<211> LENGTH: 30
<212> TYPE: DNA
<213> ORGANISM: Artificial Sequence
<220> FEATURE:
<223> OTHER INFORMATION: Primer

<400> SEQUENCE: 53
agcggataac ttgaatcctt ggctgtaggc                                  30
```

```
<210> SEQ ID NO 54
<211> LENGTH: 20
<212> TYPE: DNA
<213> ORGANISM: Artificial Sequence
<220> FEATURE:
<223> OTHER INFORMATION: Primer

<400> SEQUENCE: 54
attcttaata tgcttgcctt                                              20

<210> SEQ ID NO 55
<211> LENGTH: 30
<212> TYPE: DNA
<213> ORGANISM: Artificial Sequence
<220> FEATURE:
<223> OTHER INFORMATION: Primer

<400> SEQUENCE: 55
agcggataac atctttactg ccctagggtg                                   30

<210> SEQ ID NO 56
<211> LENGTH: 29
<212> TYPE: DNA
<213> ORGANISM: Artificial Sequence
<220> FEATURE:
<223> OTHER INFORMATION: Primer

<400> SEQUENCE: 56
agcggataac gtcacaggct tcagctagg                                    29

<210> SEQ ID NO 57
<211> LENGTH: 20
<212> TYPE: DNA
<213> ORGANISM: Artificial Sequence
<220> FEATURE:
<223> OTHER INFORMATION: Primer

<400> SEQUENCE: 57
attacagtaa gaaaaagccc                                              20

<210> SEQ ID NO 58
<211> LENGTH: 30
<212> TYPE: DNA
<213> ORGANISM: Artificial Sequence
<220> FEATURE:
<223> OTHER INFORMATION: Primer

<400> SEQUENCE: 58
agcggataac tggactctgg tgtgtaggtg                                   30

<210> SEQ ID NO 59
<211> LENGTH: 30
<212> TYPE: DNA
<213> ORGANISM: Artificial Sequence
<220> FEATURE:
<223> OTHER INFORMATION: Primer

<400> SEQUENCE: 59
agcggataac gaaatagacc agagaccagg                                   30

<210> SEQ ID NO 60
<211> LENGTH: 20
<212> TYPE: DNA
<213> ORGANISM: Artificial Sequence
<220> FEATURE:
<223> OTHER INFORMATION: Primer
```

```
<400> SEQUENCE: 60
atggtgtgta ggtgatcctg                                              20

<210> SEQ ID NO 61
<211> LENGTH: 30
<212> TYPE: DNA
<213> ORGANISM: Artificial Sequence
<220> FEATURE:
<223> OTHER INFORMATION: Primer

<400> SEQUENCE: 61
agcggataac tcctcacagc accataagtc                                   30

<210> SEQ ID NO 62
<211> LENGTH: 30
<212> TYPE: DNA
<213> ORGANISM: Artificial Sequence
<220> FEATURE:
<223> OTHER INFORMATION: Primer

<400> SEQUENCE: 62
agcggataac agcagcagct gccattccat                                   30

<210> SEQ ID NO 63
<211> LENGTH: 21
<212> TYPE: DNA
<213> ORGANISM: Artificial Sequence
<220> FEATURE:
<223> OTHER INFORMATION: Primer

<400> SEQUENCE: 63
ggccacccca ctgtttagag g                                            21

<210> SEQ ID NO 64
<211> LENGTH: 30
<212> TYPE: DNA
<213> ORGANISM: Artificial Sequence
<220> FEATURE:
<223> OTHER INFORMATION: Primer

<400> SEQUENCE: 64
agcggataac aattcatacc tcctgccctg                                   30

<210> SEQ ID NO 65
<211> LENGTH: 30
<212> TYPE: DNA
<213> ORGANISM: Artificial Sequence
<220> FEATURE:
<223> OTHER INFORMATION: Primer

<400> SEQUENCE: 65
agcggataac accctccaga tgtaatgagc                                   30

<210> SEQ ID NO 66
<211> LENGTH: 22
<212> TYPE: DNA
<213> ORGANISM: Artificial Sequence
<220> FEATURE:
<223> OTHER INFORMATION: Primer

<400> SEQUENCE: 66
ccacctcctg ccctggtcaa aa                                           22

<210> SEQ ID NO 67
<211> LENGTH: 31
<212> TYPE: DNA
```

```
<213> ORGANISM: Artificial Sequence
<220> FEATURE:
<223> OTHER INFORMATION: Primer

<400> SEQUENCE: 67
agcggataac ccttttacta ctaccagttg c                                31

<210> SEQ ID NO 68
<211> LENGTH: 30
<212> TYPE: DNA
<213> ORGANISM: Artificial Sequence
<220> FEATURE:
<223> OTHER INFORMATION: Primer

<400> SEQUENCE: 68
agcggataac ccagttggca tccgaaacag                                  30

<210> SEQ ID NO 69
<211> LENGTH: 22
<212> TYPE: DNA
<213> ORGANISM: Artificial Sequence
<220> FEATURE:
<223> OTHER INFORMATION: Primer

<400> SEQUENCE: 69
cactaccagt tgctcccatg ct                                          22

<210> SEQ ID NO 70
<211> LENGTH: 30
<212> TYPE: DNA
<213> ORGANISM: Artificial Sequence
<220> FEATURE:
<223> OTHER INFORMATION: Primer

<400> SEQUENCE: 70
agcggataac gaaagaaaca gctgagtctg                                  30

<210> SEQ ID NO 71
<211> LENGTH: 30
<212> TYPE: DNA
<213> ORGANISM: Artificial Sequence
<220> FEATURE:
<223> OTHER INFORMATION: Primer

<400> SEQUENCE: 71
agcggataac cttgagagtc caagaacctg                                  30

<210> SEQ ID NO 72
<211> LENGTH: 22
<212> TYPE: DNA
<213> ORGANISM: Artificial Sequence
<220> FEATURE:
<223> OTHER INFORMATION: Primer

<400> SEQUENCE: 72
ggctgagtct gttttaaca tt                                           22

<210> SEQ ID NO 73
<211> LENGTH: 30
<212> TYPE: DNA
<213> ORGANISM: Artificial Sequence
<220> FEATURE:
<223> OTHER INFORMATION: Primer

<400> SEQUENCE: 73
agcggataac gctaaacctg cacataggac                                  30
```

```
<210> SEQ ID NO 74
<211> LENGTH: 30
<212> TYPE: DNA
<213> ORGANISM: Artificial Sequence
<220> FEATURE:
<223> OTHER INFORMATION: Primer

<400> SEQUENCE: 74
agcggataac accctcacct cacctaattg                                    30

<210> SEQ ID NO 75
<211> LENGTH: 22
<212> TYPE: DNA
<213> ORGANISM: Artificial Sequence
<220> FEATURE:
<223> OTHER INFORMATION: Primer

<400> SEQUENCE: 75
caggctcgag acactggagc tg                                            22

<210> SEQ ID NO 76
<211> LENGTH: 29
<212> TYPE: DNA
<213> ORGANISM: Artificial Sequence
<220> FEATURE:
<223> OTHER INFORMATION: Primer

<400> SEQUENCE: 76
agcggataac gtggcttccg acttctggt                                     29

<210> SEQ ID NO 77
<211> LENGTH: 30
<212> TYPE: DNA
<213> ORGANISM: Artificial Sequence
<220> FEATURE:
<223> OTHER INFORMATION: Primer

<400> SEQUENCE: 77
agcggataac aaaaggaaca ttgagggcgg                                    30

<210> SEQ ID NO 78
<211> LENGTH: 23
<212> TYPE: DNA
<213> ORGANISM: Artificial Sequence
<220> FEATURE:
<223> OTHER INFORMATION: Primer

<400> SEQUENCE: 78
tcttccgact tctggtcttt atg                                           23

<210> SEQ ID NO 79
<211> LENGTH: 31
<212> TYPE: DNA
<213> ORGANISM: Artificial Sequence
<220> FEATURE:
<223> OTHER INFORMATION: Primer

<400> SEQUENCE: 79
agcggataac ccggcctttg taaacaaaat c                                  31

<210> SEQ ID NO 80
<211> LENGTH: 30
<212> TYPE: DNA
<213> ORGANISM: Artificial Sequence
<220> FEATURE:
<223> OTHER INFORMATION: Primer
```

```
<400> SEQUENCE: 80
agcggataac gtaggctgct acaacaacac                                         30

<210> SEQ ID NO 81
<211> LENGTH: 23
<212> TYPE: DNA
<213> ORGANISM: Artificial Sequence
<220> FEATURE:
<223> OTHER INFORMATION: Primer

<400> SEQUENCE: 81
ggaggaaact tatgagagcc gta                                                23

<210> SEQ ID NO 82
<211> LENGTH: 30
<212> TYPE: DNA
<213> ORGANISM: Artificial Sequence
<220> FEATURE:
<223> OTHER INFORMATION: Primer

<400> SEQUENCE: 82
agcggataac ggccttcata aacactcacc                                         30

<210> SEQ ID NO 83
<211> LENGTH: 30
<212> TYPE: DNA
<213> ORGANISM: Artificial Sequence
<220> FEATURE:
<223> OTHER INFORMATION: Primer

<400> SEQUENCE: 83
agcggataac attccacacc cttgcttcag                                         30

<210> SEQ ID NO 84
<211> LENGTH: 24
<212> TYPE: DNA
<213> ORGANISM: Artificial Sequence
<220> FEATURE:
<223> OTHER INFORMATION: Primer

<400> SEQUENCE: 84
aaacactcac ctggctggct ttgc                                               24

<210> SEQ ID NO 85
<211> LENGTH: 30
<212> TYPE: DNA
<213> ORGANISM: Artificial Sequence
<220> FEATURE:
<223> OTHER INFORMATION: Primer

<400> SEQUENCE: 85
agcggataac gaagagtaat ttgcccctg                                          30

<210> SEQ ID NO 86
<211> LENGTH: 24
<212> TYPE: DNA
<213> ORGANISM: Artificial Sequence
<220> FEATURE:
<223> OTHER INFORMATION: Primer

<400> SEQUENCE: 86
tgagaagtgt acacccttat tcta                                               24

<210> SEQ ID NO 87
<211> LENGTH: 24
<212> TYPE: DNA
```

```
<213> ORGANISM: Artificial Sequence
<220> FEATURE:
<223> OTHER INFORMATION: Primer

<400> SEQUENCE: 87
tgagaagtgt acacccttat tcta                                          24

<210> SEQ ID NO 88
<211> LENGTH: 30
<212> TYPE: DNA
<213> ORGANISM: Artificial Sequence
<220> FEATURE:
<223> OTHER INFORMATION: Primer

<400> SEQUENCE: 88
agcggataac ggtgaatgtt tcagttctgg                                    30

<210> SEQ ID NO 89
<211> LENGTH: 30
<212> TYPE: DNA
<213> ORGANISM: Artificial Sequence
<220> FEATURE:
<223> OTHER INFORMATION: Primer

<400> SEQUENCE: 89
agcggataac tggtttcctg gtgaactttc                                    30

<210> SEQ ID NO 90
<211> LENGTH: 25
<212> TYPE: DNA
<213> ORGANISM: Artificial Sequence
<220> FEATURE:
<223> OTHER INFORMATION: Primer

<400> SEQUENCE: 90
ccctctgttt agtcttcctt ttttt                                         25

<210> SEQ ID NO 91
<211> LENGTH: 29
<212> TYPE: DNA
<213> ORGANISM: Artificial Sequence
<220> FEATURE:
<223> OTHER INFORMATION: Primer

<400> SEQUENCE: 91
agcggataac tccatataca cacatgtgc                                     29

<210> SEQ ID NO 92
<211> LENGTH: 30
<212> TYPE: DNA
<213> ORGANISM: Artificial Sequence
<220> FEATURE:
<223> OTHER INFORMATION: Primer

<400> SEQUENCE: 92
agcggataac ctgtgctctc tccaataatc                                    30

<210> SEQ ID NO 93
<211> LENGTH: 25
<212> TYPE: DNA
<213> ORGANISM: Artificial Sequence
<220> FEATURE:
<223> OTHER INFORMATION: Primer

<400> SEQUENCE: 93
gatcaaaaac tattatgcga ggtac                                         25
```

```
<210> SEQ ID NO 94
<211> LENGTH: 30
<212> TYPE: DNA
<213> ORGANISM: Artificial Sequence
<220> FEATURE:
<223> OTHER INFORMATION: Primer

<400> SEQUENCE: 94
agcggataac actgtgttct agggcgagag                               30

<210> SEQ ID NO 95
<211> LENGTH: 30
<212> TYPE: DNA
<213> ORGANISM: Artificial Sequence
<220> FEATURE:
<223> OTHER INFORMATION: Primer

<400> SEQUENCE: 95
agcggataac acacaaatga gggcgcagtg                               30

<210> SEQ ID NO 96
<211> LENGTH: 17
<212> TYPE: DNA
<213> ORGANISM: Artificial Sequence
<220> FEATURE:
<223> OTHER INFORMATION: Primer

<400> SEQUENCE: 96
caccctcgcc aggggtg                                             17

<210> SEQ ID NO 97
<211> LENGTH: 30
<212> TYPE: DNA
<213> ORGANISM: Artificial Sequence
<220> FEATURE:
<223> OTHER INFORMATION: Primer

<400> SEQUENCE: 97
agcggataac ctgatgtcta ataggccctg                               30

<210> SEQ ID NO 98
<211> LENGTH: 30
<212> TYPE: DNA
<213> ORGANISM: Artificial Sequence
<220> FEATURE:
<223> OTHER INFORMATION: Primer

<400> SEQUENCE: 98
agcggataac agcatttcac ggcaggaaag                               30

<210> SEQ ID NO 99
<211> LENGTH: 17
<212> TYPE: DNA
<213> ORGANISM: Artificial Sequence
<220> FEATURE:
<223> OTHER INFORMATION: Primer

<400> SEQUENCE: 99
tcagggtggt agggaca                                             17

<210> SEQ ID NO 100
<211> LENGTH: 30
<212> TYPE: DNA
<213> ORGANISM: Artificial Sequence
<220> FEATURE:
<223> OTHER INFORMATION: Primer
```

```
<400> SEQUENCE: 100
agcggataac gggagttggg ttactctttc                              30

<210> SEQ ID NO 101
<211> LENGTH: 30
<212> TYPE: DNA
<213> ORGANISM: Artificial Sequence
<220> FEATURE:
<223> OTHER INFORMATION: Primer

<400> SEQUENCE: 101
agcggataac caggtcagga aactgtctac                              30

<210> SEQ ID NO 102
<211> LENGTH: 19
<212> TYPE: DNA
<213> ORGANISM: Artificial Sequence
<220> FEATURE:
<223> OTHER INFORMATION: Primer

<400> SEQUENCE: 102
tcagttaaac agtgtggta                                         19

<210> SEQ ID NO 103
<211> LENGTH: 30
<212> TYPE: DNA
<213> ORGANISM: Artificial Sequence
<220> FEATURE:
<223> OTHER INFORMATION: Primer

<400> SEQUENCE: 103
agcggataac ttttcccctg taccctggtc                              30

<210> SEQ ID NO 104
<211> LENGTH: 30
<212> TYPE: DNA
<213> ORGANISM: Artificial Sequence
<220> FEATURE:
<223> OTHER INFORMATION: Primer

<400> SEQUENCE: 104
agcggataac gcaaaaggtg cccagaaaga                              30

<210> SEQ ID NO 105
<211> LENGTH: 21
<212> TYPE: DNA
<213> ORGANISM: Artificial Sequence
<220> FEATURE:
<223> OTHER INFORMATION: Primer

<400> SEQUENCE: 105
accctgaccc tgggaggaag c                                      21

<210> SEQ ID NO 106
<211> LENGTH: 30
<212> TYPE: DNA
<213> ORGANISM: Artificial Sequence
<220> FEATURE:
<223> OTHER INFORMATION: Primer

<400> SEQUENCE: 106
acgttggatg agcaggggga cccagcacca                              30

<210> SEQ ID NO 107
<211> LENGTH: 28
<212> TYPE: DNA
```

```
<213> ORGANISM: Artificial Sequence
<220> FEATURE:
<223> OTHER INFORMATION: Primer

<400> SEQUENCE: 107
acgttggatg atgtcaagtg gccgccca                                28

<210> SEQ ID NO 108
<211> LENGTH: 17
<212> TYPE: DNA
<213> ORGANISM: Artificial Sequence
<220> FEATURE:
<223> OTHER INFORMATION: Primer

<400> SEQUENCE: 108
ccagcaccac gggcggc                                            17

<210> SEQ ID NO 109
<211> LENGTH: 21
<212> TYPE: DNA
<213> ORGANISM: Artificial Sequence
<220> FEATURE:
<223> OTHER INFORMATION: Primer

<400> SEQUENCE: 109
ctcaaagagg atgtcaagtg g                                       21

<210> SEQ ID NO 110
<211> LENGTH: 18
<212> TYPE: DNA
<213> ORGANISM: Artificial Sequence
<220> FEATURE:
<223> OTHER INFORMATION: Primer

<400> SEQUENCE: 110
ggctggggtc tggagcag                                           18

<210> SEQ ID NO 111
<211> LENGTH: 20
<212> TYPE: DNA
<213> ORGANISM: Artificial Sequence
<220> FEATURE:
<223> OTHER INFORMATION: Primer

<400> SEQUENCE: 111 taccccccttc ttgagagtcc                                        20

<210> SEQ ID NO 112
<211> LENGTH: 24
<212> TYPE: DNA
<213> ORGANISM: Artificial Sequence
<220> FEATURE:
<223> OTHER INFORMATION: Primer

<400> SEQUENCE: 112
atgggagcaa ctggtagtag taaa                                    24

<210> SEQ ID NO 113
<211> LENGTH: 45
<212> TYPE: DNA
<213> ORGANISM: Artificial Sequence
<220> FEATURE:
<223> OTHER INFORMATION: Primer

<400> SEQUENCE: 113
agcgatctgc gagaccgtat aattttatg tattttggga ttaat              45
```

-continued

<210> SEQ ID NO 114
<211> LENGTH: 18
<212> TYPE: DNA
<213> ORGANISM: Artificial Sequence
<220> FEATURE:
<223> OTHER INFORMATION: Primer

<400> SEQUENCE: 114
gaggcgcttt ggaagtcc                                                        18

<210> SEQ ID NO 115
<211> LENGTH: 20
<212> TYPE: DNA
<213> ORGANISM: Artificial Sequence
<220> FEATURE:
<223> OTHER INFORMATION: Primer

<400> SEQUENCE: 115
atgaagactg gagtagggcg                                                      20

<210> SEQ ID NO 116
<211> LENGTH: 42
<212> TYPE: DNA
<213> ORGANISM: Artificial Sequence
<220> FEATURE:
<223> OTHER INFORMATION: Primer

<400> SEQUENCE: 116
ggatggcgtt ccgtcctatt gcgcaccctg ctgtaggcac cc                             42

<210> SEQ ID NO 117
<211> LENGTH: 30
<212> TYPE: DNA
<213> ORGANISM: Artificial Sequence
<220> FEATURE:
<223> OTHER INFORMATION: Primer

<400> SEQUENCE: 117
agcggataac agacagccca ggagagaaag                                           30

<210> SEQ ID NO 118
<211> LENGTH: 30
<212> TYPE: DNA
<213> ORGANISM: Artificial Sequence
<220> FEATURE:
<223> OTHER INFORMATION: Primer

<400> SEQUENCE: 118
agcggataac tcctacctct gggtttcctg                                           30

<210> SEQ ID NO 119
<211> LENGTH: 19
<212> TYPE: DNA
<213> ORGANISM: Artificial Sequence
<220> FEATURE:
<223> OTHER INFORMATION: Primer

<400> SEQUENCE: 119
ccctctcctt cttggccca                                                       19

<210> SEQ ID NO 120
<211> LENGTH: 20
<212> TYPE: DNA
<213> ORGANISM: Artificial Sequence
<220> FEATURE:
<223> OTHER INFORMATION: Primer

```
<400> SEQUENCE: 120
ccccacatga caccctattc                                              20

<210> SEQ ID NO 121
<211> LENGTH: 18
<212> TYPE: DNA
<213> ORGANISM: Artificial Sequence
<220> FEATURE:
<223> OTHER INFORMATION: Primer

<400> SEQUENCE: 121
ggctggggtc tggagcag                                                18

<210> SEQ ID NO 122
<211> LENGTH: 20
<212> TYPE: DNA
<213> ORGANISM: Artificial Sequence
<220> FEATURE:
<223> OTHER INFORMATION: Primer

<400> SEQUENCE: 122
aggtacgggg ttgtcaaatg                                              20

<210> SEQ ID NO 123
<211> LENGTH: 20
<212> TYPE: DNA
<213> ORGANISM: Artificial Sequence
<220> FEATURE:
<223> OTHER INFORMATION: Primer

<400> SEQUENCE: 123
tactccagtc ttcatcccgc                                              20

<210> SEQ ID NO 124
<211> LENGTH: 19
<212> TYPE: DNA
<213> ORGANISM: Artificial Sequence
<220> FEATURE:
<223> OTHER INFORMATION: Primer

<400> SEQUENCE: 124
ctgcagttgc caggtcagt                                               19

<210> SEQ ID NO 125
<211> LENGTH: 20
<212> TYPE: DNA
<213> ORGANISM: Artificial Sequence
<220> FEATURE:
<223> OTHER INFORMATION: Primer

<400> SEQUENCE: 125
gaaagtaagg atcgggcctc                                              20

<210> SEQ ID NO 126
<211> LENGTH: 20
<212> TYPE: DNA
<213> ORGANISM: Artificial Sequence
<220> FEATURE:
<223> OTHER INFORMATION: Primer

<400> SEQUENCE: 126
ctccttccct tcctccaaac                                              20

<210> SEQ ID NO 127
<211> LENGTH: 20
<212> TYPE: DNA
```

```
<213> ORGANISM: Artificial Sequence
<220> FEATURE:
<223> OTHER INFORMATION: Primer

<400> SEQUENCE: 127
aggcaggaga attgcttgaa                                                   20

<210> SEQ ID NO 128
<211> LENGTH: 20
<212> TYPE: DNA
<213> ORGANISM: Artificial Sequence
<220> FEATURE:
<223> OTHER INFORMATION: Primer

<400> SEQUENCE: 128
acactgtttc accctcccag                                                   20

<210> SEQ ID NO 129
<211> LENGTH: 20
<212> TYPE: DNA
<213> ORGANISM: Artificial Sequence
<220> FEATURE:
<223> OTHER INFORMATION: Primer

<400> SEQUENCE: 129
gccattcctg atatgccagt                                                   20

<210> SEQ ID NO 130
<211> LENGTH: 20
<212> TYPE: DNA
<213> ORGANISM: Artificial Sequence
<220> FEATURE:
<223> OTHER INFORMATION: Primer

<400> SEQUENCE: 130
ctggcatatc aggaatggct                                                   20

<210> SEQ ID NO 131
<211> LENGTH: 20
<212> TYPE: DNA
<213> ORGANISM: Artificial Sequence
<220> FEATURE:
<223> OTHER INFORMATION: Primer

<400> SEQUENCE: 131
agacctacca agccccaact                                                   20

<210> SEQ ID NO 132
<211> LENGTH: 20
<212> TYPE: DNA
<213> ORGANISM: Artificial Sequence
<220> FEATURE:
<223> OTHER INFORMATION: Primer

<400> SEQUENCE: 132
ttctcctggg attctgaacg                                                   20

<210> SEQ ID NO 133
<211> LENGTH: 20
<212> TYPE: DNA
<213> ORGANISM: Artificial Sequence
<220> FEATURE:
<223> OTHER INFORMATION: Primer

<400> SEQUENCE: 133
gaatagggtg tcatgtgggg                                                   20
```

<210> SEQ ID NO 134
<211> LENGTH: 20
<212> TYPE: DNA
<213> ORGANISM: Artificial Sequence
<220> FEATURE:
<223> OTHER INFORMATION: Primer

<400> SEQUENCE: 134
ttgcctcata gttctcgcct                                                     20

<210> SEQ ID NO 135
<211> LENGTH: 20
<212> TYPE: DNA
<213> ORGANISM: Artificial Sequence
<220> FEATURE:
<223> OTHER INFORMATION: Primer

<400> SEQUENCE: 135
gtccttacga ggcagcatgt                                                     20

<210> SEQ ID NO 136
<211> LENGTH: 20
<212> TYPE: DNA
<213> ORGANISM: Artificial Sequence
<220> FEATURE:
<223> OTHER INFORMATION: Primer

<400> SEQUENCE: 136
tggtggttgg gggtctagta                                                     20

<210> SEQ ID NO 137
<211> LENGTH: 20
<212> TYPE: DNA
<213> ORGANISM: Artificial Sequence
<220> FEATURE:
<223> OTHER INFORMATION: Primer

<400> SEQUENCE: 137
atctccaggt cggtcactgt                                                     20

<210> SEQ ID NO 138
<211> LENGTH: 20
<212> TYPE: DNA
<213> ORGANISM: Artificial Sequence
<220> FEATURE:
<223> OTHER INFORMATION: Primer

<400> SEQUENCE: 138
gtaggattgg caaggagggt                                                     20

<210> SEQ ID NO 139
<211> LENGTH: 20
<212> TYPE: DNA
<213> ORGANISM: Artificial Sequence
<220> FEATURE:
<223> OTHER INFORMATION: Primer

<400> SEQUENCE: 139
ttccccaaag cagaagaaga                                                     20

<210> SEQ ID NO 140
<211> LENGTH: 20
<212> TYPE: DNA
<213> ORGANISM: Artificial Sequence
<220> FEATURE:
<223> OTHER INFORMATION: Primer

```
<400> SEQUENCE: 140
aggacatccc cagtgacaag                                               20

<210> SEQ ID NO 141
<211> LENGTH: 20
<212> TYPE: DNA
<213> ORGANISM: Artificial Sequence
<220> FEATURE:
<223> OTHER INFORMATION: Primer

<400> SEQUENCE: 141
ggggtgagta atagaccgca                                               20

<210> SEQ ID NO 142
<211> LENGTH: 20
<212> TYPE: DNA
<213> ORGANISM: Artificial Sequence
<220> FEATURE:
<223> OTHER INFORMATION: Primer

<400> SEQUENCE: 142
cctgagcagt gtgaacttgg                                               20

<210> SEQ ID NO 143
<211> LENGTH: 20
<212> TYPE: DNA
<213> ORGANISM: Artificial Sequence
<220> FEATURE:
<223> OTHER INFORMATION: Primer

<400> SEQUENCE: 143
gggagagttc tttccctgct                                               20

<210> SEQ ID NO 144
<211> LENGTH: 20
<212> TYPE: DNA
<213> ORGANISM: Artificial Sequence
<220> FEATURE:
<223> OTHER INFORMATION: Primer

<400> SEQUENCE: 144
tggagatgtt ctcaggggag                                               20

<210> SEQ ID NO 145
<211> LENGTH: 20
<212> TYPE: DNA
<213> ORGANISM: Artificial Sequence
<220> FEATURE:
<223> OTHER INFORMATION: Primer

<400> SEQUENCE: 145
cagaggacag ggagatgagg                                               20

<210> SEQ ID NO 146
<211> LENGTH: 20
<212> TYPE: DNA
<213> ORGANISM: Artificial Sequence
<220> FEATURE:
<223> OTHER INFORMATION: Primer

<400> SEQUENCE: 146
tttcctggaa gtggatttgg                                               20

<210> SEQ ID NO 147
<211> LENGTH: 20
<212> TYPE: DNA
```

```
<213> ORGANISM: Artificial Sequence
<220> FEATURE:
<223> OTHER INFORMATION: Primer

<400> SEQUENCE: 147
ttatgaaggc ccaactgacc                                               20

<210> SEQ ID NO 148
<211> LENGTH: 20
<212> TYPE: DNA
<213> ORGANISM: Artificial Sequence
<220> FEATURE:
<223> OTHER INFORMATION: Primer

<400> SEQUENCE: 148
agagtgttgt gggccaagtc                                               20

<210> SEQ ID NO 149
<211> LENGTH: 20
<212> TYPE: DNA
<213> ORGANISM: Artificial Sequence
<220> FEATURE:
<223> OTHER INFORMATION: Primer

<400> SEQUENCE: 149
actcactcac tgtccccacc                                               20

<210> SEQ ID NO 150
<211> LENGTH: 20
<212> TYPE: DNA
<213> ORGANISM: Artificial Sequence
<220> FEATURE:
<223> OTHER INFORMATION: Primer

<400> SEQUENCE: 150
actaccagtt gctcccatgc                                               20

<210> SEQ ID NO 151
<211> LENGTH: 20
<212> TYPE: DNA
<213> ORGANISM: Artificial Sequence
<220> FEATURE:
<223> OTHER INFORMATION: Primer

<400> SEQUENCE: 151
ttgcgttgct gtaaacgaag                                               20

<210> SEQ ID NO 152
<211> LENGTH: 20
<212> TYPE: DNA
<213> ORGANISM: Artificial Sequence
<220> FEATURE:
<223> OTHER INFORMATION: Primer

<400> SEQUENCE: 152
ctgaagcaag ggtgtggaat                                               20

<210> SEQ ID NO 153
<211> LENGTH: 20
<212> TYPE: DNA
<213> ORGANISM: Artificial Sequence
<220> FEATURE:
<223> OTHER INFORMATION: Primer

<400> SEQUENCE: 153
caggccactt aaccatgtga                                               20
```

```
<210> SEQ ID NO 154
<211> LENGTH: 20
<212> TYPE: DNA
<213> ORGANISM: Artificial Sequence
<220> FEATURE:
<223> OTHER INFORMATION: Primer

<400> SEQUENCE: 154
gctccagata cgaccagcat                                               20

<210> SEQ ID NO 155
<211> LENGTH: 20
<212> TYPE: DNA
<213> ORGANISM: Artificial Sequence
<220> FEATURE:
<223> OTHER INFORMATION: Primer

<400> SEQUENCE: 155
gaactttgac cttccctccc                                               20

<210> SEQ ID NO 156
<211> LENGTH: 20
<212> TYPE: DNA
<213> ORGANISM: Artificial Sequence
<220> FEATURE:
<223> OTHER INFORMATION: Primer

<400> SEQUENCE: 156
gtcaacaggc agcaggtgta                                               20

<210> SEQ ID NO 157
<211> LENGTH: 20
<212> TYPE: DNA
<213> ORGANISM: Artificial Sequence
<220> FEATURE:
<223> OTHER INFORMATION: Primer

<400> SEQUENCE: 157
tggtgaaacc ccgtctctac                                               20

<210> SEQ ID NO 158
<211> LENGTH: 20
<212> TYPE: DNA
<213> ORGANISM: Artificial Sequence
<220> FEATURE:
<223> OTHER INFORMATION: Primer

<400> SEQUENCE: 158
tggtgaaacc ccgtctctac                                               20

<210> SEQ ID NO 159
<211> LENGTH: 20
<212> TYPE: DNA
<213> ORGANISM: Artificial Sequence
<220> FEATURE:
<223> OTHER INFORMATION: Primer

<400> SEQUENCE: 159
atggaatgtt cttcgcttgg                                               20

<210> SEQ ID NO 160
<211> LENGTH: 20
<212> TYPE: DNA
<213> ORGANISM: Artificial Sequence
<220> FEATURE:
<223> OTHER INFORMATION: Primer
```

```
<400> SEQUENCE: 160
catcaaaatt gaaacccgct                                          20

<210> SEQ ID NO 161
<211> LENGTH: 20
<212> TYPE: DNA
<213> ORGANISM: Artificial Sequence
<220> FEATURE:
<223> OTHER INFORMATION: Primer

<400> SEQUENCE: 161
ttctcatcct caaaccctgc                                          20

<210> SEQ ID NO 162
<211> LENGTH: 20
<212> TYPE: DNA
<213> ORGANISM: Artificial Sequence
<220> FEATURE:
<223> OTHER INFORMATION: Primer

<400> SEQUENCE: 162
ccctggcaat ccataacaaa                                          20

<210> SEQ ID NO 163
<211> LENGTH: 20
<212> TYPE: DNA
<213> ORGANISM: Artificial Sequence
<220> FEATURE:
<223> OTHER INFORMATION: Primer

<400> SEQUENCE: 163
tagactggcc actggctctt                                          20

<210> SEQ ID NO 164
<211> LENGTH: 20
<212> TYPE: DNA
<213> ORGANISM: Artificial Sequence
<220> FEATURE:
<223> OTHER INFORMATION: Primer

<400> SEQUENCE: 164
atggaatcga aaacggttca                                          20

<210> SEQ ID NO 165
<211> LENGTH: 18
<212> TYPE: DNA
<213> ORGANISM: Artificial Sequence
<220> FEATURE:
<223> OTHER INFORMATION: Primer

<400> SEQUENCE: 165
caagctgagc tctgccca                                            18

<210> SEQ ID NO 166
<211> LENGTH: 20
<212> TYPE: DNA
<213> ORGANISM: Artificial Sequence
<220> FEATURE:
<223> OTHER INFORMATION: Primer

<400> SEQUENCE: 166
cacatctgga aggggtgtct                                          20

<210> SEQ ID NO 167
<211> LENGTH: 20
<212> TYPE: DNA
```

```
<213> ORGANISM: Artificial Sequence
<220> FEATURE:
<223> OTHER INFORMATION: Primer

<400> SEQUENCE: 167
ctagacttgg gggcagtagc                                              20

<210> SEQ ID NO 168
<211> LENGTH: 20
<212> TYPE: DNA
<213> ORGANISM: Artificial Sequence
<220> FEATURE:
<223> OTHER INFORMATION: Primer

<400> SEQUENCE: 168
ctgagttgtc ccggtctagc                                              20

<210> SEQ ID NO 169
<211> LENGTH: 20
<212> TYPE: DNA
<213> ORGANISM: Artificial Sequence
<220> FEATURE:
<223> OTHER INFORMATION: Primer

<400> SEQUENCE: 169
ggaaacagaa gccacagctc                                              20

<210> SEQ ID NO 170
<211> LENGTH: 20
<212> TYPE: DNA
<213> ORGANISM: Artificial Sequence
<220> FEATURE:
<223> OTHER INFORMATION: Primer

<400> SEQUENCE: 170
aagagccagt ggccagtcta                                              20

<210> SEQ ID NO 171
<211> LENGTH: 19
<212> TYPE: DNA
<213> ORGANISM: Artificial Sequence
<220> FEATURE:
<223> OTHER INFORMATION: Primer

<400> SEQUENCE: 171
ctcctctgtg gtccaagcc                                               19

<210> SEQ ID NO 172
<211> LENGTH: 20
<212> TYPE: DNA
<213> ORGANISM: Artificial Sequence
<220> FEATURE:
<223> OTHER INFORMATION: Primer

<400> SEQUENCE: 172
ctccttccct tcctccaaac                                              20

<210> SEQ ID NO 173
<211> LENGTH: 20
<212> TYPE: DNA
<213> ORGANISM: Artificial Sequence
<220> FEATURE:
<223> OTHER INFORMATION: Primer

<400> SEQUENCE: 173
aggcaggaga attgcttgaa                                              20
```

<210> SEQ ID NO 174
<211> LENGTH: 20
<212> TYPE: DNA
<213> ORGANISM: Artificial Sequence
<220> FEATURE:
<223> OTHER INFORMATION: Primer

<400> SEQUENCE: 174
aggacatccc cagtgacaag                                               20

<210> SEQ ID NO 175
<211> LENGTH: 20
<212> TYPE: DNA
<213> ORGANISM: Artificial Sequence
<220> FEATURE:
<223> OTHER INFORMATION: Primer

<400> SEQUENCE: 175
ggggtgagta atagaccgca                                               20

<210> SEQ ID NO 176
<211> LENGTH: 20
<212> TYPE: DNA
<213> ORGANISM: Artificial Sequence
<220> FEATURE:
<223> OTHER INFORMATION: Primer

<400> SEQUENCE: 176
aaccccgaga gaagaagctc                                               20

<210> SEQ ID NO 177
<211> LENGTH: 20
<212> TYPE: DNA
<213> ORGANISM: Artificial Sequence
<220> FEATURE:
<223> OTHER INFORMATION: Primer

<400> SEQUENCE: 177
aatccacttc caggaaaccc                                               20

<210> SEQ ID NO 178
<211> LENGTH: 20
<212> TYPE: DNA
<213> ORGANISM: Artificial Sequence
<220> FEATURE:
<223> OTHER INFORMATION: Primer

<400> SEQUENCE: 178
ctcccctctc aacagctcac                                               20

<210> SEQ ID NO 179
<211> LENGTH: 20
<212> TYPE: DNA
<213> ORGANISM: Artificial Sequence
<220> FEATURE:
<223> OTHER INFORMATION: Primer

<400> SEQUENCE: 179
tgtcatttga caaccccgta                                               20

<210> SEQ ID NO 180
<211> LENGTH: 20
<212> TYPE: DNA
<213> ORGANISM: Artificial Sequence
<220> FEATURE:
<223> OTHER INFORMATION: Primer

```
<400> SEQUENCE: 180
gtgactagag gattcccgcc                                              20

<210> SEQ ID NO 181
<211> LENGTH: 20
<212> TYPE: DNA
<213> ORGANISM: Artificial Sequence
<220> FEATURE:
<223> OTHER INFORMATION: Primer

<400> SEQUENCE: 181
tactccagtc ttcatcccgc                                              20

<210> SEQ ID NO 182
<211> LENGTH: 38
<212> TYPE: DNA
<213> ORGANISM: Artificial Sequence
<220> FEATURE:
<223> OTHER INFORMATION: Primer

<400> SEQUENCE: 182
tgtaaaacga cggccagtcc gctgaatttt ccaaaaag                          38

<210> SEQ ID NO 183
<211> LENGTH: 38
<212> TYPE: DNA
<213> ORGANISM: Artificial Sequence
<220> FEATURE:
<223> OTHER INFORMATION: Primer

<400> SEQUENCE: 183
caggaaacag ctatgaccct accttgaccg tcgacctg                          38

<210> SEQ ID NO 184
<211> LENGTH: 18
<212> TYPE: DNA
<213> ORGANISM: Artificial Sequence
<220> FEATURE:
<223> OTHER INFORMATION: Primer

<400> SEQUENCE: 184
tgtaaaacga cggccagt                                                18

<210> SEQ ID NO 185
<211> LENGTH: 18
<212> TYPE: DNA
<213> ORGANISM: Artificial Sequence
<220> FEATURE:
<223> OTHER INFORMATION: Primer

<400> SEQUENCE: 185
caggaaacag ctatgacc                                                18

<210> SEQ ID NO 186
<211> LENGTH: 39
<212> TYPE: DNA
<213> ORGANISM: Artificial Sequence
<220> FEATURE:
<223> OTHER INFORMATION: Primer

<400> SEQUENCE: 186
tgtaaaacga cggccagtgc aagagttacc aagcgaaga                         39

<210> SEQ ID NO 187
<211> LENGTH: 37
<212> TYPE: DNA
```

```
<213> ORGANISM: Artificial Sequence
<220> FEATURE:
<223> OTHER INFORMATION: Primer

<400> SEQUENCE: 187
caggaaacag ctatgaccct ccagggagat gccagac                              37

<210> SEQ ID NO 188
<211> LENGTH: 18
<212> TYPE: DNA
<213> ORGANISM: Artificial Sequence
<220> FEATURE:
<223> OTHER INFORMATION: Primer

<400> SEQUENCE: 188
tgtaaaacga cggccagt                                                   18

<210> SEQ ID NO 189
<211> LENGTH: 18
<212> TYPE: DNA
<213> ORGANISM: Artificial Sequence
<220> FEATURE:
<223> OTHER INFORMATION: Primer

<400> SEQUENCE: 189
caggaaacag ctatgacc                                                   18

<210> SEQ ID NO 190
<211> LENGTH: 38
<212> TYPE: DNA
<213> ORGANISM: Artificial Sequence
<220> FEATURE:
<223> OTHER INFORMATION: Primer

<400> SEQUENCE: 190
tgtaaaacga cggccagttg acagttttgc cattccag                             38

<210> SEQ ID NO 191
<211> LENGTH: 36
<212> TYPE: DNA
<213> ORGANISM: Artificial Sequence
<220> FEATURE:
<223> OTHER INFORMATION: Primer

<400> SEQUENCE: 191
caggaaacag ctatgaccga gggagagcag cagagc                               36

<210> SEQ ID NO 192
<211> LENGTH: 18
<212> TYPE: DNA
<213> ORGANISM: Artificial Sequence
<220> FEATURE:
<223> OTHER INFORMATION: Primer

<400> SEQUENCE: 192
tgtaaaacga cggccagt                                                   18

<210> SEQ ID NO 193
<211> LENGTH: 18
<212> TYPE: DNA
<213> ORGANISM: Artificial Sequence
<220> FEATURE:
<223> OTHER INFORMATION: Primer

<400> SEQUENCE: 193
caggaaacag ctatgacc                                                   18
```

<210> SEQ ID NO 194
<211> LENGTH: 38
<212> TYPE: DNA
<213> ORGANISM: Artificial Sequence
<220> FEATURE:
<223> OTHER INFORMATION: Primer

<400> SEQUENCE: 194
tgtaaaacga cggccagtct tttggtgtca ggcagtca                         38

<210> SEQ ID NO 195
<211> LENGTH: 38
<212> TYPE: DNA
<213> ORGANISM: Artificial Sequence
<220> FEATURE:
<223> OTHER INFORMATION: Primer

<400> SEQUENCE: 195
caggaaacag ctatgacctt atgtgcgctc ctcttctg                         38

<210> SEQ ID NO 196
<211> LENGTH: 18
<212> TYPE: DNA
<213> ORGANISM: Artificial Sequence
<220> FEATURE:
<223> OTHER INFORMATION: Primer

<400> SEQUENCE: 196
tgtaaaacga cggccagt                                               18

<210> SEQ ID NO 197
<211> LENGTH: 18
<212> TYPE: DNA
<213> ORGANISM: Artificial Sequence
<220> FEATURE:
<223> OTHER INFORMATION: Primer

<400> SEQUENCE: 197
caggaaacag ctatgacc                                               18

<210> SEQ ID NO 198
<211> LENGTH: 38
<212> TYPE: DNA
<213> ORGANISM: Artificial Sequence
<220> FEATURE:
<223> OTHER INFORMATION: Primer

<400> SEQUENCE: 198
tgtaaaacga cggccagttt attctgcatc ccctggag                         38

<210> SEQ ID NO 199
<211> LENGTH: 38
<212> TYPE: DNA
<213> ORGANISM: Artificial Sequence
<220> FEATURE:
<223> OTHER INFORMATION: Primer

<400> SEQUENCE: 199
caggaaacag ctatgacctc gttggcttcc tttagcat                         38

<210> SEQ ID NO 200
<211> LENGTH: 18
<212> TYPE: DNA
<213> ORGANISM: Artificial Sequence
<220> FEATURE:
<223> OTHER INFORMATION: Primer

```
<400> SEQUENCE: 200
tgtaaaacga cggccagt                                            18

<210> SEQ ID NO 201
<211> LENGTH: 18
<212> TYPE: DNA
<213> ORGANISM: Artificial Sequence
<220> FEATURE:
<223> OTHER INFORMATION: Primer

<400> SEQUENCE: 201
caggaaacag ctatgacc                                            18

<210> SEQ ID NO 202
<211> LENGTH: 43
<212> TYPE: DNA
<213> ORGANISM: Artificial Sequence
<220> FEATURE:
<223> OTHER INFORMATION: Primer

<400> SEQUENCE: 202
tgtaaaacga cggccagttt gtaaagacag gagtctcgtt atg                 43

<210> SEQ ID NO 203
<211> LENGTH: 38
<212> TYPE: DNA
<213> ORGANISM: Artificial Sequence
<220> FEATURE:
<223> OTHER INFORMATION: Primer

<400> SEQUENCE: 203
caggaaacag ctatgacctc gtagatgagg cggaagtc                      38

<210> SEQ ID NO 204
<211> LENGTH: 18
<212> TYPE: DNA
<213> ORGANISM: Artificial Sequence
<220> FEATURE:
<223> OTHER INFORMATION: Primer

<400> SEQUENCE: 204
tgtaaaacga cggccagt                                            18

<210> SEQ ID NO 205
<211> LENGTH: 18
<212> TYPE: DNA
<213> ORGANISM: Artificial Sequence
<220> FEATURE:
<223> OTHER INFORMATION: Primer

<400> SEQUENCE: 205
caggaaacag ctatgacc                                            18

<210> SEQ ID NO 206
<211> LENGTH: 38
<212> TYPE: DNA
<213> ORGANISM: Artificial Sequence
<220> FEATURE:
<223> OTHER INFORMATION: Primer

<400> SEQUENCE: 206
tgtaaaacga cggccagtgc caaggagaca gggaaata                      38

<210> SEQ ID NO 207
<211> LENGTH: 38
<212> TYPE: DNA
```

```
<213> ORGANISM: Artificial Sequence
<220> FEATURE:
<223> OTHER INFORMATION: Primer

<400> SEQUENCE: 207
caggaaacag ctatgaccct cctctcctgc accaaaag                              38

<210> SEQ ID NO 208
<211> LENGTH: 18
<212> TYPE: DNA
<213> ORGANISM: Artificial Sequence
<220> FEATURE:
<223> OTHER INFORMATION: Primer

<400> SEQUENCE: 208
tgtaaaacga cggccagt                                                    18

<210> SEQ ID NO 209
<211> LENGTH: 18
<212> TYPE: DNA
<213> ORGANISM: Artificial Sequence
<220> FEATURE:
<223> OTHER INFORMATION: Primer

<400> SEQUENCE: 209
caggaaacag ctatgacc                                                    18

<210> SEQ ID NO 210
<211> LENGTH: 38
<212> TYPE: DNA
<213> ORGANISM: Artificial Sequence
<220> FEATURE:
<223> OTHER INFORMATION: Primer

<400> SEQUENCE: 210
tgtaaaacga cggccagttc tcctccgaca ttgactcc                              38

<210> SEQ ID NO 211
<211> LENGTH: 37
<212> TYPE: DNA
<213> ORGANISM: Artificial Sequence
<220> FEATURE:
<223> OTHER INFORMATION: Primer

<400> SEQUENCE: 211
caggaaacag ctatgaccag gcttggcaac atcctct                               37

<210> SEQ ID NO 212
<211> LENGTH: 18
<212> TYPE: DNA
<213> ORGANISM: Artificial Sequence
<220> FEATURE:
<223> OTHER INFORMATION: Primer

<400> SEQUENCE: 212
tgtaaaacga cggccagt                                                    18

<210> SEQ ID NO 213
<211> LENGTH: 18
<212> TYPE: DNA
<213> ORGANISM: Artificial Sequence
<220> FEATURE:
<223> OTHER INFORMATION: Primer

<400> SEQUENCE: 213
caggaaacag ctatgacc                                                    18
```

<210> SEQ ID NO 214
<211> LENGTH: 38
<212> TYPE: DNA
<213> ORGANISM: Artificial Sequence
<220> FEATURE:
<223> OTHER INFORMATION: Primer

<400> SEQUENCE: 214
tgtaaaacga cggccagtcc ccaggtcagt ggaataac              38

<210> SEQ ID NO 215
<211> LENGTH: 37
<212> TYPE: DNA
<213> ORGANISM: Artificial Sequence
<220> FEATURE:
<223> OTHER INFORMATION: Primer

<400> SEQUENCE: 215
caggaaacag ctatgaccag gtctggcagg agctgtt              37

<210> SEQ ID NO 216
<211> LENGTH: 18
<212> TYPE: DNA
<213> ORGANISM: Artificial Sequence
<220> FEATURE:
<223> OTHER INFORMATION: Primer

<400> SEQUENCE: 216
tgtaaaacga cggccagt              18

<210> SEQ ID NO 217
<211> LENGTH: 18
<212> TYPE: DNA
<213> ORGANISM: Artificial Sequence
<220> FEATURE:
<223> OTHER INFORMATION: Primer

<400> SEQUENCE: 217
caggaaacag ctatgacc              18

<210> SEQ ID NO 218
<211> LENGTH: 38
<212> TYPE: DNA
<213> ORGANISM: Artificial Sequence
<220> FEATURE:
<223> OTHER INFORMATION: Primer

<400> SEQUENCE: 218
tgtaaaacga cggccagtgg cttcagggag cttctctc              38

<210> SEQ ID NO 219
<211> LENGTH: 38
<212> TYPE: DNA
<213> ORGANISM: Artificial Sequence
<220> FEATURE:
<223> OTHER INFORMATION: Primer

<400> SEQUENCE: 219
caggaaacag ctatgacccc tgtagctgga ggatgagc              38

<210> SEQ ID NO 220
<211> LENGTH: 18
<212> TYPE: DNA
<213> ORGANISM: Artificial Sequence
<220> FEATURE:
<223> OTHER INFORMATION: Primer -continued

```
<400> SEQUENCE: 220
tgtaaaacga cggccagt                                                   18

<210> SEQ ID NO 221
<211> LENGTH: 18
<212> TYPE: DNA
<213> ORGANISM: Artificial Sequence
<220> FEATURE:
<223> OTHER INFORMATION: Primer

<400> SEQUENCE: 221
caggaaacag ctatgacc                                                   18

<210> SEQ ID NO 222
<211> LENGTH: 38
<212> TYPE: DNA
<213> ORGANISM: Artificial Sequence
<220> FEATURE:
<223> OTHER INFORMATION: Primer

<400> SEQUENCE: 222
tgtaaaacga cggccagtcc gacctggaga tcaagttt                              38

<210> SEQ ID NO 223
<211> LENGTH: 38
<212> TYPE: DNA
<213> ORGANISM: Artificial Sequence
<220> FEATURE:
<223> OTHER INFORMATION: Primer

<400> SEQUENCE: 223
caggaaacag ctatgacctt ccccaaagca gaagaaga                              38

<210> SEQ ID NO 224
<211> LENGTH: 18
<212> TYPE: DNA
<213> ORGANISM: Artificial Sequence
<220> FEATURE:
<223> OTHER INFORMATION: Primer

<400> SEQUENCE: 224
tgtaaaacga cggccagt                                                   18

<210> SEQ ID NO 225
<211> LENGTH: 18
<212> TYPE: DNA
<213> ORGANISM: Artificial Sequence
<220> FEATURE:
<223> OTHER INFORMATION: Primer

<400> SEQUENCE: 225
caggaaacag ctatgacc                                                   18

<210> SEQ ID NO 226
<211> LENGTH: 38
<212> TYPE: DNA
<213> ORGANISM: Artificial Sequence
<220> FEATURE:
<223> OTHER INFORMATION: Primer

<400> SEQUENCE: 226
tgtaaaacga cggccagttt gatgcagagc tcatcctg                              38

<210> SEQ ID NO 227
<211> LENGTH: 38
<212> TYPE: DNA
```

```
<213> ORGANISM: Artificial Sequence
<220> FEATURE:
<223> OTHER INFORMATION: Primer

<400> SEQUENCE: 227
caggaaacag ctatgaccga tggagctcct tgaattgc                              38

<210> SEQ ID NO 228
<211> LENGTH: 18
<212> TYPE: DNA
<213> ORGANISM: Artificial Sequence
<220> FEATURE:
<223> OTHER INFORMATION: Primer

<400> SEQUENCE: 228
tgtaaaacga cggccagt                                                    18

<210> SEQ ID NO 229
<211> LENGTH: 18
<212> TYPE: DNA
<213> ORGANISM: Artificial Sequence
<220> FEATURE:
<223> OTHER INFORMATION: Primer

<400> SEQUENCE: 229
caggaaacag ctatgacc                                                    18

<210> SEQ ID NO 230
<211> LENGTH: 38
<212> TYPE: DNA
<213> ORGANISM: Artificial Sequence
<220> FEATURE:
<223> OTHER INFORMATION: Primer

<400> SEQUENCE: 230
tgtaaaacga cggccagtca ggggagctat cttggtca                              38

<210> SEQ ID NO 231
<211> LENGTH: 38
<212> TYPE: DNA
<213> ORGANISM: Artificial Sequence
<220> FEATURE:
<223> OTHER INFORMATION: Primer

<400> SEQUENCE: 231
caggaaacag ctatgaccaa atggggcaat cacaagag                              38

<210> SEQ ID NO 232
<211> LENGTH: 18
<212> TYPE: DNA
<213> ORGANISM: Artificial Sequence
<220> FEATURE:
<223> OTHER INFORMATION: Primer

<400> SEQUENCE: 232
tgtaaaacga cggccagt                                                    18

<210> SEQ ID NO 233
<211> LENGTH: 18
<212> TYPE: DNA
<213> ORGANISM: Artificial Sequence
<220> FEATURE:
<223> OTHER INFORMATION: Primer

<400> SEQUENCE: 233
caggaaacag ctatgacc                                                    18
```

```
<210> SEQ ID NO 234
<211> LENGTH: 38
<212> TYPE: DNA
<213> ORGANISM: Artificial Sequence
<220> FEATURE:
<223> OTHER INFORMATION: Primer

<400> SEQUENCE: 234
tgtaaaacga cggccagttg gggcctagct gtatagga                              38

<210> SEQ ID NO 235
<211> LENGTH: 38
<212> TYPE: DNA
<213> ORGANISM: Artificial Sequence
<220> FEATURE:
<223> OTHER INFORMATION: Primer

<400> SEQUENCE: 235
caggaaacag ctatgaccat tccacaccct tgcttcag                              38

<210> SEQ ID NO 236
<211> LENGTH: 38
<212> TYPE: DNA
<213> ORGANISM: Artificial Sequence
<220> FEATURE:
<223> OTHER INFORMATION: Primer

<400> SEQUENCE: 236
caggaaacag ctatgaccat tccacaccct tgcttcag                              38

<210> SEQ ID NO 237
<211> LENGTH: 18
<212> TYPE: DNA
<213> ORGANISM: Artificial Sequence
<220> FEATURE:
<223> OTHER INFORMATION: Primer

<400> SEQUENCE: 237
caggaaacag ctatgacc                                                    18

<210> SEQ ID NO 238
<211> LENGTH: 38
<212> TYPE: DNA
<213> ORGANISM: Artificial Sequence
<220> FEATURE:
<223> OTHER INFORMATION: Primer

<400> SEQUENCE: 238
tgtaaaacga cggccagtgg tcagttgggc cttcataa                              38

<210> SEQ ID NO 239
<211> LENGTH: 39
<212> TYPE: DNA
<213> ORGANISM: Artificial Sequence
<220> FEATURE:
<223> OTHER INFORMATION: Primer

<400> SEQUENCE: 239
caggaaacag ctatgaccgg gcaaggtatc cttgaacat                             39

<210> SEQ ID NO 240
<211> LENGTH: 18
<212> TYPE: DNA
<213> ORGANISM: Artificial Sequence
<220> FEATURE:
<223> OTHER INFORMATION: Primer
```

```
<400> SEQUENCE: 240
tgtaaaacga cggccagt                                                  18

<210> SEQ ID NO 241
<211> LENGTH: 18
<212> TYPE: DNA
<213> ORGANISM: Artificial Sequence
<220> FEATURE:
<223> OTHER INFORMATION: Primer

<400> SEQUENCE: 241
caggaaacag ctatgacc                                                  18

<210> SEQ ID NO 242
<211> LENGTH: 18
<212> TYPE: DNA
<213> ORGANISM: Artificial Sequence
<220> FEATURE:
<223> OTHER INFORMATION: Primer

<400> SEQUENCE: 242
cccttcttga gagtccaa                                                  18

<210> SEQ ID NO 243
<211> LENGTH: 23
<212> TYPE: DNA
<213> ORGANISM: Artificial Sequence
<220> FEATURE:
<223> OTHER INFORMATION: Primer

<400> SEQUENCE: 243
tttttttttt ttttttttct gtt                                            23

<210> SEQ ID NO 244
<211> LENGTH: 19
<212> TYPE: DNA
<213> ORGANISM: Artificial Sequence
<220> FEATURE:
<223> OTHER INFORMATION: Primer

<400> SEQUENCE: 244
cctggagcag aaataattt                                                 19

<210> SEQ ID NO 245
<211> LENGTH: 18
<212> TYPE: DNA
<213> ORGANISM: Artificial Sequence
<220> FEATURE:
<223> OTHER INFORMATION: Primer

<400> SEQUENCE: 245
cccttcttga gagtccaa                                                  18

<210> SEQ ID NO 246
<211> LENGTH: 23
<212> TYPE: DNA
<213> ORGANISM: Artificial Sequence
<220> FEATURE:
<223> OTHER INFORMATION: Primer

<400> SEQUENCE: 246
tagtagtaaa aggaaagaaa cag                                            23

<210> SEQ ID NO 247
<211> LENGTH: 19
<212> TYPE: DNA
```

```
<213> ORGANISM: Artificial Sequence
<220> FEATURE:
<223> OTHER INFORMATION: Primer

<400> SEQUENCE: 247
cctggagcag aaataattt                                                    19

<210> SEQ ID NO 248
<211> LENGTH: 17
<212> TYPE: DNA
<213> ORGANISM: Artificial Sequence
<220> FEATURE:
<223> OTHER INFORMATION: Primer

<400> SEQUENCE: 248
ccttcccggg cctttct                                                      17

<210> SEQ ID NO 249
<211> LENGTH: 20
<212> TYPE: DNA
<213> ORGANISM: Artificial Sequence
<220> FEATURE:
<223> OTHER INFORMATION: Primer

<400> SEQUENCE: 249
ttccctgctc atggctgaat                                                   20

<210> SEQ ID NO 250
<211> LENGTH: 18
<212> TYPE: DNA
<213> ORGANISM: Artificial Sequence
<220> FEATURE:
<223> OTHER INFORMATION: Primer

<400> SEQUENCE: 250
tgtctctggt ctggtcag                                                     18

<210> SEQ ID NO 251
<211> LENGTH: 14
<212> TYPE: DNA
<213> ORGANISM: Homo sapien

<400> SEQUENCE: 251
gcgagctcgg gggg                                                         14

<210> SEQ ID NO 252
<211> LENGTH: 14
<212> TYPE: DNA
<213> ORGANISM: Homo sapien

<400> SEQUENCE: 252
gcgagctcgg tggg                                                         14

<210> SEQ ID NO 253
<211> LENGTH: 16
<212> TYPE: DNA
<213> ORGANISM: Homo sapien

<400> SEQUENCE: 253
gcgagctcgg gtgggg                                                       16

<210> SEQ ID NO 254
<211> LENGTH: 16
<212> TYPE: DNA
<213> ORGANISM: Homo sapien
```

-continued

```
<400> SEQUENCE: 254
gcgagctcgg gggggg                                                      16

<210> SEQ ID NO 255
<211> LENGTH: 14
<212> TYPE: PRT
<213> ORGANISM: Homo sapien

<400> SEQUENCE: 255

Thr Leu Arg Pro Pro Thr Leu Gln Pro Pro Thr Leu Gln Pro
 1               5                  10

<210> SEQ ID NO 256
<211> LENGTH: 42
<212> TYPE: DNA
<213> ORGANISM: Homo sapien

<400> SEQUENCE: 256
actctgcggc cgcctactct gcagccgccc actctgcagc cg                         42

<210> SEQ ID NO 257
<211> LENGTH: 12
<212> TYPE: DNA
<213> ORGANISM: Homo sapien

<400> SEQUENCE: 257
actctgcagc cg                                                          12

<210> SEQ ID NO 258
<211> LENGTH: 4
<212> TYPE: PRT
<213> ORGANISM: Homo sapien

<400> SEQUENCE: 258

Thr Leu Gln Pro
 1
```